US010940160B2

(12) United States Patent
Figueroa et al.

(10) Patent No.: US 10,940,160 B2
(45) Date of Patent: Mar. 9, 2021

(54) BIOMARKERS FOR PREDICTING RESPONSIVENESS TO DECITABINE THERAPY

(71) Applicant: The Regents of the University of Michigan, Ann Arbor, MI (US)

(72) Inventors: Maria Figueroa, Ann Arbor, MI (US); Kirsten M. Plasseraud, Ann Arbor, MI (US); Tingting Qin, Ann Arbor, MI (US); Valeria Santini, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 15/540,524

(22) PCT Filed: Dec. 21, 2015

(86) PCT No.: PCT/US2015/067084
§ 371 (c)(1),
(2) Date: Jun. 28, 2017

(87) PCT Pub. No.: WO2016/109284
PCT Pub. Date: Jul. 7, 2016

(65) Prior Publication Data
US 2017/0368091 A1  Dec. 28, 2017

Related U.S. Application Data

(60) Provisional application No. 62/097,279, filed on Dec. 29, 2014.

(51) Int. Cl.
| | |
|---|---|
| *C12Q 1/6886* | (2018.01) |
| *A61K 31/7068* | (2006.01) |
| *G01N 27/64* | (2006.01) |
| *G01N 33/50* | (2006.01) |
| *G01N 33/53* | (2006.01) |
| *G01N 33/574* | (2006.01) |

(52) U.S. Cl.
CPC ........ *A61K 31/7068* (2013.01); *C12Q 1/6886* (2013.01); *G01N 27/64* (2013.01); *G01N 33/5047* (2013.01); *G01N 33/53* (2013.01); *G01N 33/57426* (2013.01); *C12Q 2600/106* (2013.01); *C12Q 2600/154* (2013.01)

(58) Field of Classification Search
None
See application file for complete search history.

(56) References Cited

U.S. PATENT DOCUMENTS

2006/0019270 A1\* 1/2006 Yang ................... C12Q 1/6827
435/6.12
2014/0274748 A1  9/2014 Ahlquist et al.

FOREIGN PATENT DOCUMENTS

WO    WO 2014/044848    3/2014

OTHER PUBLICATIONS

Cobb et al (Crit Care Med 2002 vol. 30 p. 2711) (Year: 2002).\*
Tong et al. (Epigenetics 2010 vol. 5 p. 499-508) (Year: 2010).\*
Dunwell et al. (Molecular Cancer 2010 vol. 9 p. 44) (Year: 2010).\*
Abdel-Wahab, O., et al., "Genetic characterization of TET1, TET2, and TET3 alterations in myeloid malignancies." Blood. 2009;114(1):144-147.
Aivado, M., et al., "Serum proteome profiling detects myelodysplastic syndromes and identifies CXC chemokine ligands 4 and 7 as markers for advanced disease" Proc Natl Acad Sci U S A. 2007;104(4):1307-1312.
Akalin, A., et al., "Base-pair resolution DNA methylation sequencing reveals profoundly divergent epigenetic landscapes in acute myeloid leukemia." PLoS Genet. 2012;8(6):e1002781.
Anders, S., Pyl, P.T., and Huber, W. "HTSeq – A Python framework to work with high-throughput sequencing data." Bioinformatics, 2015 15;31(2): 166-9.
Bagger, F.O., et al., "HemaExplorer: a Web server for easy and fast visualization of gene expression in normal and malignant hematopoiesis" Blood. 2012;119(26):6394-6395.
Bagger, F.O., et al., "HemaExplorer: a database of mRNA expression profiles in normal and malignant haematopoiesis" Nucleic Acids Res. 2013;41(Database issue):D1034-1039.
Bejar, et al., "TET2 mutations predict response to hypomethylating agents in myelodysplastic syndrome patients." Blood 2014;124(17):2705-2712.
Bejar, R., "Clinical effect of point mutations in myelodysplastic syndromes." N Engl J Med. 2011;364(26):2496-2506.
Blum, W., et al., "Phase I Study of Decitabine Alone or in Combination With Valproic Acid in Acute Myeloid Leukemia" J Clin Oncol. 2007;25(25):3884-3891.
Bolger, A.M., Lohse, M., and Usadel, B. "Trimmomatic: a flexible trimmer for Illumina sequence data." Bioinformatics. Aug. 1, 2014;30(15):2114-20.
Braun, T., et al. "Molecular predictors of response to decitabine in advanced chronic myelomonocytic leukemia: a phase 2 trial." Blood. 2011;118(14):3824-3831.
Bruns, et al., "Megakaryocytes regulate hematopoietic stem cell quiescence through CXCL4 secretion" Nature Medicine 20, 1315-1320 2014.
Bullinger, L., et al., "Quantitative DNA methylation predicts survival in adult acute myeloid leukemia." Blood. 2010;115(3):636-642.
Chen, C., et al., "Identification of disease- and therapy-associated proteome changes in the sera of patients with myelodysplastic syndromes and del(5q)" Leukemia. 2010;24(11):1875-1884.

(Continued)

*Primary Examiner* — Katherine D Salmon
(74) *Attorney, Agent, or Firm* — Casimir Jones, SC; Robert A. Goetz

(57) ABSTRACT

Provided herein is technology relating to predicting a subject's resistance or responsiveness to a decitabine based therapy and particularly, but not exclusively, to methods, compositions, and related uses for predicting a subject's resistance or responsiveness to a decitabine based therapy wherein the subject is diagnosed with chronic myelomonocytic leukemia.

3 Claims, 71 Drawing Sheets

Specification includes a Sequence Listing.

(56) References Cited

OTHER PUBLICATIONS

Cheson, B.D., "Clinical application and proposal for modification of the International Working Group (IWG) response criteria in myelodysplasia" Blood. 2006;108(2):419-425.
Cihak, A., et al., "Effects of 5-azacytidine on hepatic polyribosomes and maturation of ribosomal RNA." Acta Biol Med Ger. 1974;33(5-6):859-865.
Cortes, C., and Vapnik, V. "Support-Vector Networks" Machine Learning. 1995;20(3):273-297.
Daskalakis, M., et al., "Demethylation of a hypermethylated P15/INK4B gene in patients with myelodysplastic syndrome by 5-Aza-2'-deoxycytidine (decitabine) treatment." Blood. 2002;100(8):2957-2964.
Depristo, M.A., et al., "A framework for variation discovery and genotyping using next-generation DNA sequencing data" Nat Genet. 2011;43(5):491-498.
Dudek, A.Z., et al., "Platelet factor 4 promotes adhesion of hematopoietic progenitor cells and binds IL-8: novel mechanisms for modulation of hematopoiesis" Blood. 2003;101(12):4687-4694.
Enrich, M., et al., "Quantitative high-throughput analysis of DNA methylation patterns by base-specific cleavage and mass spectrometry" Proc Natl Acad Sci U S A. 2005;102(44):15785-15790.
Ernst, T., et al., "Inactivating mutations of the histone methyltransferase gene EZH2 in myeloid disorders." Nat Genet. 2010;42(8):722-726.
Fandy, T.E., et al., "Early epigenetic changes and DNA damage do not predict clinical response in an overlapping schedule of 5-azacytidine and entinostat in patients with myeloid malignancies" Blood. 2009;114(13):2764-2773.
Figueroa, M.E., et al., "MDS and secondary AML display unique patterns and abundance of aberrant DNA methylation" Blood. 2009;114(16):3448-3458.
Figueroa, M.E., et al., "Leukemic IDH1 and IDH2 mutations result in a hypermethylation phenotype, disrupt TET2 function, and impair hematopoietic differentiation" Cancer Cell. 2010;18(6):553-567.
Figueroa, M.E., et al., "Integrated genetic and epigenetic analysis of childhood acute lymphoblastic leukemia" J Clin Invest. 2013;123(7):3099-3111.
Flotho C et al. The DNA methyltransferase inhibitors azacitidine, decitabine and zebularine exert differential effects on cancer gene expression in acute myeloid leukemia cells. Leukemia 2009;23:1019-1028.
Follo, M.Y., et al., "Reduction of phosphoinositide-phospholipase C beta1 methylation predicts the responsiveness to azacitidine in high-risk MDS" Proc Natl Acad Sci U S A. 2009;106(39):16811-16816.
Foucar K "Myelodysplastic/myeloproliferative neoplasms." (2009) Am. J. Clin. Pathol. 132 (2): 281-9.
Gelsi-Boyer, V., et al., "Mutations of polycomb-associated gene ASXL1 in myelodysplastic syndromes and chronic myelomonocytic leukaemia." Br J Haematol. 2009;145(6):788-800.
Gentleman, R.C., et al., "Bioconductor: open software development for computational biology and bioinformatics." Genome Biol. 2004;5(10):R80.
Ghoshal, K., et al., "5-Aza-deoxycytidine induces selective degradation of DNA methyltransferase 1 by a proteasomal pathway that requires the KEN box, bromo-adjacent homology domain, and nuclear localization signal." Mol Cell Biol. 2005;25(11):4727-4741.
Gore, S.D., et al., "Combined DNA Methyltransferase and Histone Deacetylase Inhibition in the Treatment of Myeloid Neoplasms" Cancer Res. 2006;66(12):6361-6369.
Graham, S.M., et al., "Transcriptional analysis of quiescent and proliferating CD34+ human hemopoietic cells from normal and chronic myeloid leukemia sources." Stem Cells. 2007;25(12):3111-3120.
Griffiths, E.A., and Gore, S.D. "DNA methyltransferase and histone deacetylase inhibitors in the treatment of myelodysplastic syndromes." Semin Hematol. 2008;45(1):23-30.
Gupta, S.K., and Singh, J.P. "Inhibition of endothelial cell proliferation by platelet factor-4 involves a unique action on S phase progression." J Cell Biol. 1994;127(4):1121-1127.
Han, Z.C., et al., "Platelet Factor 4 and Other CXC Chemokines Support the Survival of Normal Hematopoietic Cells and Reduce the Chemosensitivity of Cells to Cytotoxic Agents" Blood. 1997;89(7):2328-2335.
International Search Report and Written Opinion, International Patent Application No. PCT/US2015/067084, dated May 4, 2016.
Issa, J.P., et al., "Phase 1 study of low-dose prolonged exposure schedules of the hypomethylating agent 5-aza-2'-deoxycytidine (decitabine) in hematopoietic malignancies." Blood. 2004;103(5):1635-1640.
Itzykson, R., et al., "Prognostic factors for response and overall survival in 282 patients with higher-risk myelodysplastic syndromes treated with azacitidine" Blood. 2011;117(2):403-411.
Itzykson, R., et al., "Prognostic score including gene mutations in chronic myelomonocytic leukemia." J Clin Oncol. 2013;31(19):2428-2436.
Itzykson, R., "Impact of TET2 mutations on response rate to azacitidine in myelodysplastic syndromes and low blast count acute myeloid leukemias." Leukemia. 2011;25(7):1147-1152.
Jankowska, A.M., "Mutational spectrum analysis of chronic myelomonocytic leukemia includes genes associated with epigenetic regulation: UTX, EZH2, and DNMT3A" Blood. 2011;118(14):3932-3941.
Jiang, L., et al., "Synthetic spike-in standards for RNA-seq experiments" Genome Res. 2011;21(9):1543-1551.
Jiang, Y., et al., "Aberrant DNA methylation is a dominant mechanism in MDS progression to AML." Blood. 2009;113(6):1315-1325.
Kantarjian, H., et al. "Results of a randomized study of 3 schedules of low-dose decitabine in higher-risk myelodysplastic syndrome and chronic myelomonocytic leukemia.", Blood. 2007;109(1):52-57.
Kantarjian H., et al., "Decitabine improves patient outcomes in myelodysplastic syndromes: results of a phase III randomized study." Cancer. 2006;106(8):1794-1803.
Khan, S.N., et al., "Multiple mechanisms deregulate EZH2 and histone H3 lysine 27 epigenetic changes in myeloid malignancies" Leukemia. 2013;27(6):1301-1309.
Kittang, A.O., et al., "The chemokine network in acute myelogenous leukemia: Molecular mechanisms involved in leukemogenesis and therapeutic implications." Curr Top Microbiol Immunol. 2010;341(149-172.
Kohlmann, A., "Next-Generation Sequencing Technology Reveals a Characteristic Pattern of Molecular Mutations in 72.8% of Chronic Myelomonocytic Leukemia by Detecting Frequent Alterations in TET2, CBL, RAS, and RUNX1" J Clin Oncol. 2010;28(24):3858-3865.
Kosmider O., "TET2 gene mutation is a frequent and adverse event in chronic myelomonocytic leukemia." Haematologica. 2009;94(12):1676-1681.
Krueger F., and Andrews, S.R. "Bismark: a flexible aligner and methylation caller for Bisulfite-Seq applications." Bioinformatics. 2011;27(11):1571-1572.
Li, H., and Durbin, R. "Fast and accurate short read alignment with Burrows-Wheeler transform." Bioinformatics. 2009;25(14):1754-1760.
Ma, X., et al., "Myelodysplastic syndromes: incidence and survival in the United States." Cancer. 2007;109(8):1536-1542.
Makishima H., et al., "Novel homo- and hemizygous mutations in EZH2 in myeloid malignancies" Leukemia. 2010;24(10):1799-1804.
Malik et al. "Decitabine in the treatment of acute myeloid leukemia in elderly patients" Cancer Management and Research, vol. 6, pp. 53-61 (Feb. 2014).
Marcucci et al. "Epigenetics meets genetics in acute myeloid leukemia: clinical impact of a novel seven-gene score" Journal of Clinical Oncology, vol. 32, No. 6, pp. 548-556 (Feb. 2014).
Meggendorfer, M., "SRSF2 mutations in 275 cases with chronic myelomonocytic leukemia (CMML)." Blood. 2012;120(15):3080-3088.

(56) References Cited

OTHER PUBLICATIONS

Meldi et al. "Specific molecular signatures predict decitabine response in chronic myelomonocytic leukemia" The Journal of Clinical Investigation, vol. 125, No. 5, pp. 1857-1872 (May 2015).
Moreaux J et al. Development of gene expression-based score to predict sensitivity of multiple myeloma cells to DNA methylation inhibitors. Mol Cancer Ther. Dec. 2012;11(12):2685-92.
Mund, C., et al., "Characterization of DNA Demethylation Effects Induced by 5-Aza-2'-Deoxycytidine in Patients with Myelodysplastic Syndrome" Cancer Res. 2005;65(16):7086-7090.
Nikoloski, G., et al., "Somatic mutations of the histone methyltransferase gene ezh2 in myelodysplastic syndromes." Nat Genet. 2010;42(8):665-667.
Nimer, S.D. "Myelodysplastic syndromes." Blood. 2008;111(10):4841-4851.
Palii, S.S., et al., "DNA methylation inhibitor 5-Aza-2'-deoxycytidine induces reversible genome-wide DNA damage that is distinctly influenced by DNA methyltransferases 1 and 3B." Mol Cell Biol. 2008;28(2):752-771.
Park, Y., et al., "MethylSig: a whole genome DNA methylation analysis pipeline." Bioinformatics. Sep. 1, 2014;30(17):2414-22.
Patel, K., et al., "Targeting of 5-aza-2'-deoxycytidine residues by chromatin-associated DNMT1 induces proteasomal degradation of the free enzyme." Nucleic Acids Res. 2010;38(13):4313-4324.
Patnaik, M.M., "Spliceosome mutations involving SRSF2, SF3B1, and U2AF35 in chronic myelomonocytic leukemia: prevalence, clinical correlates, and prognostic relevance." Am J Hematol. 2013;88(3):201-206.
Patnaik, M.M., et al., "Mayo prognostic model for WHO-defined chronic myelomonocytic leukemia: ASXL1 and spliceosome component mutations and outcomes" Leukemia. 2013;27(7):1504-1510.
Pillai, M.M., et al., "Monocyte-derived CXCL7 peptides in the marrow microenvironment" Blood. 2006;107(9):3520-3526.
Reikvam, H., et al., "The Possible Diagnostic and Prognostic Use of Systemic Chemokine Profiles in Clinical Medicine—The Experience in Acute Myeloid Leukemia from Disease Development and Diagnosis via Conventional Chemotherapy to Allogeneic Stem Cell Transplantation" Toxins (Basel). 2013;5(2):336-362.
Robinson, M.D., et al., "edgeR: a Bioconductor package for differential expression analysis of digital gene expression data." Bioinformatics. 2010;26(1):139-140.
Sanyal, A., et al., "The long-range interaction landscape of gene promoters" Nature. 2012;489(7414):109-113.
Schaffner, A., et al., "Regulated expression of platelet factor 4 in human monocytes—role of PARs as a quantitatively important monocyte activation pathway" J Leukoc Biol. 2005;78(1):202-209.
Schmutz et al. "Differential DNA Methylation Predicts Response to Combined Treatment Regimens with a DNA Methyltransferase Inhibitor in Acute Myeloid Leukemia (AML)" Nov. 15, 2013; Blood:122(21). Abstract.
Shen, L., et al., "DNA Methylation Predicts Survival and Response to Therapy in Patients With Myelodysplastic Syndromes" J Clin Oncol. 2010;28(4):605-613.
Silverman, L.R., et al., "Randomized controlled trial of azacitidine in patients with the myelodysplastic syndrome: a study of the cancer and leukemia group B." J Clin Oncol. 2002;20(10):2429-2440.
Sing, T., et al., "ROCR: visualizing classifier performance in R." Bioinformatics. 2005;21(20):3940-3941.
Subramanian, A., et al., "Gene set enrichment analysis: A knowledge-based approach for interpreting genome-wide expression profiles" Proc Natl Acad Sci U S A. 2005;102(43):15545-15550.
Tefferi, A., et al., "Detection of mutant TET2 in myeloid malignancies other than myeloproliferative neoplasms: CMML, MDS, MDS/MPN and AML" Leukemia. 2009;23(7):1343-1345.
Traina F et al. "Impact of molecular mutations on treatment response to DNMT inhibitors in myelodysplasia and related neoplasms." Leukemia 2014;28:78-87.
Trapnell, C., et al., "Differential analysis of gene regulation at transcript resolution with RNA-seq." Nat Biotechnol. 2013;31(1):46-53.
Treppendahl et al. "Predicting response to epigenetic therapy" The Journal of Clinical Investigation, vol. 124, No. 1, pp. 47-55 (Jan. 2014).
Tsai, H.C., et al., "Transient low doses of DNA-demethylating agents exert durable antitumor effects on hematological and epithelial tumor cells." Cancer Cell. 2012;21(3):430-446.
Vardiman JW, et al., "The World Health Organization (WHO) classification of the myeloid neoplasms." (2002) Blood 100 (7): 2292-302.
Walter, M.J., et al., "Recurrent DNMT3A mutations in patients with myelodysplastic syndromes." Leukemia. 2011;25(7):1153-1158.
Wang, K., Li, M., and Hakonarson, H. "ANNOVAR: functional annotation of genetic variants from high-throughput sequencing data." Nucleic Acids Res. 2010;38(16):e164.
WHO, I. 2008. World Health Organization classification of tumors of haematopoietic and lymphoid tissues Lyon: International Agency for Cancer (IARC). 439 pp, Book—table of contents only.
Yan et al. "Genome-wide methylation profiling in decitabine-treated patients with acute myeloid leukemia" Blood, vol. 120, No. 12, pp. 2466-2474 (2012).
Yoshida, K., "Frequent pathway mutations of splicing machinery in myelodysplasia" Nature. 2011;478(7367):64-69.

\* cited by examiner

FIG. 3A
FIG. 3B
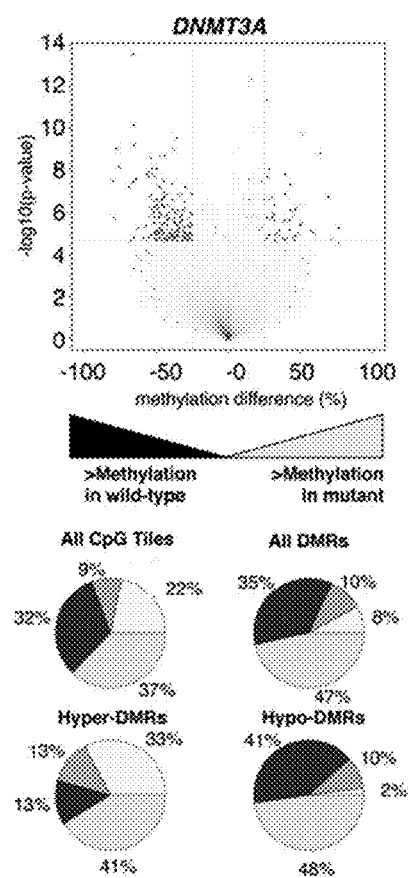
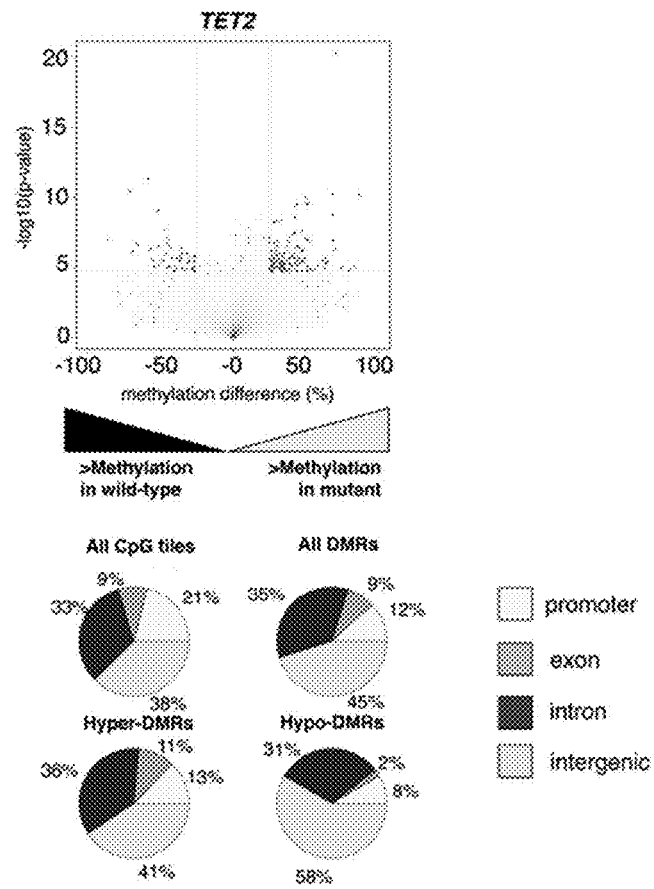

FIG. 3C
FIG. 3D
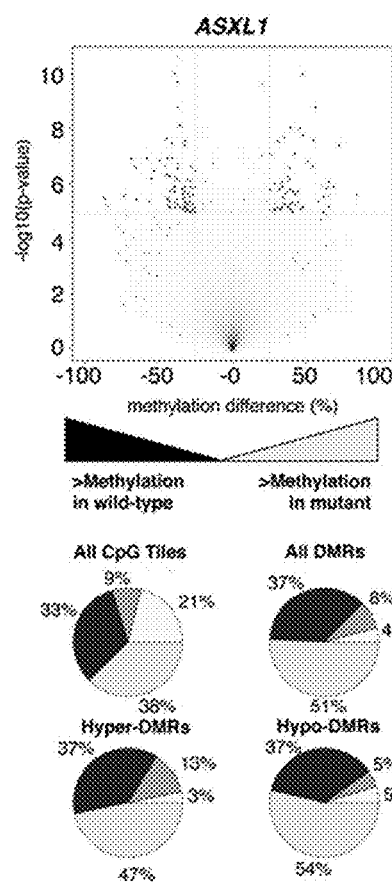
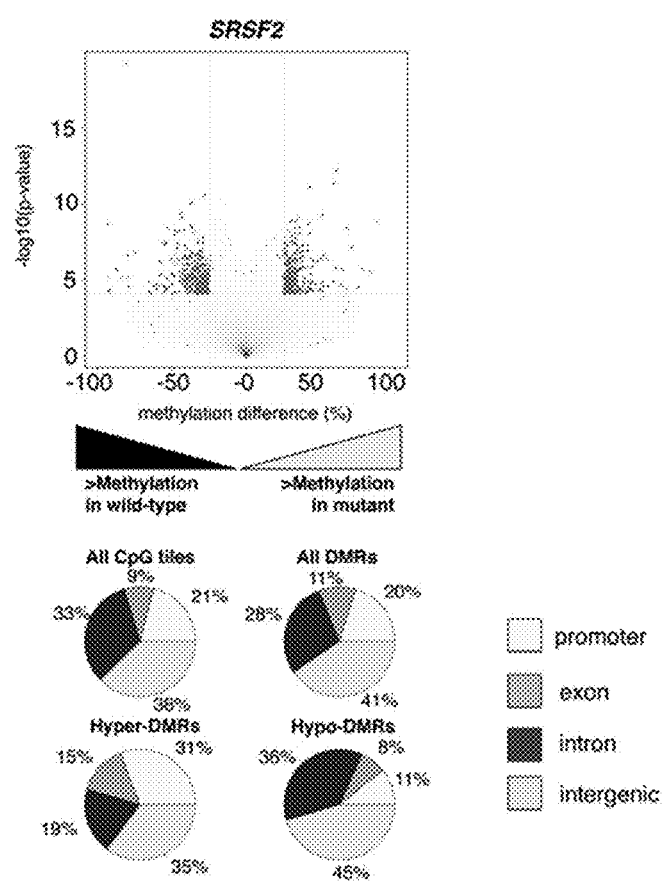

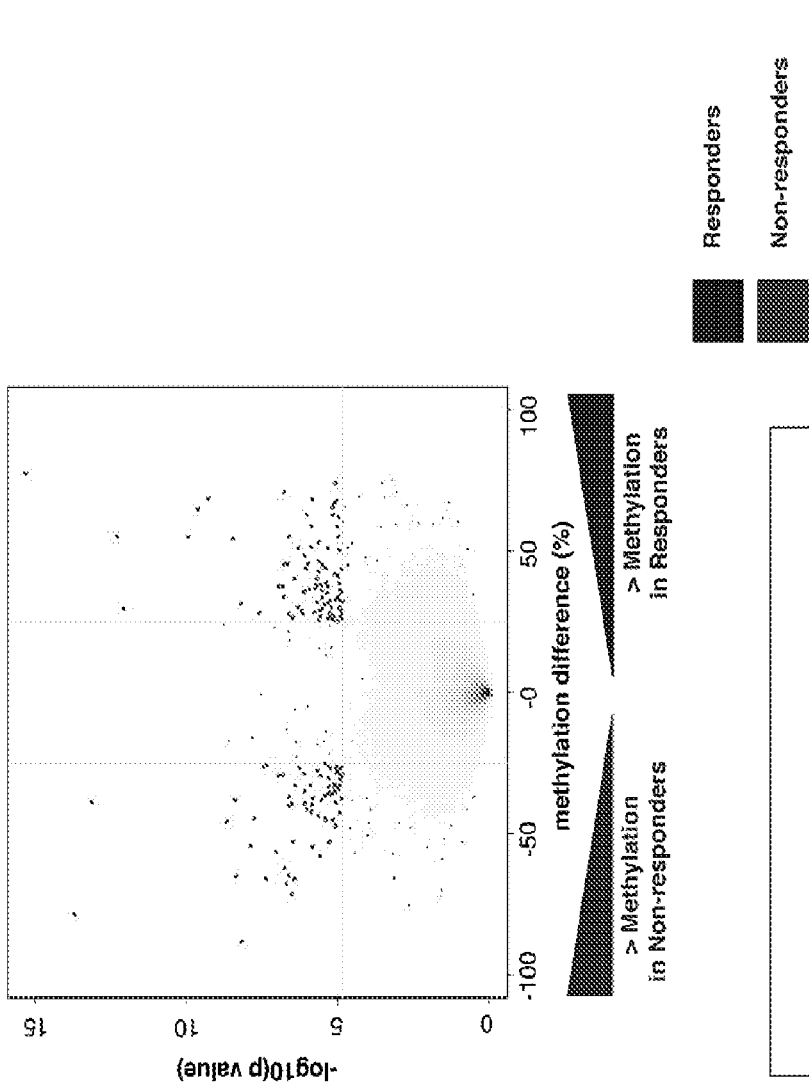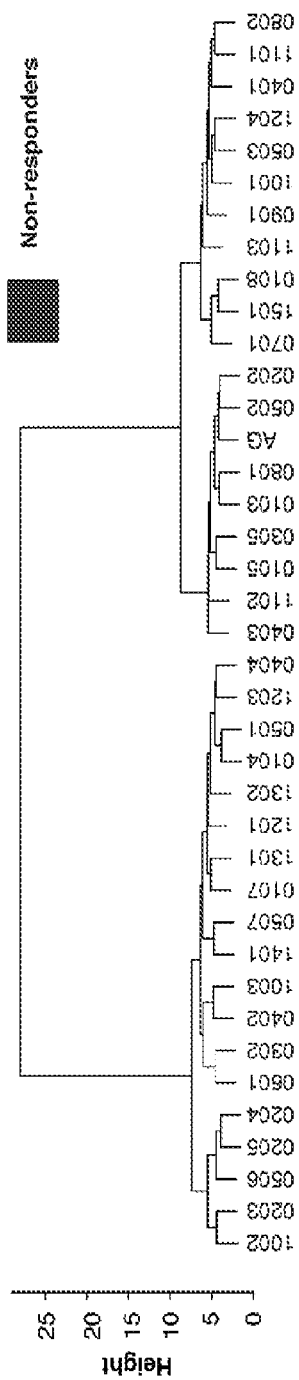
FIG. 4A
FIG. 4B

FIG. 4C

| Chromosome | DMR start | DMR end | Gene_AccessID | Gene Symbol |
|---|---|---|---|---|
| chr1 | 1210985 | 1211009 | NR_037668 | SCNN1D |
| chr1 | 1210985 | 1211009 | NM_001130413 | SCNN1D |
| chr1 | 3807785 | 3807809 | NR_024455 | LOC100133612 |
| chr1 | 10518585 | 10518609 | NM_004565 | PEX14 |
| chr1 | 16720135 | 16720159 | NR_023386 | CROCCP3 |
| chr1 | 16720135 | 16720159 | NR_037446 | MIR3675 |
| chr1 | 26108385 | 26108409 | NM_024037 | AUNIP |
| chr1 | 26108385 | 26108409 | NM_178422 | PAQR7 |
| chr1 | 26108385 | 26108409 | NM_001145454 | STMN1 |
| chr1 | 26108385 | 26108409 | NM_203399 | STMN1 |
| chr1 | 26108385 | 26108409 | NM_203401 | STMN1 |
| chr1 | 26108385 | 26108409 | NR_037481 | MIR3917 |
| chr1 | 26108385 | 26108409 | NM_005563 | STMN1 |
| chr1 | 26544285 | 26544309 | NM_001039775 | AIM1L |
| chr1 | 30487535 | 30487559 | NR_034182 | MATN1-AS1 |
| chr1 | 54848035 | 54848059 | NM_015547 | ACOT11 |
| chr1 | 54848035 | 54848059 | NM_176782 | FAM151A |
| chr1 | 54848035 | 54848059 | NM_147161 | ACOT11 |
| chr1 | 109447985 | 109448009 | NM_001122961 | C1orf194 |
| chr1 | 109447985 | 109448009 | NM_005645 | TAF13 |
| chr1 | 109447985 | 109448009 | NR_003023 | SCARNA2 |
| chr1 | 109447985 | 109448009 | NM_020141 | TMEM167B |
| chr1 | 109447985 | 109448009 | NR_049773 | KIAA1324 |
| chr1 | 109447985 | 109448009 | NM_001267048 | KIAA1324 |
| chr1 | 109447985 | 109448009 | NM_020775 | KIAA1324 |
| chr1 | 179721435 | 179721459 | NM_001205294 | CACNA1E |
| chr1 | 179721435 | 179721459 | NM_001205293 | CACNA1E |
| chr1 | 179721435 | 179721459 | NM_000721 | CACNA1E |
| chr1 | 226029760 | 226029784 | NM_053052 | SNAP47 |
| chr1 | 232915960 | 232915984 | NR_038856 | LOC100506810 |
| chr10 | 46419094 | 46419118 | NM_014696 | GPRIN2 |
| chr10 | 72497294 | 72497318 | NM_170744 | UNC5B |
| chr10 | 72497294 | 72497318 | NM_001244889 | UNC5B |
| chr10 | 96933094 | 96933118 | NM_207321 | C10orf129 |

FIG. 4C (cont'd)

| chr10 | 125178044 | 125178068 | NM_153442    | GPR26   |
|-------|-----------|-----------|--------------|---------|
| chr11 | 2192653   | 2192677   | NM_000360    | TH      |
| chr11 | 2192653   | 2192677   | NM_199292    | TH      |
| chr11 | 2192653   | 2192677   | NM_199293    | TH      |
| chr11 | 2192653   | 2192677   | NR_039834    | MIR4686 |
| chr11 | 7230253   | 7230277   | NM_175733    | SYT9    |
| chr11 | 26972378  | 26972402  | NM_203371    | FIBIN   |
| chr11 | 34159603  | 34159627  | NM_145804    | ABTB2   |
| chr11 | 44298178  | 44298202  | NM_021926    | ALX4    |
| chr11 | 63732703  | 63732727  | NM_031471    | FERMT3  |
| chr11 | 63732703  | 63732727  | NM_178443    | FERMT3  |
| chr11 | 64733978  | 64734002  | NM_001198869 | CAPN1   |
| chr11 | 64733978  | 64734002  | NR_040008    | CAPN1   |
| chr11 | 64733978  | 64734002  | NM_005186    | CAPN1   |
| chr11 | 64733978  | 64734002  | NM_001198868 | CAPN1   |
| chr11 | 65417228  | 65417252  | NM_005438    | FOSL1   |
| chr11 | 76428753  | 76428777  | NM_138706    | B3GNT6  |
| chr11 | 85945303  | 85945327  | NM_006680    | ME3     |
| chr11 | 85945303  | 85945327  | NM_001161586 | ME3     |
| chr11 | 85945303  | 85945327  | NM_001014811 | ME3     |
| chr12 | 27955362  | 27955386  | NM_198966    | PTHLH   |
| chr12 | 27955362  | 27955386  | NM_198964    | PTHLH   |
| chr12 | 30605812  | 30605836  | NM_001190995 | IPO8    |
| chr12 | 43731612  | 43731636  | NR_026583    | RACGAP1P|
| chr12 | 43731612  | 43731636  | NM_001004329 | DBX2    |
| chr12 | 53049112  | 53049136  | NM_020370    | GPR84   |
| chr12 | 53049112  | 53049136  | NM_001130967 | ZNF385A |
| chr12 | 53049112  | 53049136  | NM_001130968 | ZNF385A |
| chr12 | 53049112  | 53049136  | NM_016057    | COPZ1   |
| chr12 | 53049112  | 53049136  | NM_015481    | ZNF385A |
| chr12 | 53049112  | 53049136  | NR_029894    | MIR148B |
| chr12 | 53049112  | 53049136  | NM_001271736 | COPZ1   |
| chr12 | 53049112  | 53049136  | NM_001271734 | COPZ1   |
| chr12 | 53049112  | 53049136  | NM_001271735 | COPZ1   |
| chr12 | 53049112  | 53049136  | NR_073424    | COPZ1   |
| chr12 | 53049137  | 53049161  | NM_020370    | GPR84   |
| chr12 | 53049137  | 53049161  | NM_001130967 | ZNF385A |

FIG. 4C (cont'd)

| | | | | |
|---|---|---|---|---|
| chr12 | 53049137 | 53049161 | NM_001130968 | ZNF385A |
| chr12 | 53049137 | 53049161 | NM_016057 | COPZ1 |
| chr12 | 53049137 | 53049161 | NM_015481 | ZNF385A |
| chr12 | 53049137 | 53049161 | NR_029894 | MIR148B |
| chr12 | 53049137 | 53049161 | NM_001271736 | COPZ1 |
| chr12 | 53049137 | 53049161 | NM_001271734 | COPZ1 |
| chr12 | 53049137 | 53049161 | NM_001271735 | COPZ1 |
| chr12 | 53049137 | 53049161 | NR_073424 | COPZ1 |
| chr13 | 29008021 | 29008045 | NM_003045 | SLC7A1 |
| chr13 | 107316571 | 107316595 | NM_001080396 | FAM155A |
| chr13 | 107946846 | 107946870 | NM_015011 | MYO16 |
| chr13 | 110103771 | 110103795 | NM_024537 | CARS2 |
| chr13 | 112399146 | 112399170 | NM_032189 | ATP11A |
| chr13 | 112399146 | 112399170 | NM_015205 | ATP11A |
| chr13 | 112696571 | 112696595 | NM_001112732 | MCF2L |
| chr14 | 89274505 | 89274529 | NM_001085471 | FOXN3 |
| chr14 | 91723780 | 91723804 | NM_017437 | CPSF2 |
| chr14 | 99211380 | 99211404 | NM_001127258 | HHIPL1 |
| chr14 | 100245580 | 100245604 | NM_003836 | DLK1 |
| chr14 | 104779380 | 104779404 | NM_001242788 | BRF1 |
| chr14 | 104779380 | 104779404 | NM_001242787 | BRF1 |
| chr14 | 104779380 | 104779404 | NM_001242789 | BRF1 |
| chr14 | 104779380 | 104779404 | NM_145685 | BRF1 |
| chr14 | 104779380 | 104779404 | NM_001519 | BRF1 |
| chr14 | 104779380 | 104779404 | NM_001242786 | BRF1 |
| chr15 | 87992464 | 87992488 | NM_198525 | KIF7 |
| chr16 | 49298 | 49322 | NM_022450 | RHBDF1 |
| chr16 | 651573 | 651597 | NM_145294 | WDR90 |
| chr16 | 782698 | 782722 | NM_022092 | CHTF18 |
| chr16 | 1055798 | 1055822 | NR_027242 | SSTR5-AS1 |
| chr16 | 12262398 | 12262422 | NM_032167 | SNX29 |
| chr16 | 23766873 | 23766897 | NM_002738 | PRKCB |
| chr16 | 23766873 | 23766897 | NM_212535 | PRKCB |
| chr16 | 27659398 | 27659422 | NM_015202 | KIAA0556 |
| chr16 | 55870173 | 55870197 | NM_015993 | PLLP |
| chr16 | 55892523 | 55892547 | NM_015993 | PLLP |
| chr16 | 83973323 | 83973347 | NR_049816 | MIR5093 |

FIG. 4C (cont'd)

| | | | | |
|---|---|---|---|---|
| chr16 | 87171298 | 87171322 | NM_144604 | ZC3H18 |
| chr16 | 87567098 | 87567122 | NM_005187 | CBFA2T3 |
| chr16 | 87824373 | 87824397 | NM_001201407 | ZNF778 |
| chr16 | 87824373 | 87824397 | NR_037705 | ZNF778 |
| chr16 | 87824373 | 87824397 | NM_001242757 | SLC22A31 |
| chr16 | 87824373 | 87824397 | NM_182531 | ZNF778 |
| chr17 | 10022007 | 10022031 | NM_201433 | GAS7 |
| chr17 | 23875607 | 23875631 | NM_003593 | FOXN1 |
| chr17 | 38963482 | 38963506 | NM_001261438 | ETV4 |
| chr17 | 38963482 | 38963506 | NM_001261437 | ETV4 |
| chr17 | 38963482 | 38963506 | NM_001079675 | ETV4 |
| chr17 | 38963482 | 38963506 | NM_001986 | ETV4 |
| chr17 | 39624932 | 39624956 | NM_020218 | ATXN7L3 |
| chr17 | 39624932 | 39624956 | NM_001098833 | ATXN7L3 |
| chr17 | 41330532 | 41330556 | NM_016834 | MAPT |
| chr17 | 41330532 | 41330556 | NM_016835 | MAPT |
| chr17 | 41330532 | 41330556 | NM_001203252 | MAPT |
| chr17 | 41330532 | 41330556 | NM_001203251 | MAPT |
| chr17 | 41330532 | 41330556 | NM_001123066 | MAPT |
| chr17 | 41330532 | 41330556 | NM_001123067 | MAPT |
| chr17 | 41330532 | 41330556 | NM_005910 | MAPT |
| chr17 | 41330532 | 41330556 | NM_016841 | MAPT |
| chr17 | 41330532 | 41330556 | NR_024560 | MAPT-IT1 |
| chr17 | 72908007 | 72908031 | NM_006640 | 41891 |
| chr17 | 72908007 | 72908031 | NM_001113494 | 41891 |
| chr17 | 72908007 | 72908031 | NM_001113492 | 41891 |
| chr17 | 72908007 | 72908031 | NM_001113491 | 41891 |
| chr17 | 72908007 | 72908031 | NM_001113493 | 41891 |
| chr17 | 73230682 | 73230706 | NR_028337 | FLJ45079 |
| chr17 | 76673082 | 76673106 | NM_001144888 | BAIAP2 |
| chr17 | 76673082 | 76673106 | NM_006340 | BAIAP2 |
| chr17 | 76673082 | 76673106 | NM_017451 | BAIAP2 |
| chr17 | 76673082 | 76673106 | NM_017450 | BAIAP2 |
| chr17 | 77659982 | 77660006 | NM_198082 | CCDC57 |
| chr18 | 13914891 | 13914915 | NM_000529 | MC2R |
| chr18 | 43029316 | 43029340 | NM_001278063 | SKOR2 |
| chr18 | 43029316 | 43029340 | NM_001037802 | SKOR2 |

FIG. 4C (cont'd)

| chr18 | 55514841 | 55514865 | NM_133459 | CCBE1 |
|---|---|---|---|---|
| chr18 | 71835416 | 71835440 | NR_040034 | LOC339298 |
| chr18 | 73091116 | 73091140 | NM_001480 | GALR1 |
| chr18 | 75265166 | 75265190 | NM_172388 | NFATC1 |
| chr18 | 75265166 | 75265190 | NM_001278670 | NFATC1 |
| chr18 | 75265166 | 75265190 | NM_001278673 | NFATC1 |
| chr18 | 75265166 | 75265190 | NM_006162 | NFATC1 |
| chr18 | 75265166 | 75265190 | NM_172390 | NFATC1 |
| chr18 | 75265166 | 75265190 | NM_001278675 | NFATC1 |
| chr18 | 75265166 | 75265190 | NM_172389 | NFATC1 |
| chr18 | 75265166 | 75265190 | NM_001278672 | NFATC1 |
| chr18 | 75265166 | 75265190 | NM_172387 | NFATC1 |
| chr18 | 75265166 | 75265190 | NM_001278669 | NFATC1 |
| chr18 | 75437691 | 75437715 | NM_004715 | CTDP1 |
| chr18 | 75437691 | 75437715 | NM_048368 | CTDP1 |
| chr19 | 833925 | 833949 | NM_005481 | MED16 |
| chr19 | 961900 | 961924 | NM_033420 | TMEM259 |
| chr19 | 961900 | 961924 | NM_001033026 | TMEM259 |
| chr19 | 2013875 | 2013899 | NM_001039846 | IZUMO4 |
| chr19 | 2013875 | 2013899 | NM_199054 | MKNK2 |
| chr19 | 2013875 | 2013899 | NM_017797 | BTBD2 |
| chr19 | 2013875 | 2013899 | NM_001031735 | IZUMO4 |
| chr19 | 2013875 | 2013899 | NM_130807 | MOB3A |
| chr19 | 2013875 | 2013899 | NM_017572 | MKNK2 |
| chr19 | 3928300 | 3928324 | NM_001961 | EEF2 |
| chr19 | 4431975 | 4431999 | NM_032631 | HDGFRP2 |
| chr19 | 4431975 | 4431999 | NM_001001520 | HDGFRP2 |
| chr19 | 8022925 | 8022949 | NM_001419 | ELAVL1 |
| chr19 | 8022925 | 8022949 | NM_001201359 | CCL25 |
| chr19 | 8022925 | 8022949 | NM_005624 | CCL25 |
| chr19 | 8229300 | 8229324 | NM_024552 | CERS4 |
| chr19 | 8545700 | 8545724 | NM_012335 | MYO1F |
| chr19 | 16104225 | 16104249 | NM_005370 | RAB8A |
| chr19 | 21234450 | 21234474 | NM_021269 | ZNF708 |
| chr19 | 50454525 | 50454549 | NM_001199867 | MARK4 |
| chr19 | 50454525 | 50454549 | NM_031417 | MARK4 |
| chr19 | 52050525 | 52050549 | NM_004069 | AP2S1 |

FIG. 4C (cont'd)

| chr19 | 52050525 | 52050549 | NM_021575 | AP2S1 |
|---|---|---|---|---|
| chr19 | 52050525 | 52050549 | NR_024258 | SNAR-E |
| chr19 | 54750025 | 54750049 | NM_015953 | NOSIP |
| chr19 | 54750025 | 54750049 | NM_001136019 | FCGRT |
| chr19 | 54750025 | 54750049 | NM_020719 | PRR12 |
| chr19 | 54750025 | 54750049 | NM_000951 | PRRG2 |
| chr19 | 54750025 | 54750049 | NM_001270960 | NOSIP |
| chr19 | 54750025 | 54750049 | NM_020650 | RCN3 |
| chr19 | 54750025 | 54750049 | NM_004107 | FCGRT |
| chr19 | 54797050 | 54797074 | NM_020719 | PRR12 |
| chr19 | 55707325 | 55707349 | NM_001024656 | ASPDH |
| chr19 | 55707325 | 55707349 | NM_001114598 | ASPDH |
| chr19 | 60689975 | 60689999 | NM_020378 | NAT14 |
| chr2 | 1768284 | 1768308 | NM_012293 | PXDN |
| chr2 | 7089784 | 7089808 | NM_014746 | RNF144A |
| chr2 | 25408459 | 25408483 | NM_022552 | DNMT3A |
| chr2 | 25408459 | 25408483 | NM_175630 | DNMT3A |
| chr2 | 25408459 | 25408483 | NM_175629 | DNMT3A |
| chr2 | 26263434 | 26263458 | NM_001168241 | GAREML |
| chr2 | 26263434 | 26263458 | NM_001191033 | GAREML |
| chr2 | 62303059 | 62303083 | NM_006577 | B3GNT2 |
| chr2 | 86890084 | 86890108 | NM_001145873 | CD8A |
| chr2 | 86890084 | 86890108 | NM_171827 | CD8A |
| chr2 | 86890084 | 86890108 | NM_001768 | CD8A |
| chr2 | 86890084 | 86890108 | NR_027353 | CD8A |
| chr2 | 132511709 | 132511733 | NR_027019 | ANKRD30BL |
| chr2 | 168129384 | 168129408 | NM_020981 | B3GALT1 |
| chr2 | 204726609 | 204726633 | NM_012092 | ICOS |
| chr2 | 242197709 | 242197733 | NM_001164356 | THAP4 |
| chr2 | 242197709 | 242197733 | NM_015963 | THAP4 |
| chr20 | 3102643 | 3102667 | NM_033453 | ITPA |
| chr20 | 3102643 | 3102667 | NM_021826 | FASTKD5 |
| chr20 | 3102643 | 3102667 | NM_023935 | DDRGK1 |
| chr20 | 3102643 | 3102667 | NR_052002 | ITPA |
| chr20 | 3102643 | 3102667 | NM_014948 | UBOX5 |
| chr20 | 3102643 | 3102667 | NM_001267623 | ITPA |
| chr20 | 3102643 | 3102667 | NM_199415 | UBOX5 |

FIG. 4C (cont'd)

| chr20 | 3102643 | 3102667 | NM_001267584 | UBOX5 |
|---|---|---|---|---|
| chr20 | 3102643 | 3102667 | NR_052000 | ITPA |
| chr20 | 3102643 | 3102667 | NM_181493 | ITPA |
| chr20 | 3102643 | 3102667 | NR_052001 | ITPA |
| chr20 | 3102643 | 3102667 | NM_014731 | LZTS3 |
| chr20 | 17546168 | 17546192 | NM_001042576 | RRBP1 |
| chr20 | 17546168 | 17546192 | NM_004587 | RRBP1 |
| chr20 | 25229318 | 25229342 | NM_001042472 | ABHD12 |
| chr20 | 25229318 | 25229342 | NM_015600 | ABHD12 |
| chr20 | 25291443 | 25291467 | NM_001042472 | ABHD12 |
| chr20 | 25291443 | 25291467 | NM_015600 | ABHD12 |
| chr20 | 29478593 | 29478617 | NR_045677 | DEFB122 |
| chr20 | 37253318 | 37253342 | NR_027124 | LOC339568 |
| chr20 | 38906193 | 38906217 | NM_005461 | MAFB |
| chr20 | 56725368 | 56725392 | NM_024663 | NPEPL1 |
| chr20 | 56725368 | 56725392 | NM_001204873 | NPEPL1 |
| chr20 | 56725368 | 56725392 | NM_001204872 | NPEPL1 |
| chr20 | 60514443 | 60514467 | NM_080473 | GATA5 |
| chr20 | 60514443 | 60514467 | NR_029780 | MIR1-1 |
| chr20 | 60514443 | 60514467 | NR_033263 | C20orf166-AS1 |
| chr20 | 60514443 | 60514467 | NM_178463 | C20orf166 |
| chr20 | 61513618 | 61513642 | NM_004518 | KCNQ2 |
| chr20 | 61513618 | 61513642 | NM_172108 | KCNQ2 |
| chr20 | 61513618 | 61513642 | NM_172107 | KCNQ2 |
| chr20 | 61513618 | 61513642 | NM_172106 | KCNQ2 |
| chr21 | 44533977 | 44534001 | NM_000383 | AIRE |
| chr21 | 45790602 | 45790626 | NM_194255 | SLC19A1 |
| chr21 | 45790602 | 45790626 | NM_001205207 | SLC19A1 |
| chr21 | 45790602 | 45790626 | NM_001205206 | SLC19A1 |
| chr21 | 46141227 | 46141251 | NM_001130141 | PCBP3 |
| chr21 | 46141227 | 46141251 | NM_020528 | PCBP3 |
| chr22 | 19617686 | 19617710 | NM_005207 | CRKL |
| chr22 | 20636261 | 20636285 | NM_014634 | PPM1F |
| chr22 | 45359436 | 45359460 | NM_015124 | GRAMD4 |
| chr22 | 45359436 | 45359460 | NM_014246 | CELSR1 |
| chr22 | 48515036 | 48515060 | NR_026993 | LOC90834 |
| chr22 | 49221586 | 49221610 | NM_001242900 | PPP6R2 |

FIG. 4C (cont'd)

| chr22 | 49221586 | 49221610 | NM_014678 | PPP6R2 |
|---|---|---|---|---|
| chr22 | 49221586 | 49221610 | NM_001242899 | PPP6R2 |
| chr22 | 49221586 | 49221610 | NM_001242898 | PPP6R2 |
| chr3 | 12912595 | 12912619 | NM_000994 | RPL32 |
| chr3 | 12912595 | 12912619 | NM_001007073 | RPL32 |
| chr3 | 49492195 | 49492219 | NM_001177634 | DAG1 |
| chr3 | 49492195 | 49492219 | NM_001177635 | DAG1 |
| chr3 | 49492195 | 49492219 | NM_001177636 | DAG1 |
| chr3 | 49492195 | 49492219 | NM_001177637 | DAG1 |
| chr3 | 49492195 | 49492219 | NM_001177638 | DAG1 |
| chr3 | 49492195 | 49492219 | NM_001177639 | DAG1 |
| chr3 | 49492195 | 49492219 | NM_001165928 | DAG1 |
| chr3 | 49492195 | 49492219 | NM_001177641 | DAG1 |
| chr3 | 49492195 | 49492219 | NM_001177640 | DAG1 |
| chr3 | 49492195 | 49492219 | NM_001177642 | DAG1 |
| chr3 | 49492195 | 49492219 | NM_001177644 | DAG1 |
| chr3 | 49492195 | 49492219 | NM_004393 | DAG1 |
| chr3 | 49492195 | 49492219 | NM_001177643 | DAG1 |
| chr3 | 72309120 | 72309144 | NR_038221 | LINC00870 |
| chr3 | 75799770 | 75799794 | NR_037925 | FLJ20518 |
| chr3 | 75799770 | 75799794 | NR_040004 | LINC00960 |
| chr3 | 75799770 | 75799794 | NR_031714 | MIR1324 |
| chr3 | 75799770 | 75799794 | NM_001124759 | FRG2C |
| chr3 | 75799770 | 75799794 | NR_040005 | LINC00960 |
| chr3 | 75802345 | 75802369 | NR_037925 | FLJ20518 |
| chr3 | 75802345 | 75802369 | NR_040004 | LINC00960 |
| chr3 | 75802345 | 75802369 | NR_031714 | MIR1324 |
| chr3 | 75802345 | 75802369 | NM_001124759 | FRG2C |
| chr3 | 75802345 | 75802369 | NR_040005 | LINC00960 |
| chr3 | 129756595 | 129756619 | NR_026954 | LOC90246 |
| chr3 | 129756595 | 129756619 | NM_007354 | C3orf27 |
| chr4 | 1313454 | 1313478 | NM_001017405 | MAEA |
| chr4 | 1313454 | 1313478 | NM_005882 | MAEA |
| chr4 | 7971079 | 7971103 | NM_198595 | AFAP1 |
| chr4 | 7971079 | 7971103 | NM_001134647 | AFAP1 |
| chr4 | 120547604 | 120547628 | NR_037596 | LINC01061 |
| chr5 | 552538 | 552562 | NM_004174 | SLC9A3 |

FIG. 4C (cont'd)

| chr5 | 728288 | 728312 | NM_007030 | TPPP |
|---|---|---|---|---|
| chr5 | 1273013 | 1273037 | NM_001003841 | SLC6A19 |
| chr5 | 32481238 | 32481262 | NM_016107 | ZFR |
| chr5 | 40823263 | 40823287 | NM_206907 | PRKAA1 |
| chr5 | 40823263 | 40823287 | NM_006251 | PRKAA1 |
| chr5 | 50511663 | 50511687 | NM_002202 | ISL1 |
| chr5 | 114146613 | 114146637 | NM_170775 | KCNN2 |
| chr5 | 114146613 | 114146637 | NR_103458 | KCNN2 |
| chr5 | 174261338 | 174261362 | NR_046113 | FLJ16171 |
| chr5 | 179975988 | 179976012 | NM_182925 | FLT4 |
| chr5 | 179975988 | 179976012 | NM_002020 | FLT4 |
| chr6 | 287697 | 287721 | NM_020185 | DUSP22 |
| chr6 | 3689547 | 3689571 | NM_183373 | PXDC1 |
| chr6 | 32610447 | 32610471 | NM_002125 | HLA-DRB5 |
| chr6 | 32610447 | 32610471 | NR_001298 | HLA-DRB6 |
| chr6 | 149837197 | 149837221 | NM_207360 | ZC3H12D |
| chr7 | 1905181 | 1905205 | NM_003550 | MAD1L1 |
| chr7 | 1905181 | 1905205 | NM_001013836 | MAD1L1 |
| chr7 | 1905181 | 1905205 | NM_001013837 | MAD1L1 |
| chr7 | 4740731 | 4740755 | NM_001037165 | FOXK1 |
| chr7 | 4926256 | 4926280 | NM_001270375 | MMD2 |
| chr7 | 4926256 | 4926280 | NM_198403 | MMD2 |
| chr7 | 4926256 | 4926280 | NM_001100600 | MMD2 |
| chr7 | 4926256 | 4926280 | NR_072989 | MMD2 |
| chr7 | 5592756 | 5592780 | NM_003088 | FSCN1 |
| chr7 | 45164481 | 45164505 | NM_005856 | RAMP3 |
| chr7 | 63882756 | 63882780 | NR_073391 | ZNF138 |
| chr7 | 63882756 | 63882780 | NM_006524 | ZNF138 |
| chr7 | 63882756 | 63882780 | NM_001160183 | ZNF138 |
| chr7 | 63882756 | 63882780 | NM_001271639 | ZNF138 |
| chr7 | 63882756 | 63882780 | NM_001271637 | ZNF138 |
| chr7 | 63882756 | 63882780 | NM_001271649 | ZNF138 |
| chr7 | 63882756 | 63882780 | NM_001271640 | ZNF138 |
| chr7 | 63882756 | 63882780 | NR_073389 | ZNF138 |
| chr7 | 63882756 | 63882780 | NM_001271638 | ZNF138 |
| chr7 | 75449156 | 75449180 | NM_000941 | POR |
| chr7 | 97737806 | 97737830 | NM_001159491 | BRI3 |

FIG. 4C (cont'd)

| chr7 | 97737806 | 97737830 | NM_015395 | TECPR1 |
|---|---|---|---|---|
| chr7 | 97737806 | 97737830 | NM_015379 | BRI3 |
| chr7 | 97764956 | 97764980 | NM_018842 | BAIAP2L1 |
| chr7 | 101696356 | 101696380 | NM_001202546 | CUX1 |
| chr7 | 101696356 | 101696380 | NM_181500 | CUX1 |
| chr7 | 101696356 | 101696380 | NM_001913 | CUX1 |
| chr7 | 101696356 | 101696380 | NM_001202545 | CUX1 |
| chr7 | 101696356 | 101696380 | NM_001202544 | CUX1 |
| chr8 | 1219440 | 1219464 | NR_033895 | LOC286083 |
| chr8 | 1219840 | 1219864 | NR_033895 | LOC286083 |
| chr8 | 10943790 | 10943814 | NM_173683 | XKR6 |
| chr8 | 11788415 | 11788439 | NM_001908 | CTSB |
| chr8 | 11788415 | 11788439 | NM_147781 | CTSB |
| chr8 | 11788415 | 11788439 | NM_147780 | CTSB |
| chr8 | 11788415 | 11788439 | NM_147783 | CTSB |
| chr8 | 11788415 | 11788439 | NM_147782 | CTSB |
| chr8 | 41660415 | 41660439 | NM_001142446 | ANK1 |
| chr8 | 41660415 | 41660439 | NM_000037 | ANK1 |
| chr8 | 41660415 | 41660439 | NM_020475 | ANK1 |
| chr8 | 41660415 | 41660439 | NM_020476 | ANK1 |
| chr8 | 41660415 | 41660439 | NM_020477 | ANK1 |
| chr8 | 83955715 | 83955739 | NM_022133 | SNX16 |
| chr8 | 83955715 | 83955739 | NM_152837 | SNX16 |
| chr8 | 83955715 | 83955739 | NM_152836 | SNX16 |
| chr8 | 108203965 | 108203989 | NM_139166 | ABRA |
| chr8 | 143089065 | 143089089 | NR_039682 | MIR4472-1 |
| chr8 | 143570140 | 143570164 | NM_001702 | BAI1 |
| chr9 | 17897249 | 17897273 | NM_003026 | SH3GL2 |
| chr9 | 27129124 | 27129148 | NM_000459 | TEK |
| chr9 | 95401924 | 95401948 | NM_005392 | PHF2 |
| chr9 | 115367024 | 115367048 | NR_074077 | RGS3 |
| chr9 | 115367024 | 115367048 | NM_144488 | RGS3 |
| chr9 | 115367024 | 115367048 | NM_001276260 | RGS3 |
| chr9 | 115367024 | 115367048 | NM_130795 | RGS3 |
| chr9 | 115367024 | 115367048 | NM_001276261 | RGS3 |
| chr9 | 115367174 | 115367198 | NM_134427 | RGS3 |
| chr9 | 115367174 | 115367198 | NR_074077 | RGS3 |

FIG. 4C (cont'd)

| chr9 | 115367174 | 115367198 | NM_144488 | RGS3 |
|---|---|---|---|---|
| chr9 | 115367174 | 115367198 | NM_001276260 | RGS3 |
| chr9 | 115367174 | 115367198 | NM_130795 | RGS3 |
| chr9 | 115367174 | 115367198 | NM_001276261 | RGS3 |
| chr9 | 130163799 | 130163823 | NM_016035 | COQ4 |
| chr9 | 130163799 | 130163823 | NM_001135947 | URM1 |
| chr9 | 130163799 | 130163823 | NM_001265582 | URM1 |
| chr9 | 130163799 | 130163823 | NR_039815 | MIR2964A |
| chr9 | 130163799 | 130163823 | NR_049743 | URM1 |
| chr9 | 130163799 | 130163823 | NM_015679 | TRUB2 |
| chr9 | 130163799 | 130163823 | NM_030914 | URM1 |
| chr9 | 130163799 | 130163823 | NM_005094 | SLC27A4 |
| chr9 | 130163799 | 130163823 | NR_029837 | MIR219-2 |
| chr9 | 131360549 | 131360573 | NM_199350 | C9orf50 |
| chr9 | 136732624 | 136732648 | NM_000093 | COL5A1 |
| chr9 | 136732624 | 136732648 | NM_001278074 | COL5A1 |
| chrX | 18148117 | 18148141 | NM_153346 | BEND2 |
| chrX | 18148117 | 18148141 | NM_001184767 | BEND2 |
| chrX | 51039392 | 51039416 | NM_153183 | NUDT10 |

FIG. 4D

| DMR No. | Chrom-osome | DMR start | DMR end |
|---|---|---|---|
| 1 | chr1 | 1210985 | 1211009 |
| 2 | chr1 | 3807785 | 3807809 |
| 3 | chr1 | 10518585 | 10518609 |
| 4 | chr1 | 16720135 | 16720159 |
| 5 | chr1 | 26108385 | 26108409 |
| 6 | chr1 | 26544285 | 26544309 |
| 7 | chr1 | 30487535 | 30487559 |
| 8 | chr1 | 54848035 | 54848059 |
| 9 | chr1 | 109447985 | 109448009 |
| 10 | chr1 | 179721435 | 179721459 |
| 11 | chr1 | 226029760 | 226029784 |
| 12 | chr1 | 232915960 | 2322915984 |
| 13 | chr2 | 1768284 | 1768308 |
| 14 | chr2 | 7089784 | 7089808 |
| 15 | chr2 | 25408459 | 25408483 |
| 16 | chr2 | 26263434 | 26263458 |
| 17 | chr2 | 62303059 | 62303083 |
| 18 | chr2 | 86890084 | 86890108 |
| 19 | chr2 | 132511709 | 132511733 |
| 20 | chr2 | 168129384 | 168129408 |
| 21 | chr2 | 204726609 | 204726633 |
| 22 | chr2 | 242197709 | 242197733 |
| 23 | chr3 | 12912595 | 12912619 |
| 24 | chr3 | 49492195 | 49492219 |
| 25 | chr3 | 72309120 | 72309144 |
| 26 | chr3 | 75799770 | 75799794 |
| 27 | chr3 | 75802345 | 75802369 |
| 28 | chr3 | 129756595 | 129756619 |
| 29 | chr4 | 1313454 | 1313478 |
| 30 | chr4 | 7971079 | 7971103 |
| 31 | chr4 | 120547604 | 120547628 |
| 32 | chr5 | 552538 | 552562 |
| 33 | chr5 | 728288 | 728312 |
| 34 | chr5 | 1273013 | 1273037 |

FIG. 4D (cont'd)

| 35 | chr5 | 32481238 | 32481262 |
|---|---|---|---|
| 36 | chr5 | 40823263 | 40823287 |
| 37 | chr5 | 50511663 | 50511687 |
| 38 | chr5 | 114146613 | 114146637 |
| 39 | chr5 | 174261338 | 174261362 |
| 40 | chr5 | 179975988 | 179976012 |
| 41 | chr6 | 287697 | 287721 |
| 42 | chr6 | 3689547 | 3689571 |
| 43 | chr6 | 32610447 | 32610471 |
| 44 | chr6 | 149837197 | 149837221 |
| 45 | chr7 | 1905181 | 1905205 |
| 46 | chr7 | 4740731 | 4740755 |
| 47 | chr7 | 4926256 | 4926280 |
| 38 | chr7 | 5592756 | 5592780 |
| 49 | chr7 | 45164481 | 45164505 |
| 50 | chr7 | 63882756 | 63882780 |
| 51 | chr7 | 75449156 | 75449180 |
| 52 | chr7 | 97737806 | 97737830 |
| 53 | chr7 | 97764956 | 97764980 |
| 54 | chr7 | 101696356 | 101696380 |
| 55 | chr8 | 1219440 | 1219464 |
| 56 | chr8 | 1219840 | 1219864 |
| 57 | chr8 | 10943790 | 10943814 |
| 58 | chr8 | 11788415 | 11788439 |
| 59 | chr8 | 41660415 | 41660439 |
| 60 | chr8 | 83955715 | 83955739 |
| 61 | chr8 | 108203965 | 108203989 |
| 62 | chr8 | 143089065 | 143089089 |
| 63 | chr8 | 143570140 | 143570164 |
| 64 | chr9 | 17897249 | 17897273 |
| 65 | chr9 | 27129124 | 27129148 |
| 66 | chr9 | 95401924 | 95401948 |
| 67 | chr9 | 115367024 | 115367048 |
| 68 | chr9 | 115367174 | 115367198 |
| 69 | chr9 | 130163799 | 130163823 |
| 70 | chr9 | 131360549 | 131360573 |
| 71 | chr9 | 136732624 | 136732648 |

FIG. 4D (cont'd)

| | | | |
|---|---|---|---|
| 72 | chr10 | 46419094 | 46419118 |
| 73 | chr10 | 72497294 | 72497318 |
| 74 | chr10 | 96933094 | 96933118 |
| 75 | chr10 | 125178044 | 125178068 |
| 76 | chr11 | 2192653 | 2192677 |
| 77 | chr11 | 7230253 | 7230277 |
| 78 | chr11 | 26972378 | 26972402 |
| 79 | chr11 | 34159603 | 34159627 |
| 80 | chr11 | 44298178 | 44298202 |
| 81 | chr11 | 63732703 | 63732727 |
| 82 | chr11 | 64733978 | 64734002 |
| 83 | chr11 | 65417228 | 65417252 |
| 84 | chr11 | 76428753 | 76428777 |
| 85 | chr11 | 85945303 | 85945327 |
| 86 | chr12 | 27955362 | 27955386 |
| 87 | chr12 | 30605812 | 30605836 |
| 88 | chr12 | 43731612 | 43731636 |
| 89 | chr12 | 53049112 | 53049136 |
| 90 | chr12 | 53049137 | 53049161 |
| 91 | chr13 | 29008021 | 29008045 |
| 92 | chr13 | 107316571 | 107316595 |
| 93 | chr13 | 107946846 | 107946870 |
| 94 | chr13 | 110103771 | 110103795 |
| 95 | chr13 | 112399146 | 112399170 |
| 96 | chr13 | 112696571 | 112696595 |
| 97 | chr14 | 89274505 | 89274529 |
| 98 | chr14 | 91723780 | 91723804 |
| 99 | chr14 | 99211380 | 99211404 |
| 100 | chr14 | 100245580 | 100245604 |
| 101 | chr14 | 104779380 | 104779404 |
| 102 | chr15 | 87992464 | 87992488 |
| 103 | chr16 | 49298 | 49322 |
| 104 | chr16 | 651573 | 651597 |
| 105 | chr16 | 782698 | 782722 |
| 106 | chr16 | 1055798 | 1055822 |
| 107 | chr16 | 12262398 | 12262422 |
| 108 | chr16 | 23766873 | 23766897 |

FIG. 4D (cont'd)

| 109 | chr16 | 27659398 | 27659422 |
|---|---|---|---|
| 110 | chr16 | 55870173 | 55870197 |
| 111 | chr16 | 55892523 | 55892547 |
| 112 | chr16 | 83973323 | 83973347 |
| 113 | chr16 | 87171298 | 87171322 |
| 114 | chr16 | 87567098 | 87567122 |
| 115 | chr16 | 87824373 | 87824397 |
| 116 | chr17 | 10022007 | 10022031 |
| 117 | chr17 | 23875607 | 23875631 |
| 118 | chr17 | 38963482 | 38963506 |
| 119 | chr17 | 39624932 | 39624956 |
| 120 | chr17 | 41330532 | 41330556 |
| 121 | chr17 | 72908007 | 72908031 |
| 122 | chr17 | 73230682 | 73230706 |
| 123 | chr17 | 76673082 | 76673106 |
| 124 | chr17 | 77659982 | 77660006 |
| 125 | chr18 | 13914891 | 13914915 |
| 126 | chr18 | 43029316 | 43029340 |
| 127 | chr18 | 55514841 | 55514865 |
| 128 | chr18 | 71835416 | 71835440 |
| 129 | chr18 | 73091116 | 73091140 |
| 130 | chr18 | 75265166 | 75265190 |
| 131 | chr18 | 75437691 | 75437715 |
| 132 | chr19 | 833925 | 833949 |
| 133 | chr19 | 961900 | 961924 |
| 134 | chr19 | 2013875 | 2013899 |
| 135 | chr19 | 3928300 | 3928324 |
| 136 | chr19 | 4431975 | 4431999 |
| 137 | chr19 | 8022925 | 8022949 |
| 138 | chr19 | 8229300 | 8229324 |
| 139 | chr19 | 8545700 | 8545724 |
| 140 | chr19 | 16104225 | 16104249 |
| 141 | chr19 | 21234450 | 21234474 |
| 142 | chr19 | 50454525 | 50454549 |
| 143 | chr19 | 52050525 | 52050549 |
| 144 | chr19 | 54750025 | 54750049 |
| 145 | chr19 | 54797050 | 54797074 |

FIG. 4D (cont'd)

| 146 | chr19 | 55707325 | 55707349 |
|---|---|---|---|
| 147 | chr19 | 60689975 | 60689999 |
| 148 | chr20 | 3102643 | 3102667 |
| 149 | chr20 | 17546168 | 17546192 |
| 150 | chr20 | 25229318 | 25229342 |
| 151 | chr20 | 25291443 | 25291467 |
| 152 | chr20 | 29478593 | 29478617 |
| 153 | chr20 | 37253318 | 37253342 |
| 154 | chr20 | 38906193 | 38906217 |
| 155 | chr20 | 56725368 | 56725392 |
| 156 | chr20 | 60514443 | 60514467 |
| 157 | chr20 | 61513618 | 61513642 |
| 158 | chr21 | 44533977 | 44534001 |
| 159 | chr21 | 45790602 | 45790626 |
| 160 | chr21 | 46141227 | 46141251 |
| 161 | chr22 | 19617686 | 19617710 |
| 162 | chr22 | 20636261 | 20636285 |
| 163 | chr22 | 45359436 | 45359460 |
| 164 | chr22 | 48515036 | 48515060 |
| 165 | chr22 | 49221586 | 49221610 |
| 166 | chrX | 18148117 | 18148141 |
| 167 | chrX | 51039392 | 51039416 |

FIG. 7A

| Chromosome | DMR start | DMR end | Gene_region | Gene strand | Gene TSS | Distance to TSS | Overlap with gene | Accession Number | Gene Symbol |
|---|---|---|---|---|---|---|---|---|---|
| chr1 | 26108385 | 26108409 | chr1:26083263:26105580 | - | 26105580 | 2805 | no | NM_001145454 | STMN1 |
| chr1 | 26108385 | 26108409 | chr1:26099193:26105955 | - | 26105955 | 2430 | no | NM_203399 | STMN1 |
| chr1 | 26108385 | 26108409 | chr1:26099193:26105231 | - | 26105231 | 3154 | no | NM_203401 | STMN1 |
| chr1 | 26108385 | 26108409 | chr1:26099193:26105580 | - | 26105580 | 2805 | no | NM_005563 | STMN1 |
| chr1 | 179721435 | 179721459 | chr1:179719308:180042543 | + | 179719309 | 2126 | yes | NM_001205294 | CACNA1E |
| chr1 | 179721435 | 179721459 | chr1:179719308:180042543 | + | 179719309 | 2126 | yes | NM_001205293 | CACNA1E |
| chr1 | 179721435 | 179721459 | chr1:179719308:180042543 | + | 179719309 | 2126 | yes | NM_000721 | CACNA1E |
| chr16 | 23766873 | 23766897 | chr16:23754800:24139433 | + | 23754801 | 12072 | yes | NM_002738 | PRKCB |
| chr16 | 23766873 | 23766897 | chr16:23754800:24139433 | + | 23754801 | 12072 | yes | NM_212535 | PRKCB |
| chr17 | 41330532 | 41330556 | chr17:41327541:41461546 | + | 41327542 | 2990 | yes | NM_016834 | MAPT |
| chr17 | 41330532 | 41330556 | chr17:41327541:41461546 | + | 41327542 | 2990 | yes | NM_016835 | MAPT |
| chr17 | 41330532 | 41330556 | chr17:41327541:41461546 | + | 41327542 | 2990 | yes | NM_001203252 | MAPT |
| chr17 | 41330532 | 41330556 | chr17:41327541:41461546 | + | 41327542 | 2990 | yes | NM_001203251 | MAPT |
| chr17 | 41330532 | 41330556 | chr17:41327541:41461546 | + | 41327542 | 2990 | yes | NM_001123066 | MAPT |
| chr17 | 41330532 | 41330556 | chr17:41327541:41461546 | + | 41327542 | 2990 | yes | NM_001123067 | MAPT |
| chr17 | 41330532 | 41330556 | chr17:41327541:41461546 | + | 41327542 | 2990 | yes | NM_005910 | MAPT |
| chr17 | 41330532 | 41330556 | chr17:41327541:41461546 | + | 41327542 | 2990 | yes | NM_016841 | MAPT |
| chr17 | 41330532 | 41330556 | chr17:41328944:41331960 | + | 41328945 | 1587 | yes | NR_024560 | MAPT-IT1 |
| chr18 | 75265166 | 75265190 | chr18:75256759:75390311 | + | 75256760 | 8406 | yes | NM_172388 | NFATC1 |
| chr18 | 75265166 | 75265190 | chr18:75256759:75390311 | + | 75256760 | 8406 | yes | NM_001278670 | NFATC1 |
| chr18 | 75265166 | 75265190 | chr18:75261261:75390311 | + | 75261262 | 3904 | yes | NM_001278673 | NFATC1 |
| chr18 | 75265166 | 75265190 | chr18:75256759:75390311 | + | 75256760 | 8406 | yes | NM_006162 | NFATC1 |
| chr18 | 75265166 | 75265190 | chr18:75256759:75328990 | + | 75256760 | 8406 | yes | NM_172390 | NFATC1 |
| chr18 | 75265166 | 75265190 | chr18:75261261:75328990 | + | 75261262 | 3904 | yes | NM_001278675 | NFATC1 |

FIG. 7A (cont'd)

| chr18 | 75265166 | 75265190 | chr18:75261261:75390311 | + | 75261262 | 3904 | yes | NM_172389 | NFATC1 |
|---|---|---|---|---|---|---|---|---|---|
| chr18 | 75265166 | 75265190 | chr18:75261261:75390311 | + | 75261262 | 3904 | yes | NM_001278672 | NFATC1 |
| chr18 | 75265166 | 75265190 | chr18:75261261:75390311 | + | 75261262 | 3904 | yes | NM_172387 | NFATC1 |
| chr18 | 75265166 | 75265190 | chr18:75256759:75390311 | + | 75256760 | 8406 | yes | NM_001278669 | NFATC1 |
| chr19 | 2013875 | 2013899 | chr19:1988469:2002243 | - | 2002243 | 11632 | no | NM_199054 | MKNK2 |
| chr19 | 2013875 | 2013899 | chr19:1988469:2002243 | - | 2002243 | 11632 | no | NM_017572 | MKNK2 |
| chr22 | 19617686 | 19617710 | chr22:19601713:19638037 | + | 19601714 | 15972 | yes | NM_005207 | CRKL |

FIG. 7B

| DMR No. | Chromosome | DMR start | DMR end | Gene_region |
|---|---|---|---|---|
| 5 | chr1 | 26108385 | 26108409 | chr1:26083263:26105580 |
| 10 | chr1 | 179721435 | 179721459 | chr1:179719308:180042543 |
| 108 | chr16 | 23766873 | 23766897 | chr16:23754800:24139433 |
| 120 | chr17 | 41330532 | 41330556 | chr17:41327541:41461546 |
| 130 | chr18 | 75265166 | 75265190 | chr18:75256759:75390311 |
| 134 | chr19 | 2013875 | 2013899 | chr19:1988469:2002243 |
| 161 | chr22 | 19617686 | 19617710 | chr22:19601713:19638037 |

FIG. 8C

FISM Cohort
20 training, 19 testing
Accuracy = 94.74%

| Patient ID | Original labels | Prediction |
|---|---|---|
| 1002 | NR | NR |
| 0402 | NR | R |
| 0501 | NR | NR |
| 0502 | R | R |
| 0103 | R | R |
| 0105 | R | R |
| 0205 | NR | NR |
| 0202 | R | R |
| 1301 | NR | NR |
| 1302 | NR | NR |
| 1101 | R | R |
| 0204 | NR | NR |
| 0507 | NR | NR |
| 0802 | R | R |
| 0404 | NR | NR |
| 0108 | R | R |
| 1103 | R | R |
| 0901 | R | R |
| 0701 | R | R |

FIG. 8D

Three validation tests on GFM cohort

| Number of features used | Correct predictions/ Total patients | Accuracy (%) |
|---|---|---|
| 16 | 13/15 | 87% |
| 14 | 15/19 | 79% |
| 6 | 20/28 | 71% |

FIG. 10A

| Chromosome | feature start | feature end | Gene AccessID | Gene Symbol |
|---|---|---|---|---|
| chr19 | 51918525 | 51918549 | NM_001039877 | STRN4 |
| chr19 | 51918525 | 51918549 | NM_013403 | STRN4 |
| chr16 | 1420673 | 1420697 | NM_001114331 | CLCN7 |
| chr16 | 1420673 | 1420697 | NM_001272051 | C16orf91 |
| chr16 | 1420673 | 1420697 | NM_001143980 | CCDC154 |
| chr16 | 1420673 | 1420697 | NM_001287 | CLCN7 |
| chr16 | 1420673 | 1420697 | NM_001193388 | UNKL |
| chr16 | 1420673 | 1420697 | NM_001037125 | UNKL |
| chr11 | 56760878 | 56760902 | NR_027991 | APLNR |
| chr11 | 56760878 | 56760902 | NM_005161 | APLNR |
| chrX | 104952467 | 104952491 | NM_198465 | NRK |
| chr2 | 31311209 | 31311233 | NM_014600 | EHD3 |
| chr14 | 104875530 | 104875554 | NM_015197 | PACS2 |
| chr14 | 104875530 | 104875554 | NM_001100913 | PACS2 |
| chr14 | 104875530 | 104875554 | NM_001243127 | PACS2 |
| chr9 | 136444349 | 136444373 | NM_002957 | RXRA |
| chr4 | 165524529 | 165524553 | NM_001166373 | 1-Mar |
| chr6 | 165911522 | 165911546 | NM_001130690 | PDE10A |
| chr6 | 165911522 | 165911546 | NR_045597 | PDE10A |
| chr16 | 74087198 | 74087222 | NM_024533 | CHST5 |
| chr16 | 74087198 | 74087222 | NM_145254 | TMEM170A |
| chr16 | 74087198 | 74087222 | NM_021615 | CHST6 |
| chr20 | 45966643 | 45966667 | NM_198596 | SULF2 |
| chr20 | 45966643 | 45966667 | NM_001161841 | SULF2 |
| chr19 | 54755500 | 54755524 | NM_015953 | NOSIP |
| chr19 | 54755500 | 54755524 | NM_001270960 | NOSIP |
| chr16 | 2034323 | 2034347 | NM_002528 | NTHL1 |
| chr6 | 163971922 | 163971946 | NM_006775 | QKI |
| chr6 | 163971922 | 163971946 | NM_206853 | QKI |
| chr6 | 163971922 | 163971946 | NM_206855 | QKI |
| chr6 | 163971922 | 163971946 | NM_206854 | QKI |
| chr9 | 125927874 | 125927898 | NM_004789 | LHX2 |
| chr2 | 121294509 | 121294533 | NM_005270 | GLI2 |
| chr7 | 2179731 | 2179755 | NM_003550 | MAD1L1 |
| chr7 | 2179731 | 2179755 | NM_001013836 | MAD1L1 |
| chr7 | 2179731 | 2179755 | NM_001013837 | MAD1L1 |
| chr15 | 29520164 | 29520188 | NM_015995 | KLF13 |
| chr22 | 17543861 | 17543885 | NR_046298 | SLC25A1 |
| chr22 | 17543861 | 17543885 | NM_005984 | SLC25A1 |
| chr22 | 17543861 | 17543885 | NR_033687 | SLC25A1 |

FIG. 10A (cont'd)

| chr22 | 17543861 | 17543885 | NM_001256534 | SLC25A1 |
| --- | --- | --- | --- | --- |
| chr8 | 143089340 | 143089364 | NR_039682 | MIR4472-1 |
| chr1 | 989035 | 989059 | NM_198576 | AGRN |
| chr1 | 989035 | 989059 | NM_001205252 | RNF223 |

FIG. 10B

| DMR No. | Chromo Some | feature start | feature end |
|---|---|---|---|
| 168 | chr1 | 989035 | 989059 |
| 169 | chr2 | 31311209 | 31311233 |
| 170 | chr2 | 121294509 | 121294533 |
| 171 | chr4 | 165524529 | 165524553 |
| 172 | chr6 | 163971922 | 163971946 |
| 173 | chr6 | 165911522 | 165911546 |
| 174 | chr7 | 2179731 | 2179755 |
| 175 | chr8 | 143089340 | 143089364 |
| 176 | chr9 | 125927874 | 125927898 |
| 177 | chr9 | 136444349 | 136444373 |
| 178 | chr11 | 56760878 | 56760902 |
| 179 | chr14 | 104875530 | 104875554 |
| 180 | chr15 | 29520164 | 29520188 |
| 181 | chr16 | 1420673 | 1420697 |
| 182 | chr16 | 2034323 | 2034347 |
| 183 | chr16 | 74087198 | 74087222 |
| 184 | chr19 | 51918525 | 51918549 |
| 185 | chr19 | 54755500 | 54755524 |
| 186 | chr20 | 45966643 | 45966667 |
| 187 | chr22 | 17543861 | 17543885 |
| 188 | chrX | 104952467 | 104952491 |

FIG. 11A

30 training, 9 testing
Accuracy = 100%

| Patient ID | Original label | Prediction |
|---|---|---|
| 1002 | NR | NR |
| 0107 | NR | NR |
| 0402 | NR | NR |
| 1401 | NR | NR |
| 1203 | NR | NR |
| 0401 | R | R |
| 0302 | NR | NR |
| 0701 | R | R |
| 1204 | R | R |

25 training, 14 testing
Accuracy = 92.86%

| Patient ID | Original labels | Prediction |
|---|---|---|
| 1002 | NR | NR |
| 0104 | NR | NR |
| 0402 | NR | NR |
| 0403 | R | NR |
| 0502 | R | R |
| 0103 | R | R |
| 0105 | R | R |
| 1203 | NR | NR |
| 0507 | NR | NR |
| 0401 | R | R |
| 0802 | R | R |
| 1102 | R | R |
| 0106 | R | R |
| 1103 | R | R |

FIG. 11B

6 features, 28 GFM patients
Accuracy = 71%

| Patient ID | Original label | Prediction |
|---|---|---|
| 2A | R | R |
| 3A | R | R |
| 4A | R | R |
| 5A | NR | NR |
| 6A | R | R |
| 7A | NR | R |
| 9A | NR | NR |
| 10A | R | R |
| 11A | NR | R |
| 12A | R | NR |
| 13A | R | R |
| 15A | NR | NR |
| 16A | NR | R |
| 18A | NR | NR |
| 22A | NR | R |
| 23A | R | R |
| 25A | R | R |
| 26A | R | R |
| 27A | NR | NR |
| 30A | NR | NR |
| 32A | NR | R |
| 33A | R | R |
| 34A | NR | R |
| 35A | NR | R |
| 36A | NR | NR |
| 37A | NR | NR |
| 39A | NR | NR |
| 41A | R | R |

14 features, 19 GFM patients
Accuracy = 79%

| Patient ID | Original label | Prediction |
|---|---|---|
| 2A | R | NR |
| 4A | R | R |
| 5A | NR | NR |
| 6A | R | R |
| 9A | NR | NR |
| 11A | NR | NR |
| 12A | R | NR |
| 16A | NR | NR |
| 18A | NR | NR |
| 26A | R | R |
| 27A | NR | NR |
| 30A | NR | NR |
| 32A | NR | R |
| 33A | R | NR |
| 35A | NR | NR |
| 36A | NR | NR |
| 37A | NR | NR |
| 38A | NR | NR |
| 41A | R | R |

16 features, 15 GFM patients
Accuracy = 87%

| Patient ID | Original label | Prediction |
|---|---|---|
| 2A | R | R |
| 4A | R | R |
| 5A | NR | NR |
| 6A | R | R |
| 9A | NR | NR |
| 11A | NR | NR |
| 12A | R | NR |
| 18A | NR | NR |
| 26A | R | R |
| 27A | NR | NR |
| 30A | NR | NR |
| 32A | NR | R |
| 36A | NR | NR |
| 37A | NR | NR |
| 39A | NR | NR |

FIG.18

| Ref Seq ID | Gene Symbol | log2 Fold Change | log2 Counts per Million | Likelihood Ratio | p-value |
|---|---|---|---|---|---|
| NR_001564 | XIST | -9.446575108 | 7.884341471 | 68.90669754 | 1.03E-16 |
| NM_003294 | TPSAB1 | -4.231795275 | 4.444287608 | 18.617531 | 1.60E-05 |
| NM_002704 | PPBP | -3.17310722 | 7.375155132 | 18.23362777 | 1.95398E-05 |
| NM_001765 | CD1C | 5.471097784 | 5.021349834 | 16.44069701 | 5.02E-05 |
| NR_033667 | GYG2P1 | 6.351361434 | -0.684296509 | 16.4011056 | 5.12553E-05 |
| NM_001190452 | MTRNR2L1 | 6.494431805 | 6.244987921 | 16.40071441 | 5.13E-05 |
| NM_018086 | FIGN | 8.662228813 | 1.384916219 | 16.2972438 | 5.41426E-05 |
| NM_002125 | HLA-DRB5 | 1.968138458 | 8.634964559 | 15.07651932 | 1.03E-04 |
| NM_001003693 | LY6G6F | -3.523950364 | 3.218434848 | 14.28238017 | 0.000157331 |
| NM_170776 | GPR97 | -2.778269036 | 6.011889525 | 13.61167622 | 0.000224783 |
| NM_005181 | CA3 | 3.246983578 | 6.20906237 | 13.2965888 | 0.000265889 |
| NR_033841 | LOC200772 | -4.644829875 | 2.655493336 | 13.22836584 | 0.000275744 |
| NM_014243 | ADAMTS3 | 3.25679353 | 2.571807147 | 13.16203851 | 0.000285678 |
| NM_000600 | IL6 | 4.31675611 | 4.5789161 | 13.13001014 | 2.91E-04 |
| NM_005353 | ITGAD | 3.660346684 | 1.284633586 | 12.95028492 | 0.000319873 |
| NM_198682 | GYPE | 2.776991696 | 4.368039072 | 12.4657022 | 4.14E-04 |
| NM_002619 | PF4 | -3.41598203 | 5.869137777 | 12.33334924 | 0.000444937 |
| NM_153183 | NUDT10 | -3.31285648 | 2.507554532 | 11.98600467 | 5.36E-04 |
| NM_002612 | PDK4 | -2.375972161 | 5.989908813 | 11.98384226 | 5.37E-04 |
| NM_001001132 | ITSN1 | 2.05780554 | 4.433208584 | 11.96408384 | 5.42E-04 |
| NM_001958 | EEF1A2 | -5.213096361 | 3.561305162 | 11.85571754 | 5.75E-04 |
| NM_000212 | ITGB3 | -2.716289707 | 5.542921546 | 11.66527388 | 6.37E-04 |
| NM_178313 | SPTBN1 | -1.911155185 | 4.170838264 | 11.40739656 | 7.32E-04 |
| NM_000502 | EPX | 4.306818323 | 4.093665101 | 11.10906809 | 8.59E-04 |
| NM_024577 | SH3TC2 | 3.024417691 | 3.789058539 | 11.10379747 | 8.62E-04 |
| NM_004378 | CRABP1 | 5.579554187 | 0.702111069 | 11.04471549 | 8.89E-04 |
| NR_103731 | PDK1 | -3.035050155 | -0.328587728 | 10.86288286 | 9.81E-04 |

FIG. 18 (cont'd)

| | | | | | |
|---|---|---|---|---|---|
| NM_004120 | GBP2 | -1.624916532 | 8.114396613 | 10.74120445 | 0.001047761 |
| NM_024164 | TPSB2 | -3.402012563 | 4.316472777 | 10.73670243 | 1.05E-03 |
| NM_130848 | C5orf20 | 2.993013926 | 3.7718469 | 10.71469982 | 0.001062877 |
| NM_001040274 | SYCP2L | 4.183388843 | 2.38415405 | 10.64844562 | 0.001101635 |
| NM_002164 | IDO1 | 4.808713789 | 1.741137681 | 10.62944724 | 0.00111301 |
| NM_014747 | RIMS3 | 1.998766953 | 3.763716738 | 10.62288825 | 1.12E-03 |
| NM_001256478 | CMPK2 | 2.945359774 | 0.37860978 | 10.56052 | 1.16E-03 |
| NM_021076 | NEFH | 5.282522688 | 0.213548877 | 10.49065995 | 0.001199795 |
| NM_152327 | AK7 | 3.339936591 | 3.096070179 | 10.27145796 | 0.00135104 |
| NM_015444 | TMEM158 | 2.088797839 | 3.481704087 | 10.23895569 | 1.38E-03 |
| NM_173557 | RNF152 | 2.456210944 | 2.370837359 | 10.20289848 | 0.001402201 |
| NM_000236 | LIPC | -3.777933641 | 0.247521987 | 10.1457817 | 1.45E-03 |
| NM_145061 | SKA3 | 4.529050772 | 0.392927028 | 10.02697166 | 1.54E-03 |
| NR_024006 | LINC00950 | 4.905897683 | 0.246930001 | 9.878961556 | 1.67E-03 |
| NM_004235 | KLF4 | 2.070030365 | 9.155478827 | 9.846580008 | 0.001701478 |
| NM_001424 | EMP2 | 3.253340911 | 3.75001803 | 9.846502136 | 1.70E-03 |
| NM_001206482 | ELMO1 | -3.073252458 | 2.386698833 | 9.830756092 | 1.72E-03 |
| NM_001871 | CPB1 | 4.200369435 | -0.20641799 | 9.790150792 | 0.001754491 |
| NM_002122 | HLA-DQA1 | 2.162805468 | 7.41833818 | 9.789440173 | 1.76E-03 |
| NM_002895 | RBL1 | 2.184267171 | 4.253701374 | 9.758246678 | 1.79E-03 |
| NM_138370 | PKDCC | 2.912154881 | 4.0960612 | 9.755051783 | 1.79E-03 |
| NM_003526 | HIST1H2BC | -2.499099292 | 4.163869634 | 9.682052549 | 1.86E-03 |
| NM_001192 | TNFRSF17 | 3.538274199 | 2.130785138 | 9.641453087 | 0.001902347 |
| NM_002928 | RGS16 | 2.261886664 | 5.001200321 | 9.610722587 | 1.93E-03 |
| NM_004925 | AQP3 | 2.129639595 | 6.728477592 | 9.558169224 | 1.99E-03 |
| NR_045494 | CLU | -3.9805497 | -0.562081802 | 9.526398863 | 2.03E-03 |
| NM_152363 | ANKLE1 | 2.869156338 | 1.416379506 | 9.43530157 | 2.13E-03 |
| NM_173814 | PRTG | -4.133530404 | 1.561580536 | 9.421436177 | 0.002144635 |
| NM_001761 | CCNF | 2.104337627 | 6.465319956 | 9.361186549 | 0.002216286 |

FIG. 18 (cont'd)

| | | | | | |
|---|---|---|---|---|---|
| NM_002001 | FCER1A | 2.595092003 | 6.16772672 | 9.352621348 | 0.002226668 |
| NM_024913 | CPED1 | 3.711506951 | 1.909230362 | 9.343981519 | 0.002237189 |
| NM_000174 | GP9 | -2.457688593 | 3.436047735 | 9.335428847 | 0.002247655 |
| NM_006076 | AGFG2 | 2.196388699 | 4.777616052 | 9.331185261 | 0.002252866 |
| NM_001160008 | NRG1 | 4.60469613 | 0.180635581 | 9.323934747 | 0.002261798 |
| NM_001140 | ALOX15 | 4.530585433 | -0.233677233 | 9.259889138 | 0.002342272 |
| NR_073062 | MCU | -3.15013019 | 0.038120637 | 9.24243899 | 0.002364698 |
| NM_203459 | CAMSAP2 | 2.074013676 | 2.786015514 | 9.228132076 | 0.002383247 |
| NR_045129 | TXLNG2P | 3.317797033 | 2.006753775 | 9.21341339 | 0.002402483 |
| NR_024075 | EMR4P | 2.438672347 | 3.382754632 | 9.192568602 | 0.002429997 |
| NM_001011724 | HNRNPA1L2 | -4.04621602 | -1.324662475 | 9.127619806 | 0.002517791 |
| NM_025107 | MYCT1 | -2.544159214 | 4.718519863 | 9.122677449 | 0.002524602 |
| NM_001030059 | PPAPDC1A | 3.128561912 | 3.002557975 | 9.081453875 | 0.002582147 |
| NM_001199622 | NCOA7 | -2.496433605 | 2.452498662 | 8.9956967 | 0.002706161 |
| NM_005077 | TLE1 | 2.301288006 | 4.959142612 | 8.987298532 | 0.002718626 |
| NM_001252 | CD70 | 2.849312079 | 3.655437549 | 8.967932571 | 0.002747593 |
| NM_001897 | CSPG4 | 3.104266195 | 1.108329278 | 8.967444993 | 0.002748327 |
| NM_002855 | PVRL1 | 1.949745096 | 5.761610192 | 8.893877038 | 0.002861285 |
| NM_016155 | MMP17 | 2.273683805 | 5.146159493 | 8.861657421 | 0.00291223 |
| NM_000474 | TWIST1 | 5.683362042 | 3.32708906 | 8.835708183 | 0.00295393 |
| NM_207582 | ERVFRD-1 | -2.963155903 | 1.740364533 | 8.817321667 | 0.002983843 |
| NM_002098 | GUCA1B | 2.120552478 | 2.679358373 | 8.786748849 | 0.003034265 |
| NM_021732 | AVPI1 | 1.596732909 | 4.332176793 | 8.729900952 | 0.003130335 |
| NM_000575 | IL1A | -4.220798542 | 1.750733488 | 8.670935827 | 0.003233251 |
| NR_040535 | LOC100506472 | 3.087261067 | 0.57399138 | 8.61573165 | 0.003332719 |
| NR_002798 | NAPSB | 1.958758659 | 6.291563204 | 8.422496564 | 0.003706066 |
| NM_032307 | C9orf64 | 2.24666753 | 3.962219508 | 8.414441601 | 0.003722521 |
| NM_015656 | KIF26A | 2.756305049 | 5.955568699 | 8.413802822 | 0.003723829 |
| NM_174977 | SEC14L4 | 2.593999479 | 3.067915567 | 8.411986067 | 0.003727552 |

FIG. 18 (cont'd)

| | | | | | |
|---|---|---|---|---|---|
| NM_001166292 | PTCH2 | 3.748651698 | 1.048532261 | 8.377043593 | 0.0037999 |
| NM_001013257 | BCAM | 2.524513197 | 3.051274362 | 8.328766144 | 0.003902215 |
| NM_022468 | MMP25 | -1.496113541 | 5.142923208 | 8.24495459 | 0.004086543 |
| NM_020163 | SEMA3G | 3.442883066 | 2.395685069 | 8.220197596 | 0.004142669 |
| NM_025179 | PLXNA2 | 1.710888643 | 3.85948347 | 8.216348487 | 0.004151465 |
| NM_000067 | CA2 | 2.171611355 | 10.35822291 | 8.174318239 | 0.004248764 |
| NM_144770 | RBM11 | -2.394143859 | 1.569453233 | 8.137553593 | 0.004335774 |
| NM_004443 | EPHB3 | 3.83543422 | 2.961797421 | 8.108140346 | 0.004406691 |
| NR_026752 | CROCCP2 | 1.475224549 | 6.824508983 | 8.099871833 | 0.004426839 |
| NM_148674 | SMC1B | 4.040286216 | 2.283872639 | 8.068634934 | 0.004503803 |
| NM_013381 | TRHDE | 3.68032773 | 1.14931617 | 8.035371785 | 0.004587259 |
| NR_002830 | GEMIN8P4 | 1.977613368 | 2.390751661 | 7.993127241 | 0.004695524 |
| NM_001007544 | C1orf186 | -3.197451317 | 4.803485376 | 7.959987569 | 0.004782274 |
| NM_181536 | PKD1L3 | 3.102339997 | 1.884405003 | 7.951531317 | 0.004804671 |
| NM_002615 | SERPINF1 | 1.853872468 | 4.299814257 | 7.947820288 | 0.004814533 |
| NM_000877 | IL1R1 | 1.841543803 | 6.161038029 | 7.886668749 | 0.004980051 |
| NM_005304 | FFAR3 | -3.091006825 | 1.190799334 | 7.881577446 | 0.00499409 |
| NM_052941 | GBP4 | -1.473139383 | 6.77587264 | 7.871243075 | 0.005022711 |
| NR_003099 | ZNF273 | -2.553254973 | -0.537818725 | 7.854869412 | 0.005068401 |
| NR_015377 | LOC654433 | 3.23901664 | 2.945993864 | 7.835075725 | 0.005124201 |
| NM_024761 | MOB3B | 1.888850658 | 4.981928669 | 7.832486701 | 0.005131545 |
| NM_002198 | IRF1 | -1.311826486 | 9.121149429 | 7.819979851 | 0.005167177 |
| NM_001008708 | CHAC2 | 2.196184823 | 3.760361703 | 7.807443486 | 0.005203146 |
| NM_173804 | TMEM86B | 1.365850881 | 5.678187845 | 7.774490013 | 0.005298917 |
| NM_144720 | JAKMIP1 | 4.745877524 | -0.291826556 | 7.746105361 | 0.00538285 |
| NM_006486 | FBLN1 | 2.488614071 | 0.912228672 | 7.731187947 | 0.005427503 |
| NR_002947 | TCAM1P | 3.59452324 | 2.358157848 | 7.720228191 | 0.005460549 |
| NM_021246 | LY6G6D | -2.875376634 | 2.239351118 | 7.706501692 | 0.005502228 |
| NM_014398 | LAMP3 | 2.590463157 | 1.968083244 | 7.705995817 | 0.00550377 |

FIG. 18 (cont'd)

| | | | | | |
|---|---|---|---|---|---|
| NM_017436 | A4GALT | 2.397255726 | 5.544180386 | 7.70100694 | 0.005519003 |
| NM_005792 | MPHOSPH6 | 1.50899848 | 5.699842485 | 7.67755478 | 0.005591188 |
| NM_003071 | HLTF | 2.273754709 | 3.2922734 | 7.599615776 | 0.005838074 |
| NM_012217 | TPSD1 | -2.895740138 | 3.311025238 | 7.590556625 | 0.005867483 |
| NM_005347 | HSPA5 | -1.802527268 | 12.18837836 | 7.565261319 | 0.005950403 |
| NM_001988 | EVPL | 2.488058347 | 4.020881566 | 7.516071165 | 0.006115091 |
| NM_022835 | PLEKHG2 | 1.536878221 | 7.085340337 | 7.512903348 | 0.006125855 |
| NM_176894 | P2RY13 | -1.881784161 | 6.815861893 | 7.49748096 | 0.006178535 |
| NM_001014985 | GLTPD2 | 2.628532544 | 0.738826002 | 7.449879627 | 0.006344069 |
| NM_152259 | TICRR | 1.952957128 | 5.098495143 | 7.448847516 | 0.006347708 |
| NM_018027 | FRMD4A | 1.75000683 | 5.436680121 | 7.431719919 | 0.006408406 |
| NM_145296 | CADM4 | 2.249405208 | 1.555709165 | 7.421798676 | 0.006443837 |
| NM_003155 | STC1 | 4.188695246 | 1.775700713 | 7.41736261 | 0.006459743 |
| NM_001168214 | C3orf80 | -2.703379248 | 4.178320478 | 7.400395383 | 0.006520954 |
| NM_001145306 | CDK6 | -2.395802925 | 1.376379722 | 7.356474426 | 0.006682169 |
| NM_001001891 | ANO7 | -2.774211773 | 2.861188561 | 7.338387175 | 0.006749737 |
| NM_000602 | SERPINE1 | -1.966333707 | 4.757279184 | 7.33266575 | 0.006771256 |
| NM_000321 | RB1 | 1.066496642 | 7.074996546 | 7.326141492 | 0.006795879 |
| NM_006419 | CXCL13 | 4.958020206 | 1.274790946 | 7.312929768 | 0.006846022 |
| NM_002061 | GCLM | 1.867590076 | 6.310021378 | 7.309513223 | 0.00685905 |
| NM_033504 | TMEM54 | 4.764242987 | -0.767325726 | 7.308527288 | 0.006862815 |
| NM_001547 | IFIT2 | -1.715495793 | 6.478956721 | 7.247976226 | 0.007098097 |
| NM_032608 | MYO18B | 4.273412379 | 2.946517476 | 7.235822024 | 0.007146308 |
| NM_030622 | CYP2S1 | 1.894851425 | 4.356385404 | 7.217222706 | 0.007220734 |
| NM_001264573 | KIF18B | 2.19488526 | 1.979611301 | 7.20025819 | 0.007289309 |
| NM_004360 | CDH1 | 2.126362784 | 6.29307478 | 7.192338367 | 0.007321551 |
| NM_020853 | KIAA1467 | 1.578734553 | 4.628147659 | 7.186394221 | 0.007345845 |
| NM_032832 | LRP11 | 2.375997311 | 3.70039615 | 7.182107154 | 0.007363418 |
| NM_004668 | MGAM | -2.10855623 | 3.393154785 | 7.181539043 | 0.00736575 |

FIG. 18 (cont'd)

| | | | | | |
|---|---|---|---|---|---|
| NM_025004 | CCDC15 | 2.168796608 | 3.795232394 | 7.169245774 | 0.007416395 |
| NM_001129993 | KIAA1841 | 2.438592875 | 2.041293289 | 7.162254137 | 0.007445357 |
| NM_000014 | A2M | 3.453481358 | 4.709011403 | 7.161561732 | 0.007448232 |
| NM_001882 | CRHBP | -2.797483912 | 5.683821699 | 7.147094929 | 0.007508551 |
| NM_001256182 | ANKRD11 | -4.366785422 | -0.360170588 | 7.13863322 | 0.007544064 |
| NM_005688 | ABCC5 | 1.798598482 | 6.27369296 | 7.105415231 | 0.007685142 |
| NM_000214 | JAG1 | -1.429921229 | 6.046882487 | 7.087294261 | 0.007763237 |
| NM_021067 | GINS1 | 1.939036663 | 4.815885374 | 7.076982918 | 0.007808037 |
| NM_005980 | S100P | -1.956548904 | 5.978467045 | 7.075178229 | 0.007815905 |
| NM_017644 | KLHL24 | -1.267524525 | 7.286841291 | 7.064210735 | 0.007863895 |
| NM_173354 | SIK1 | 1.623743944 | 8.158446099 | 7.043255425 | 0.007956428 |
| NM_152432 | ARHGAP42 | 2.350873174 | 1.767591825 | 7.030113049 | 0.008015029 |
| NM_006563 | KLF1 | 1.871769339 | 8.021215326 | 7.014501301 | 0.008085215 |
| NM_005242 | F2RL1 | -2.269153006 | 4.185299515 | 7.013687187 | 0.008088892 |
| NM_001113203 | NACA | -1.897446095 | 4.544986063 | 7.007310949 | 0.008117752 |
| NM_001099270 | ZBTB34 | -1.131743099 | 6.672558344 | 7.007249956 | 0.008118028 |
| NR_033909 | ECRP | 1.996241623 | 3.962763163 | 6.998201609 | 0.008159164 |
| NM_006778 | TRIM10 | 2.017236017 | 4.603848637 | 6.990360738 | 0.008194984 |
| NM_015474 | SAMHD1 | 1.4609654 | 7.609914771 | 6.97968921 | 0.008243992 |
| NM_031299 | CDCA3 | 1.887135092 | 5.357771063 | 6.978694993 | 0.008248574 |
| NM_005766 | FARP1 | 2.012733841 | 1.698055864 | 6.955983762 | 0.008353935 |
| NM_025190 | ANKRD36B | -1.809637903 | 2.222071705 | 6.927933096 | 0.00848597 |
| NM_001853 | COL9A3 | -2.830592177 | 3.787637058 | 6.922487165 | 0.008511851 |
| NM_014840 | NUAK1 | 2.680044049 | 1.338783926 | 6.917416561 | 0.008536021 |
| NR_103560 | GSN-AS1 | -3.042120604 | 1.024328265 | 6.893650748 | 0.008650243 |
| NM_006644 | HSPH1 | 1.36674921 | 7.151785873 | 6.814060641 | 0.009044287 |
| NM_014657 | TTI1 | 1.313735299 | 5.389626782 | 6.807809788 | 0.009076002 |
| NM_000274 | OAT | 1.47317235 | 5.546671439 | 6.79516503 | 0.009140507 |
| NM_144970 | CXorf38 | -1.013719033 | 6.640835472 | 6.787440501 | 0.009180144 |

FIG. 18 (cont'd)

| | | | | | |
|---|---|---|---|---|---|
| NM_004528 | MGST3 | 1.24996499 | 7.639600326 | 6.775608256 | 0.009241199 |
| NM_206922 | CRIP3 | 2.971062822 | 2.491103316 | 6.77552984 | 0.009241605 |
| NM_021158 | TRIB3 | -1.299609224 | 5.523165724 | 6.773636983 | 0.009251412 |
| NM_022450 | RHBDF1 | -1.896836522 | 3.112838891 | 6.771939522 | 0.009260215 |
| NR_003291 | ANKRD18DP | -2.630465517 | -0.319448638 | 6.769686049 | 0.009271914 |
| NM_001001548 | CD36 | 1.623962886 | 7.928131982 | 6.76103885 | 0.00931695 |
| NM_015896 | ZMYND10 | 1.768539483 | 1.852196888 | 6.75317818 | 0.009358085 |
| NM_031966 | CCNB1 | 1.58026125 | 7.377927998 | 6.740331668 | 0.00942571 |
| NM_001271686 | RAB3IL1 | 2.779657088 | 2.37834745 | 6.73791341 | 0.009438496 |
| NM_007147 | ZNF175 | 1.47480052 | 4.580835394 | 6.721481792 | 0.009525845 |
| NM_002010 | FGF9 | 3.811066753 | 1.072852294 | 6.701475727 | 0.009633315 |
| NM_004998 | MYO1E | 2.001584694 | 3.568468213 | 6.698837761 | 0.009647578 |
| NM_005603 | ATP8B1 | 2.832895735 | 1.126024761 | 6.667818746 | 0.009816926 |
| NM_020440 | PTGFRN | 2.132100701 | 2.945781218 | 6.64674262 | 0.009933727 |
| NM_001001712 | LCN10 | -3.187002005 | 2.132911501 | 6.637796661 | 0.009983734 |
| NM_033102 | SLC45A3 | -1.571117833 | 5.278928913 | 6.636068757 | 0.009993422 |
| NM_152308 | RMI2 | 1.852078912 | 4.865126823 | 6.617315282 | 0.010099196 |
| NM_004932 | CDH6 | 3.303459438 | 3.673924969 | 6.598139254 | 0.01020854 |
| NM_004454 | ETV5 | -1.967655886 | 3.21490685 | 6.596538784 | 0.010217721 |
| NM_006682 | FGL2 | 1.844386155 | 7.858270925 | 6.595908857 | 0.010221336 |
| NR_103837 | FBXL4 | -2.533934349 | 0.283260098 | 6.573058715 | 0.010353387 |
| NM_001114120 | DEPDC1 | 2.637560484 | 1.929211321 | 6.544769274 | 0.010519297 |
| NM_032818 | ARHGEF39 | 1.63861114 | 4.341456873 | 6.529504174 | 0.010609953 |
| NM_001101676 | SAMD12 | -1.944877787 | 1.715698422 | 6.51747014 | 0.010681985 |
| NM_198573 | ENHO | 3.570090595 | 3.999433014 | 6.50189942 | 0.010775931 |
| NM_178191 | ATPIF1 | 1.434096836 | 5.30539133 | 6.496351358 | 0.01080961 |
| NR_037195 | LINC00607 | 4.114775131 | 0.096320218 | 6.462669497 | 0.011016402 |
| NM_001099221 | TIFAB | 3.26554121 | 2.379341668 | 6.42602667 | 0.011245988 |
| NM_001127208 | TET2 | 1.06555163 | 6.129337444 | 6.41260701 | 0.011331293 |

FIG. 18 (cont'd)

| | | | | | |
|---|---|---|---|---|---|
| NM_145238 | ZSCAN20 | 2.266280969 | 1.697706164 | 6.406285055 | 0.011371709 |
| NM_013401 | RAB3IL1 | 2.71973401 | 2.149293779 | 6.400079616 | 0.011411525 |
| NM_014400 | LYPD3 | 2.190359521 | 3.526319937 | 6.388438909 | 0.0114866 |
| NM_016653 | ZAK | 1.358507697 | 4.440329523 | 6.385879185 | 0.011503177 |
| NM_007117 | TRH | -2.858106397 | 4.359071515 | 6.385035522 | 0.011508646 |
| NM_152701 | ABCA13 | -2.57140726 | 3.603501319 | 6.384350064 | 0.011513091 |
| NM_054027 | ANKH | 1.295279511 | 6.864458499 | 6.354422222 | 0.011708907 |
| NM_005211 | CSF1R | 1.820823785 | 7.443732074 | 6.324383065 | 0.011908891 |
| NM_033125 | SLC22A16 | 1.480671393 | 6.089737222 | 6.316929111 | 0.011959056 |
| NM_173584 | EFCAB4A | -1.630921485 | 3.724472581 | 6.31594075 | 0.011965724 |
| NM_145236 | B3GNT7 | 1.502406835 | 4.479186524 | 6.288969756 | 0.012149165 |
| NM_003679 | KMO | 2.000342149 | 2.001607079 | 6.283202189 | 0.012188766 |
| NR_033997 | RNF144A-AS1 | 2.834165013 | 0.777122716 | 6.272493521 | 0.012262646 |
| NR_002330 | ST7-AS1 | -1.430259499 | 2.633061227 | 6.267765624 | 0.01229541 |
| NM_001725 | BPI | -1.91982707 | 7.757283478 | 6.256533911 | 0.012373606 |
| NM_020689 | SLC24A3 | -1.955128848 | 2.736864417 | 6.212399754 | 0.012685854 |
| NM_004612 | TGFBR1 | -1.886649757 | 1.693291348 | 6.207550063 | 0.012720656 |
| NM_006379 | SEMA3C | 1.984005006 | 2.993190867 | 6.207451963 | 0.012721361 |
| NM_153615 | RGL4 | -1.259190455 | 5.93457718 | 6.160960505 | 0.013060027 |
| NM_022338 | C11orf24 | 1.38058594 | 4.508156451 | 6.159979228 | 0.013067274 |
| NM_014441 | SIGLEC9 | 2.047940821 | 3.057786398 | 6.1321947 | 0.013274199 |
| NM_014452 | TNFRSF21 | 1.785877795 | 6.11845818 | 6.129423046 | 0.013295025 |
| NM_031215 | CABLES2 | 1.148381082 | 4.937164281 | 6.119016308 | 0.01337352 |
| NM_005480 | TROAP | 1.606747473 | 6.270734702 | 6.111210082 | 0.013432713 |
| NR_001446 | ANXA2P3 | 1.426983458 | 4.663417714 | 6.086860882 | 0.013619084 |
| NM_018186 | C1orf112 | 1.519663263 | 4.676496361 | 6.080890441 | 0.013665187 |
| NM_001017420 | ESCO2 | 1.657432202 | 5.384310322 | 6.052641891 | 0.013885506 |
| NM_031310 | PLVAP | 2.132654113 | 3.654533915 | 6.039087266 | 0.013992517 |
| NM_001200050 | NPL | 2.07164366 | 0.83920133 | 6.027821859 | 0.0140821 |

FIG. 18 (cont'd)

| | | | | | |
|---|---|---|---|---|---|
| NM_002863 | PYGL | -1.675163265 | 1.506988064 | 6.0227571 | 0.014122567 |
| NM_001781 | CD69 | -1.48896706 | 8.591638037 | 6.010794806 | 0.014218622 |
| NM_014945 | ABLIM3 | -2.222247572 | 2.789710729 | 6.005964962 | 0.014257594 |
| NM_003512 | HIST1H2AC | -1.730075257 | 4.483557834 | 5.99928556 | 0.014311673 |
| NR_033368 | GRIK1-AS2 | 3.47045834 | -0.623155884 | 5.985860616 | 0.014421005 |
| NM_001763 | CD1A | 3.183861788 | 1.516064536 | 5.970016212 | 0.014551147 |
| NM_000057 | BLM | 1.223370751 | 5.431208179 | 5.958766321 | 0.014644285 |
| NM_001326 | CSTF3 | 1.597739182 | 4.54021363 | 5.956032102 | 0.014667014 |
| NR_024451 | JHDM1D-AS1 | 1.409930248 | 4.03926849 | 5.945888865 | 0.014751651 |
| NM_178496 | MB21D2 | 1.850208939 | 3.307910323 | 5.944866999 | 0.014760205 |
| NM_003258 | TK1 | 1.475201712 | 7.489802827 | 5.934357449 | 0.014848482 |
| NM_000165 | GJA1 | -2.106037978 | 3.798172025 | 5.930805479 | 0.01487844 |
| NM_015393 | PARM1 | 1.997173048 | 2.344799283 | 5.920980402 | 0.014961631 |
| NM_000229 | LCAT | 1.705550929 | 3.784392943 | 5.918024494 | 0.014986753 |
| NR_038236 | LINC00968 | 2.099397192 | 1.716586865 | 5.904270044 | 0.015104224 |
| NM_020685 | C3orf14 | 2.952299548 | 1.356232696 | 5.900798721 | 0.01513402 |
| NM_001678 | ATP1B2 | 1.89066885 | 6.057902224 | 5.894082995 | 0.015191838 |
| NM_019556 | MOSPD1 | 1.240282693 | 5.358171602 | 5.891847127 | 0.015211137 |
| NM_001037984 | SLC38A10 | 1.386161103 | 6.376268244 | 5.885271123 | 0.015268047 |
| NM_032638 | GATA2 | -2.994517393 | -0.088936305 | 5.865715276 | 0.015438584 |
| NR_036536 | SNHG4 | -1.509844245 | 3.239876898 | 5.850089966 | 0.015576255 |
| NM_024556 | FAM118B | 1.594958006 | 4.092543363 | 5.823315917 | 0.015815103 |
| NM_005894 | CD5L | 3.0018403 | 3.777751941 | 5.804229241 | 0.015987674 |
| NM_002998 | SDC2 | 2.97527484 | 6.196394503 | 5.8028964 | 0.015999797 |
| NM_004163 | RAB27B | -1.958847102 | 4.830025292 | 5.79562225 | 0.016066128 |
| NM_013388 | PREB | 1.141420246 | 6.318133933 | 5.792117275 | 0.016098189 |
| NR_027504 | MST1P2 | 1.794703912 | 2.476569478 | 5.744075484 | 0.016544361 |
| NM_000552 | VWF | -1.483875348 | 4.721117652 | 5.740312377 | 0.016579844 |
| NM_001159280 | ADAL | 1.743367876 | 2.98094779 | 5.72979478 | 0.016679432 |

FIG. 18 (cont'd)

| | | | | | |
|---|---|---|---|---|---|
| NM_007280 | OIP5 | 1.732823949 | 4.604510144 | 5.7165634 | 0.016805593 |
| NM_001010862 | SPIN3 | 1.743226103 | 2.735700661 | 5.697080685 | 0.016993154 |
| NM_152487 | TMEM56 | 2.426596035 | 0.816398023 | 5.688857048 | 0.017072971 |
| NM_006733 | CENPI | 1.765961449 | 3.541976181 | 5.682151831 | 0.017138336 |
| NR_024469 | LOC100130987 | -2.659022025 | -0.263250623 | 5.681158205 | 0.017148044 |
| NM_021920 | SCT | 3.230598996 | 0.758163013 | 5.679804552 | 0.017161279 |
| NR_038222 | PROSER2-AS1 | -3.096996034 | 0.450145652 | 5.676622624 | 0.017192431 |
| NM_031459 | SESN2 | -1.250657856 | 6.664961919 | 5.659544571 | 0.01736063 |
| NM_015660 | GIMAP2 | -1.195153933 | 6.645177216 | 5.648810926 | 0.017467213 |
| NM_000262 | NAGA | 1.129638497 | 7.340997394 | 5.647127173 | 0.017483993 |
| NM_006942 | SOX15 | 1.677093444 | 3.11576911 | 5.642857999 | 0.017526614 |
| NM_001146694 | KDM4C | 2.94499484 | -0.078954433 | 5.638037283 | 0.017574871 |
| NR_038895 | DLGAP1-AS3 | 2.693736742 | 0.635765889 | 5.633610246 | 0.017619308 |
| NM_012326 | MAPRE3 | 1.341973711 | 2.968492409 | 5.5948867 | 0.018012976 |
| NM_002099 | GYPA | 1.814935792 | 9.24935102 | 5.592089488 | 0.018041762 |
| NM_006617 | NES | 3.920639744 | 1.284623213 | 5.589422709 | 0.01806925 |
| NM_139245 | PPM1L | -1.229862704 | 3.726404601 | 5.539756661 | 0.018589167 |
| NM_031866 | FZD8 | 3.032840638 | 0.816332165 | 5.537001074 | 0.018618462 |
| NM_017633 | FAM46A | -1.273520256 | 8.376177052 | 5.53543477 | 0.018635135 |
| NM_003437 | ZNF136 | -1.084530493 | 5.499053649 | 5.512440373 | 0.018881684 |
| NM_001243177 | ALDOA | 2.539876217 | 0.180514824 | 5.509368447 | 0.018914876 |
| NM_007038 | ADAMTS5 | 2.644906873 | 1.81759087 | 5.492729234 | 0.019095711 |
| NM_006520 | DYNLT3 | -1.227475299 | 5.419302532 | 5.487487305 | 0.01915305 |
| NM_199334 | THRA | -1.265944019 | 4.104947408 | 5.486554373 | 0.019163274 |
| NM_004111 | FEN1 | 1.25770591 | 7.237885152 | 5.483806866 | 0.019193415 |
| NM_173689 | CRB2 | 2.137205035 | 0.956953119 | 5.474485401 | 0.019296041 |
| NM_024057 | NUP37 | 1.239000404 | 5.545608354 | 5.462905662 | 0.01942432 |
| NM_001143978 | ZCCHC18 | -2.350209717 | 0.883848116 | 5.462235202 | 0.019431774 |
| NR_003133 | GBP1P1 | -2.114328717 | 1.914178207 | 5.451307268 | 0.01955369 |

FIG. 18 (cont'd)

| | | | | | |
|---|---|---|---|---|---|
| NM_138961 | ESAM | -1.708202775 | 4.574887983 | 5.445659918 | 0.019617003 |
| NM_017924 | C14orf119 | 1.301933912 | 5.495747418 | 5.442400518 | 0.019653641 |
| NM_018602 | DNAJA4 | 2.042510004 | 2.676923972 | 5.437760941 | 0.019705915 |
| NM_014028 | OSTM1 | 1.053234086 | 5.325878013 | 5.435654539 | 0.019729695 |
| NM_001466 | FZD2 | 2.073681886 | 4.349882186 | 5.427266641 | 0.019824685 |
| NM_006635 | ZNF460 | -1.306823192 | 3.483963631 | 5.423911595 | 0.019862812 |
| NM_021979 | HSPA2 | 1.989229657 | 2.899715558 | 5.406333336 | 0.020063817 |
| NM_012099 | CD3EAP | 2.018222141 | 1.560816998 | 5.405998863 | 0.020067662 |
| NM_018121 | FAM178A | 1.23452991 | 4.80102826 | 5.405514575 | 0.02007323 |
| NM_006502 | POLH | 1.54538635 | 5.198895024 | 5.389731305 | 0.02025559 |
| NM_001992 | F2R | -1.456627139 | 5.144027738 | 5.38906789 | 0.020263292 |
| NM_015140 | TTLL12 | 1.324428605 | 6.856803958 | 5.385505684 | 0.020304703 |
| NM_001001671 | MAP3K15 | -2.400486515 | 1.102516178 | 5.377706851 | 0.020395669 |
| NM_032752 | ZNF496 | -1.122325832 | 5.12728079 | 5.349650005 | 0.020726431 |
| NR_026761 | LINC00467 | 1.737810839 | 2.150260087 | 5.341657075 | 0.020821671 |
| NM_001145176 | SHISA7 | 2.20066339 | 3.12545465 | 5.336941676 | 0.020878071 |
| NM_182915 | STEAP3 | 1.759145659 | 1.83154344 | 5.313262904 | 0.021163683 |
| NR_103791 | LOC100506328 | 2.601229993 | 1.44703026 | 5.313067954 | 0.021166052 |
| NM_001010854 | TTC7B | -1.331546571 | 4.819091244 | 5.295553554 | 0.021379935 |
| NM_003890 | FCGBP | 1.972813868 | 3.463259117 | 5.292322834 | 0.021419632 |
| NM_001080527 | MYO7B | 1.689383189 | 3.315014692 | 5.292163715 | 0.021421589 |
| NM_003253 | TIAM1 | 1.466058482 | 4.557843565 | 5.290613715 | 0.021440663 |
| NM_006522 | WNT6 | 2.958641741 | 0.306515264 | 5.289571766 | 0.021453495 |
| NM_001972 | ELANE | -1.808479821 | 9.090554015 | 5.28594519 | 0.02149822 |
| NM_005378 | MYCN | -2.164758237 | 5.537532041 | 5.275448195 | 0.021628219 |
| NM_022054 | KCNK13 | 3.318288938 | 1.49475751 | 5.273373411 | 0.02165401 |
| NM_052939 | FCRL3 | 2.342082682 | 2.296459162 | 5.259094546 | 0.021832374 |
| NM_001025266 | C3orf70 | 3.011730496 | 0.945327358 | 5.249552322 | 0.021952418 |
| NM_000889 | ITGB7 | 1.461014132 | 5.026353875 | 5.249362686 | 0.021954811 |

FIG. 18 (cont'd)

| | | | | | |
|---|---|---|---|---|---|
| NM_007022 | CYB561D2 | 1.077489959 | 5.289228909 | 5.237126008 | 0.02210977 |
| NM_080593 | HIST1H2BK | -1.352507098 | 5.621053117 | 5.233175573 | 0.022160038 |
| NM_012310 | KIF4A | 1.455785422 | 5.709997588 | 5.230787486 | 0.022190483 |
| NM_015261 | NCAPD3 | 1.214650419 | 7.099283551 | 5.230687918 | 0.022191754 |
| NM_004613 | TGM2 | 1.31396954 | 5.97710897 | 5.222618069 | 0.022294961 |
| NM_003012 | SFRP1 | 3.53300011 | 1.345589604 | 5.20328314 | 0.022544269 |
| NM_000419 | ITGA2B | -1.489714439 | 7.182952482 | 5.194234176 | 0.022661938 |
| NM_005915 | MCM6 | 1.074368544 | 7.340135446 | 5.189849074 | 0.022719189 |
| NM_178822 | IGSF10 | -2.444901668 | 2.930627085 | 5.183566931 | 0.022801469 |
| NM_025108 | C16orf59 | 1.671423445 | 4.041708556 | 5.177491516 | 0.022881335 |
| NM_001039570 | KREMEN1 | 1.697830715 | 5.157067113 | 5.175370444 | 0.022909286 |
| NM_080388 | S100A16 | -2.438293546 | 4.917364018 | 5.172434257 | 0.022948038 |
| NM_013432 | TONSL | 1.372515348 | 5.972671237 | 5.166191098 | 0.02303066 |
| NM_024631 | MSANTD2 | 1.335425915 | 2.827472785 | 5.164523616 | 0.023052779 |
| NM_207398 | GBP7 | -3.071406407 | -0.163422003 | 5.153691675 | 0.023197005 |
| NM_016539 | SIRT6 | 1.782066 | 0.88337923 | 5.151749084 | 0.02322297 |
| NM_024323 | C19orf57 | 1.880650154 | 3.297196756 | 5.148400368 | 0.023267798 |
| NR_102755 | FLJ31104 | -1.736017219 | 0.467981808 | 5.145838623 | 0.023302153 |
| NM_001365 | DLG4 | -2.817625807 | 0.130398155 | 5.13388177 | 0.023463197 |
| NM_001255 | CDC20 | 1.475122606 | 6.789441607 | 5.132634321 | 0.023480065 |
| NM_001018115 | FANCD2 | 1.321141898 | 4.111754966 | 5.12665152 | 0.023561139 |
| NM_014177 | TIMM21 | 1.213629715 | 5.098993867 | 5.119559177 | 0.023657626 |
| NM_024756 | MMRN2 | 2.836319211 | 1.585492091 | 5.111043814 | 0.023774013 |
| NM_003535 | HIST1H3J | 2.665483381 | 0.620815774 | 5.106348231 | 0.023838445 |
| NR_040079 | LOC399715 | -1.825861567 | -0.067718027 | 5.102236045 | 0.023895021 |
| NM_006093 | PRG3 | 4.159573025 | 2.914069867 | 5.095868602 | 0.0239829 |
| NM_001082 | CYP4F2 | -2.125932728 | 0.912180827 | 5.091530173 | 0.024042968 |
| NM_145859 | PDCD10 | -1.952000457 | 0.338577167 | 5.086787719 | 0.024108809 |
| NM_001080826 | SGK223 | 1.700860304 | 2.797929678 | 5.080832275 | 0.024191755 |

FIG. 18 (cont'd)

| | | | | | |
|---|---|---|---|---|---|
| NM_020233 | ADPRM | -1.015777294 | 5.157444719 | 5.072399975 | 0.024309704 |
| NM_002084 | GPX3 | 1.429973477 | 4.224492041 | 5.055672628 | 0.024545453 |
| NM_006218 | PIK3CA | -1.008565306 | 6.068617712 | 5.049524489 | 0.024632697 |
| NM_018154 | ASF1B | 1.448285117 | 6.608819881 | 5.048819316 | 0.024642725 |
| NM_000265 | NCF1 | -1.06736523 | 5.229572733 | 5.038659355 | 0.024787666 |
| NM_022762 | RMND5B | 1.43719316 | 5.656418289 | 5.037201167 | 0.024808541 |
| NM_014865 | NCAPD2 | 1.268136343 | 7.669041539 | 5.01610751 | 0.025112561 |
| NM_138801 | GALM | 1.318238199 | 3.646996074 | 5.009809657 | 0.025204078 |
| NM_152548 | FAM81B | -3.087203828 | 1.101684778 | 5.008641926 | 0.025221085 |
| NM_015510 | DHRS7B | 1.093774838 | 4.616387516 | 5.007739675 | 0.025234234 |
| NM_002048 | GAS1 | 2.293486984 | 0.944085192 | 4.98582217 | 0.025555839 |
| NM_152637 | METTL7B | 2.488085003 | 4.004728222 | 4.972577565 | 0.025752243 |
| NM_014258 | SYCP2 | 1.889330208 | 4.016013168 | 4.969964394 | 0.025791178 |
| NM_000097 | CPOX | 1.341727431 | 8.319737651 | 4.95899857 | 0.025955234 |
| NM_004557 | NOTCH4 | 1.714730826 | 3.312887635 | 4.954996345 | 0.02601538 |
| NM_181742 | ORC4 | -1.295110507 | 2.357698748 | 4.951220666 | 0.026072254 |
| NM_016577 | RAB6B | 1.572399561 | 6.698942359 | 4.940015699 | 0.026241798 |
| NM_006154 | NEDD4 | -2.24644287 | 0.516794855 | 4.937120863 | 0.026285787 |
| NM_021214 | ABHD17C | 1.541283521 | 4.505870403 | 4.924820738 | 0.026473549 |
| NM_144683 | DHRS13 | 1.3347907 | 7.114488968 | 4.915290969 | 0.026619979 |
| NM_019055 | ROBO4 | -2.239994373 | 4.391499649 | 4.912406566 | 0.026664465 |
| NM_153267 | MAMDC2 | -2.474974829 | 4.487599086 | 4.897438296 | 0.026896566 |
| NM_000148 | FUT1 | 2.375167897 | 2.89359906 | 4.883431324 | 0.027115664 |
| NM_004343 | CALR | -1.044275578 | 10.9854574 | 4.882726406 | 0.027126739 |
| NM_022110 | FKBPL | 1.390732836 | 4.259620859 | 4.873898932 | 0.02726583 |
| NM_001164273 | MGA | 2.368646931 | 0.604011451 | 4.853729603 | 0.027586422 |
| NM_002213 | ITGB5 | -1.541806073 | 3.515886586 | 4.852412483 | 0.027607493 |
| NR_026865 | C7orf13 | 2.656600113 | 1.736559169 | 4.849450263 | 0.027654945 |
| NM_004225 | MFHAS1 | 1.143920968 | 6.644845357 | 4.835710122 | 0.027876158 |

FIG. 18 (cont'd)

| | | | | | |
|---|---|---|---|---|---|
| NM_001040441 | ZBTB8A | -1.641600464 | 3.591277213 | 4.830471534 | 0.027960982 |
| NM_005399 | PRKAB2 | -1.621962131 | 0.719791496 | 4.827490304 | 0.028009375 |
| NM_001271856 | GRASP | 2.714509687 | 0.937413871 | 4.822437744 | 0.028091589 |
| NM_001124758 | SPNS2 | -1.755081992 | 5.338078153 | 4.816962258 | 0.028180969 |
| NM_017613 | DONSON | 1.043716763 | 5.644351964 | 4.815319596 | 0.02820784 |
| NM_001100910 | FAM72B | 1.489842351 | 2.783173035 | 4.802885417 | 0.028412114 |
| NM_012089 | ABCB10 | 1.19847668 | 8.238343923 | 4.798299562 | 0.028487841 |
| NM_004237 | TRIP13 | 1.720421208 | 3.973653719 | 4.798195333 | 0.028489564 |
| NM_007207 | DUSP10 | -1.217868723 | 5.443833377 | 4.796606747 | 0.028515847 |
| NM_181506 | LRRC70 | -1.439233102 | 4.915676171 | 4.793791034 | 0.028562495 |
| NM_001093730 | DYTN | -2.261277271 | 1.509308284 | 4.789964523 | 0.028626016 |
| NM_005615 | RNASE6 | 1.47141527 | 7.782441391 | 4.781895836 | 0.028760441 |
| NM_001134456 | NXPE3 | -2.010876824 | -0.043517657 | 4.772100116 | 0.028924522 |
| NM_023002 | HAPLN4 | 2.954445354 | -0.115851875 | 4.767010237 | 0.029010163 |
| NM_006397 | RNASEH2A | 1.445493595 | 6.097539954 | 4.761251571 | 0.029107375 |
| NM_005529 | HSPG2 | -1.621700285 | 5.728960106 | 4.760704728 | 0.029116624 |
| NM_005306 | FFAR2 | -1.68716404 | 4.761676085 | 4.754541013 | 0.029221085 |
| NM_020843 | SCAPER | -2.431655865 | -0.151983286 | 4.743752412 | 0.029404868 |
| NM_153256 | PROSER2 | -1.083549508 | 4.17867588 | 4.742459345 | 0.029426975 |
| NM_004444 | EPHB4 | 1.343155466 | 4.945359953 | 4.736803169 | 0.029523884 |
| NM_053002 | MED12L | -1.223686801 | 4.627835422 | 4.730874538 | 0.029625818 |
| NM_005723 | TSPAN5 | 1.465774694 | 6.493684542 | 4.719883664 | 0.02981576 |
| NM_001077621 | VPS37D | -2.339610829 | 0.01677276 | 4.719303089 | 0.029825829 |
| NM_007351 | MMRN1 | -1.912755707 | 5.31497372 | 4.717571765 | 0.029855875 |
| NM_012405 | ICMT | 1.443046129 | 5.909928434 | 4.712155345 | 0.029950079 |
| NM_003900 | SQSTM1 | -1.105651282 | 4.73514288 | 4.694513073 | 0.030259072 |
| NM_018248 | NEIL3 | 1.66076774 | 4.280215167 | 4.692040565 | 0.030302641 |
| NM_182922 | HEATR3 | 1.056297906 | 5.097409382 | 4.685924696 | 0.030410692 |
| NM_024596 | MCPH1 | 1.245627067 | 2.58156148 | 4.683057774 | 0.030461481 |

FIG. 18 (cont'd)

| | | | | | |
|---|---|---|---|---|---|
| NM_032730 | RTN4IP1 | 1.328502798 | 3.224166268 | 4.674628207 | 0.030611328 |
| NM_005686 | SOX13 | 1.616248136 | 1.706092968 | 4.669896823 | 0.030695772 |
| NM_052969 | RPL39L | 1.628346279 | 3.532580667 | 4.66312671 | 0.030817024 |
| NM_005061 | RPL3L | 2.562990308 | 2.502649119 | 4.656666028 | 0.0309332 |
| NM_018055 | NODAL | 2.357477517 | -0.21485692 | 4.653940166 | 0.030982353 |
| NM_012202 | GNG3 | 2.061726106 | 0.47190453 | 4.642183468 | 0.031195288 |
| NM_017567 | NAGK | 1.028934274 | 6.976158753 | 4.636390815 | 0.031300764 |
| NR_036500 | FOXN3-AS1 | 1.821131333 | 1.645682417 | 4.630893799 | 0.031401201 |
| NR_026859 | ULK4P3 | -3.282657571 | -0.983063506 | 4.619613903 | 0.031608352 |
| NR_003584 | SNHG8 | -1.059559824 | 4.437208789 | 4.615991987 | 0.031675169 |
| NM_018122 | DARS2 | 1.428060317 | 5.064737765 | 4.613527982 | 0.03172071 |
| NM_018369 | DEPDC1B | 2.267991363 | 1.627444668 | 4.606526329 | 0.031850489 |
| NM_003631 | PARG | 1.310357807 | 3.53940505 | 4.603559051 | 0.031905656 |
| NM_016426 | GTSE1 | 1.287475594 | 5.981045314 | 4.599608651 | 0.031979255 |
| NM_001325 | CSTF2 | 1.063014502 | 4.762155182 | 4.594398935 | 0.032076588 |
| NM_005468 | NAALADL1 | -1.360382771 | 4.646032008 | 4.594179156 | 0.032080701 |
| NM_015670 | SENP3 | 1.120826202 | 4.200114722 | 4.585555193 | 0.032242524 |
| NM_020650 | RCN3 | 1.289964371 | 4.16641813 | 4.574791761 | 0.032445689 |
| NM_001605 | AARS | 1.274891671 | 6.88728837 | 4.573274743 | 0.032474431 |
| NM_000904 | NQO2 | 1.107124377 | 5.950542625 | 4.550783212 | 0.032903692 |
| NM_199420 | POLQ | 1.360655406 | 5.793588558 | 4.531673825 | 0.033273059 |
| NM_002934 | RNASE2 | 1.255911172 | 8.126612992 | 4.520772488 | 0.033485709 |
| NM_020431 | TMEM63C | 1.539517309 | 2.566302001 | 4.504160301 | 0.033812494 |
| NM_001206701 | SP100 | 2.165187107 | -0.563899241 | 4.502222104 | 0.033850838 |
| NR_038826 | LINC00989 | -3.137716693 | 1.43760672 | 4.499530502 | 0.033904161 |
| NM_198098 | AQP1 | 1.602857545 | 5.336734132 | 4.493110905 | 0.034031695 |
| NM_021071 | ART4 | 1.894582116 | 4.047892232 | 4.491699161 | 0.034059808 |
| NM_152755 | CNPY4 | 1.337934657 | 4.162003252 | 4.487849887 | 0.034136586 |
| NR_015379 | UCA1 | 2.176492057 | 2.503180884 | 4.487133072 | 0.034150904 |

FIG. 18 (cont'd)

| | | | | | |
|---|---|---|---|---|---|
| NM_001142725 | ERI2 | 1.549246154 | 4.634068992 | 4.484093998 | 0.034211675 |
| NM_016060 | MED31 | 1.416622976 | 2.847971092 | 4.480999671 | 0.034273668 |
| NM_144682 | SLFN13 | 1.198686322 | 6.456730636 | 4.473671027 | 0.034420962 |
| NM_152421 | FAM69B | -1.42485087 | 5.63308678 | 4.471714944 | 0.034460387 |
| NR_047502 | MANEA-AS1 | -2.19969084 | -0.192893061 | 4.470136324 | 0.03449224 |
| NM_016446 | TMEM8B | 1.94096944 | 1.32549908 | 4.469847537 | 0.03449807 |
| NR_026678 | TMEM79 | 2.270327906 | -0.217783495 | 4.466803972 | 0.034559578 |
| NM_022149 | MAGEF1 | 1.584920512 | 4.911952032 | 4.466767894 | 0.034560308 |
| NM_002755 | MAP2K1 | 1.166805946 | 7.530236621 | 4.466711671 | 0.034561446 |
| NM_020379 | MAN1C1 | 1.515155783 | 3.228301903 | 4.463411607 | 0.034628271 |
| NM_021961 | TEAD1 | 3.209737215 | 0.938667872 | 4.463256593 | 0.034631413 |
| NM_001143676 | SGK1 | 2.527039086 | -0.160180622 | 4.460943316 | 0.034678342 |
| NM_015554 | GLCE | 1.37494659 | 4.223572368 | 4.454715197 | 0.03480502 |
| NM_015634 | KIAA1279 | 1.251155837 | 3.6288315 | 4.453830853 | 0.034823046 |
| NM_198461 | LONRF2 | 2.147229157 | 2.380469385 | 4.446271844 | 0.034977527 |
| NM_001134231 | NT5DC2 | 2.378454347 | -0.384060352 | 4.443417975 | 0.035036037 |
| NM_004852 | ONECUT2 | 2.847200869 | -0.239950452 | 4.433934082 | 0.035231213 |
| NM_001242560 | MAP4K4 | 4.040533999 | -0.633330593 | 4.428386592 | 0.035345905 |
| NM_198219 | ING1 | -1.42047724 | 2.024540571 | 4.426546474 | 0.035384035 |
| NM_206839 | MORF4L1 | -1.618330269 | 1.241809932 | 4.42587175 | 0.035398027 |
| NM_020205 | OTUD7B | 1.536588838 | 4.118981462 | 4.424040887 | 0.035436023 |
| NM_006194 | PAX9 | 3.109096432 | -0.385626509 | 4.413527535 | 0.035655038 |
| NR_026698 | KPNA1 | 1.912540215 | 0.151588366 | 4.394657751 | 0.036051695 |
| NR_002570 | CYP2D7P1 | 1.381006248 | 1.306589596 | 4.390953773 | 0.036130096 |
| NM_001081 | CUBN | -1.451864845 | 2.145916547 | 4.388116008 | 0.036190283 |
| NR_103840 | LINC00539 | -2.255527394 | 0.419432565 | 4.384499871 | 0.036267131 |
| NM_001136273 | ZFP92 | -1.923710864 | 0.796286897 | 4.382565758 | 0.036308303 |
| NM_001199022 | CCP110 | 2.145422038 | -0.300910841 | 4.373932471 | 0.036492682 |
| NM_015049 | TRAK2 | 1.15842752 | 8.650370096 | 4.372559798 | 0.036522088 |

FIG. 18 (cont'd)

| | | | | | |
|---|---|---|---|---|---|
| NM_001905 | CTPS1 | 1.047356893 | 6.226679923 | 4.370133845 | 0.036574119 |
| NM_000594 | TNF | -1.552623256 | 6.495521414 | 4.361563616 | 0.036758551 |
| NM_015939 | TRMT6 | 1.609726023 | 1.599623411 | 4.358974592 | 0.036814459 |
| NM_000173 | GP1BA | -1.19535641 | 4.133301994 | 4.338986311 | 0.037249094 |
| NM_080657 | RSAD2 | 1.546588229 | 7.081512753 | 4.33842286 | 0.037261424 |
| NR_003078 | SNORD110 | 1.73246858 | 0.547493911 | 4.33792777 | 0.037272261 |
| NM_005524 | HES1 | -2.107664885 | 3.080002628 | 4.331847598 | 0.037405622 |
| NM_014326 | DAPK2 | -1.481187816 | 2.418326787 | 4.319992209 | 0.037667095 |
| NM_014176 | UBE2T | 1.285519568 | 5.942326655 | 4.316554774 | 0.037743265 |
| NM_030937 | CCNL2 | 1.716493299 | 0.687051433 | 4.30904468 | 0.037910245 |
| NM_004523 | KIF11 | 1.250797145 | 7.247832942 | 4.307247927 | 0.037950309 |
| NM_033413 | LRRC46 | 1.965870227 | 1.111701956 | 4.306907956 | 0.037957894 |
| NM_004102 | FABP3 | 2.279426953 | 1.363014774 | 4.306063438 | 0.037976745 |
| NR_037709 | TEN1-CDK3 | 1.653848828 | 0.790693233 | 4.304719992 | 0.038006752 |
| NM_020402 | CHRNA10 | 1.991594296 | 0.909875192 | 4.302860642 | 0.038048322 |
| NM_001013699 | H3F3C | -1.185761358 | 8.317788669 | 4.299709181 | 0.038118891 |
| NM_001353 | AKR1C1 | -2.063680536 | 2.450967018 | 4.298319172 | 0.03815006 |
| NM_022061 | MRPL17 | 1.057287847 | 5.176642247 | 4.289732233 | 0.038343204 |
| NM_001080506 | TMEM150C | -2.292146926 | 1.920819932 | 4.288030495 | 0.038381602 |
| NM_198147 | ABHD15 | 1.030151039 | 5.329308807 | 4.286208445 | 0.03842276 |
| NM_001258028 | TKT | -2.138906137 | 0.388886888 | 4.279823274 | 0.038567358 |
| NM_012082 | ZFPM2 | -2.734666148 | 0.067173826 | 4.27731034 | 0.038624422 |
| NM_014222 | NDUFA8 | 1.245530593 | 5.491501515 | 4.265126845 | 0.038902345 |
| NM_207381 | TNFAIP8L3 | 2.898718882 | 0.88503686 | 4.261457095 | 0.038986467 |
| NR_003573 | ANXA2P2 | 1.018259489 | 7.618102824 | 4.261220324 | 0.038991901 |
| NM_017793 | RPP25 | 2.227344039 | 2.868276256 | 4.255708725 | 0.039118622 |
| NM_006681 | NMU | 2.099534624 | 3.513593154 | 4.254425962 | 0.039148177 |
| NM_145059 | FUK | 1.005526523 | 4.665266488 | 4.253428249 | 0.03917118 |
| NM_033393 | FHDC1 | 1.39909013 | 7.285687573 | 4.252192713 | 0.039199687 |

FIG. 18 (cont'd)

| | | | | | |
|---|---|---|---|---|---|
| NM_000479 | AMH | 1.851789917 | 0.182346575 | 4.250648949 | 0.039235335 |
| NM_005332 | HBZ | -2.185171601 | 4.73636643 | 4.248063544 | 0.039295113 |
| NM_003064 | SLPI | -1.494862379 | 4.03220919 | 4.243336516 | 0.039404655 |
| NM_052956 | ACSM1 | -1.463556383 | 1.342095281 | 4.241637723 | 0.0394441 |
| NM_025049 | PIF1 | 1.403639407 | 4.780776354 | 4.238427905 | 0.039518744 |
| NM_001037637 | BTF3 | -1.049729833 | 3.498152937 | 4.237972986 | 0.039529335 |
| NM_024106 | ZNF426 | -1.025347456 | 4.106950666 | 4.235648713 | 0.039583494 |
| NM_001067 | TOP2A | 1.341409674 | 8.381727319 | 4.226941045 | 0.039787086 |
| NM_014181 | LGALSL | -1.696272981 | 3.267909729 | 4.221765036 | 0.039908626 |
| NM_015267 | CUX2 | 2.474967039 | 0.667541839 | 4.219445952 | 0.039963208 |
| NM_001136534 | TMEM233 | 3.443701996 | 2.33010737 | 4.216482257 | 0.040033075 |
| NR_003615 | LOC728554 | 1.395451177 | 3.26698881 | 4.213999461 | 0.040091704 |
| NM_001813 | CENPE | 1.293337655 | 6.350953844 | 4.209014227 | 0.040209698 |
| NR_001544 | NCRNA00185 | 2.666902274 | 0.887667305 | 4.196211634 | 0.040514392 |
| NM_001252079 | USP15 | -1.133943083 | 6.814225397 | 4.196174692 | 0.040515275 |
| NM_000491 | C1QB | 2.392570236 | 5.593469402 | 4.194939137 | 0.040544809 |
| NM_001764 | CD1B | 3.14374852 | 0.988338501 | 4.192156556 | 0.040611405 |
| NR_004845 | LOC644936 | 1.710440222 | 0.679440705 | 4.192098402 | 0.040612798 |
| NM_004260 | RECQL4 | 1.245074687 | 6.903648284 | 4.181375746 | 0.040870511 |
| NM_001198784 | C15orf65 | 2.123863203 | -0.199475591 | 4.172718805 | 0.041079829 |
| NM_032336 | GINS4 | 1.253201152 | 4.625186174 | 4.163012528 | 0.041315858 |
| NM_002945 | RPA1 | 1.015435455 | 7.523833921 | 4.159439553 | 0.041403101 |
| NM_032728 | PPAPDC3 | 1.729909542 | 0.969091314 | 4.153401746 | 0.04155097 |
| NM_024512 | LRRC2 | 1.83219316 | 3.289253066 | 4.149897222 | 0.041637051 |
| NM_001256798 | C20orf112 | -1.321413943 | 2.625167918 | 4.147660604 | 0.041692087 |
| NM_017655 | GIPC2 | 2.147294636 | 1.660109633 | 4.142892464 | 0.041809671 |
| NM_000417 | IL2RA | -2.1551981 | 3.945440092 | 4.140681953 | 0.041864301 |
| NM_024017 | HOXB9 | -4.122641349 | 4.521456714 | 4.14018539 | 0.041876583 |
| NM_007008 | RTN4 | -1.925385698 | 0.153365751 | 4.135829819 | 0.041984478 |

FIG. 18 (cont'd)

| | | | | | |
|---|---|---|---|---|---|
| NM_018396 | METTL2B | 1.260833019 | 3.35956689 | 4.134369967 | 0.042020707 |
| NM_174911 | FAM84B | -1.353862523 | 4.425661789 | 4.126015033 | 0.042228681 |
| NM_015038 | KIAA0754 | -1.284930359 | 2.259649345 | 4.12235053 | 0.04232024 |
| NM_006440 | TXNRD2 | 1.144399108 | 4.540501665 | 4.120893716 | 0.042356697 |
| NM_198557 | RBM43 | -1.023063773 | 4.641098162 | 4.117297824 | 0.042446826 |
| NR_047570 | LOC654433 | 2.333562883 | 3.875867634 | 4.111043183 | 0.042604076 |
| NR_030732 | LOC645638 | 1.673213588 | 1.344243615 | 4.108699915 | 0.042663146 |
| NM_001163 | APBA1 | 1.941492748 | 1.749844002 | 4.10861947 | 0.042665176 |
| NM_182515 | ZNF714 | 1.084541605 | 4.212610286 | 4.104642999 | 0.042765619 |
| NM_002522 | NPTX1 | -3.687081922 | 0.771230893 | 4.098506326 | 0.042921116 |
| NM_017957 | EPN3 | 2.632585267 | 0.808110572 | 4.095568035 | 0.04299578 |
| NM_002689 | POLA2 | 1.177874601 | 5.923529263 | 4.09246594 | 0.043074754 |
| NM_007076 | FICD | -1.192309523 | 2.301263347 | 4.089854552 | 0.043141354 |
| NM_001134338 | RNF24 | -1.930904244 | -0.313143815 | 4.085402277 | 0.043255154 |
| NM_031208 | FAHD1 | 1.287755195 | 4.189427568 | 4.083311442 | 0.043308704 |
| NM_000747 | CHRNB1 | -1.085546734 | 4.172445685 | 4.079731606 | 0.043400552 |
| NM_002030 | FPR3 | 2.239986913 | 1.867509254 | 4.076782528 | 0.043476371 |
| NM_203413 | ELP5 | -1.186221783 | 2.85244207 | 4.075175883 | 0.043517735 |
| NM_003529 | HIST1H3A | -1.713989649 | 1.248027278 | 4.072328018 | 0.043591158 |
| NM_025130 | HKDC1 | 3.314280478 | 0.238785442 | 4.06970087 | 0.043659005 |
| NM_017635 | SUV420H1 | 1.373758532 | 3.858623236 | 4.06747355 | 0.043716614 |
| NM_001134793 | HYLS1 | 2.255643081 | -0.712938392 | 4.061547623 | 0.043870275 |
| NM_016343 | CENPF | 1.25064814 | 7.867303087 | 4.057070436 | 0.043986747 |
| NM_022774 | EXO5 | 1.191398035 | 3.88058292 | 4.056941848 | 0.043990097 |
| NM_001271641 | MTCH1 | -3.002494655 | -0.445276182 | 4.056306407 | 0.044006656 |
| NM_003113 | SP100 | 1.241483799 | 3.023184758 | 4.051292584 | 0.044137537 |
| NM_013247 | HTRA2 | 1.118652067 | 4.739251529 | 4.048160778 | 0.044219497 |
| NM_152677 | ZSCAN4 | 3.463124066 | 0.167406912 | 4.045396666 | 0.044291968 |
| NM_001129820 | SLFN14 | 1.405751114 | 4.941472399 | 4.044490892 | 0.044315744 |

FIG. 18 (cont'd)

| | | | | | |
|---|---|---|---|---|---|
| NM_001164824 | SMIM12 | 1.591975431 | 0.622230649 | 4.040444002 | 0.044422133 |
| NM_020242 | KIF15 | 1.249208816 | 6.253452616 | 4.040132279 | 0.044430339 |
| NM_175617 | MT1E | 1.572192569 | 4.090267797 | 4.039200904 | 0.044454867 |
| NM_012282 | KCNE1L | 2.877910226 | 1.686124198 | 4.035998823 | 0.044539303 |
| NM_017785 | SPDL1 | 1.179428104 | 4.955627492 | 4.03530545 | 0.044557609 |
| NM_005544 | IRS1 | 1.805362633 | 2.205575798 | 4.031079879 | 0.04466934 |
| NM_032023 | RASSF4 | 1.243242079 | 6.953386671 | 4.01795819 | 0.045018184 |
| NM_000677 | ADORA3 | 2.312220728 | 0.581925557 | 4.004567597 | 0.045377135 |
| NM_032777 | GPR124 | 1.093600647 | 5.951134106 | 4.002713216 | 0.045427081 |
| NR_026961 | LOC284837 | 1.884756885 | 3.126896842 | 4.001613184 | 0.045456737 |
| NM_013299 | SAC3D1 | 1.378177836 | 4.40619543 | 4.001226278 | 0.045467173 |
| NM_025216 | WNT10A | 2.380959072 | 1.180338899 | 3.987235014 | 0.045846239 |
| NM_018702 | ADARB2 | -2.427936579 | 1.226539832 | 3.98480295 | 0.045912471 |
| NM_182715 | SYPL1 | -1.128965178 | 2.231255981 | 3.983952907 | 0.045935643 |
| NM_207418 | FAM72D | 1.990295836 | 1.419601675 | 3.983773654 | 0.045940531 |
| NR_033770 | ROCK1P1 | 1.998159753 | 0.540940669 | 3.983484393 | 0.04594842 |
| NM_014777 | URB2 | 1.108530237 | 4.36250684 | 3.982521007 | 0.045974705 |
| NM_032536 | NTNG2 | -1.37363792 | 3.809975811 | 3.979463042 | 0.046058244 |
| NM_000334 | SCN4A | -2.172508129 | -0.171915811 | 3.977103755 | 0.046122804 |
| NR_002738 | SNORD57 | 1.988256605 | 0.364046112 | 3.970857557 | 0.04629419 |
| NM_133475 | ANKRD24 | 1.984896286 | 1.27563816 | 3.964530465 | 0.04646848 |
| NM_005708 | GPC6 | -2.749518503 | 2.199867691 | 3.948948964 | 0.046900652 |
| NM_020546 | ADCY2 | -2.775376208 | 2.831965537 | 3.948467916 | 0.046914062 |
| NM_144590 | ANKRD22 | -1.741817274 | 3.476312029 | 3.9328344 | 0.047352071 |
| NM_015226 | CLEC16A | 1.094458481 | 4.839404834 | 3.928654874 | 0.0474699 |
| NM_152665 | TCTEX1D1 | -1.558012885 | 4.060020714 | 3.928632835 | 0.047470522 |
| NM_024712 | ELMO3 | 1.201550572 | 4.698790004 | 3.928141416 | 0.047484396 |
| NR_027239 | ZNF529 | -1.176398032 | 2.7611552 | 3.926327223 | 0.047535654 |
| NM_017867 | C4orf27 | 1.058454842 | 4.813669078 | 3.925429802 | 0.047561031 |

FIG. 18 (cont'd)

| | | | | | |
|---|---|---|---|---|---|
| NM_005167 | PPM1J | 2.306310318 | 1.693518391 | 3.923998656 | 0.047601531 |
| NM_002206 | ITGA7 | 2.132465579 | 0.077782269 | 3.921053199 | 0.047684998 |
| NM_017425 | SPA17 | 1.443167021 | 2.744544284 | 3.904328766 | 0.048161863 |
| NM_001166579 | AANAT | 2.660948952 | -0.342563677 | 3.902647776 | 0.048210071 |
| NR_033400 | CSNK1G2-AS1 | -2.530810959 | -0.342917026 | 3.900688383 | 0.048266327 |
| NM_000682 | ADRA2B | 2.828002543 | 0.960164024 | 3.898330672 | 0.048334111 |
| NM_178835 | ZNF827 | -1.436949522 | 3.279458067 | 3.896437294 | 0.048388618 |
| NM_152310 | ELOVL3 | 2.388896461 | 1.282482575 | 3.8951426 | 0.048425928 |
| NM_000031 | ALAD | 1.147172946 | 9.005111814 | 3.891229615 | 0.048538874 |
| NM_001267043 | AEBP2 | -1.528966747 | 2.04921695 | 3.890051465 | 0.048572935 |
| NM_015559 | SETBP1 | -1.491336303 | 3.465744771 | 3.888640427 | 0.048613762 |
| NM_015149 | RGL1 | 1.82362204 | 5.004920315 | 3.883870575 | 0.048752042 |
| NM_001006634 | ARHGAP17 | 2.079733393 | -0.328341434 | 3.881435666 | 0.048822792 |
| NM_001444 | FABP5 | 1.312986653 | 3.110852272 | 3.880849669 | 0.048839835 |
| NR_015440 | LINC00982 | -2.745448494 | 0.559426154 | 3.877538792 | 0.048936246 |
| NM_005879 | TRAIP | 1.282950726 | 4.248913945 | 3.876376482 | 0.048970139 |
| NM_002343 | LTF | -2.082021626 | 1.53708959 | 3.869635444 | 0.0491672 |
| NM_177948 | ARMCX3 | -2.116944694 | 0.09447385 | 3.866013895 | 0.049273414 |
| NM_016030 | TRAPPC12 | 1.119272783 | 5.505062768 | 3.862734046 | 0.049369816 |
| NM_001243093 | FYB | -1.589564543 | 1.449638809 | 3.849749214 | 0.049753429 |
| NM_024871 | MAP6D1 | 1.878177775 | 1.437498143 | 3.849479751 | 0.049761424 |
| NM_001935 | DPP4 | 1.702896555 | 2.52090214 | 3.84539313 | 0.049882826 |
| NM_003015 | SFRP5 | 2.140047202 | 1.445716349 | 3.843617604 | 0.04993567 |
| NM_152342 | CDYL2 | -1.078438005 | 3.877586861 | 3.843297116 | 0.049945215 |
| NM_015567 | SLITRK5 | -2.172391194 | 3.733676481 | 3.842994237 | 0.049954237 |
| NR_027626 | CMAHP | -1.341527681 | 2.190350091 | 3.842905188 | 0.04995689 |

FIG. 19

| Target Name | Amplicon Size | Number of CpGs | LPL | RPL | F primer | R Primer | Target Sequence |
|---|---|---|---|---|---|---|---|
| GATA2_US_000 | 398 | 34 | 25 | 26 | aggaagagagAGAAGGGTTTTAGAGAGAAGAGTGG (SEQ ID NO: 1) | cagtaatacgactcactatagggagaaggctCAAAAATAAAAAACACCATTTATTCC (SEQ ID NO: 2) | AGAAGGGCCCCAGAGAGAAGAGTGGGGACGCAAAGGAAAGATGGGCAGGATGGGATGGACAGACTGAGATGGAAAGGCCGACAGGGCTTAGCCGCCAAGCTCGAAGGAAGCGCGGGAGGCCGGGCGCCGGGCGAGGATGGGCTGGGCATGAGCTGCGGGCCGCGGGCAGGGCGGGACACCAAGGCGCGGGCGGTGGTGGCGGGCAGGGGGCTCCGCGCGGGGCTGCGCCGCTGTCCGGGGTAATTTTTCATCTCGGCCGGCTAATCTTTGTTCCCGGCGAAGATAATGAATAGCCAGTCGTTATCTGCCCGGCTCCCGGAGGCTGCCCGAGAATGGGGTTGTACAGGGCTGGGAATTGTTTCCAAAGTGCCGCGGAATAAATGGTGTTCCTTATCTCTG (SEQ ID NO: 3) |
| HOXA5_000 | 490 | 25 | 27 | 25 | aggaagagagTTATTGGTTAGAGATGATTTGATGATG (SEQ ID NO: 4) | cagtaatacgactcactatagggagaaggctTAAATACCTAAACAAAAACCAAACC (SEQ ID NO: 5) | CCACTGGCCAGAGATGATTTGATGATGCCCTTCGGGACTTACTGGCGAGGGACTTAGGCAGAGACGCCCAGACACGAAACGGGGCTCGGCCCAGGGCTCTTTCCTCCCCAGCAGCCCCGCGTCCCGAGGTCGGGGAGCTCAGAGACACTAGCACAGGAGCCCCAGACGCATTCAGGGCGCACC |

FIG. 19 (cont'd)

| | | | | | | | |
|---|---|---|---|---|---|---|---|
| | | | | | | | CCAGAACTCCGGAG CCGGTTTGGGCATC CTTGTGGAGCGGGA CTGGGTGTGTGCAG TGCGCCCCGCTCCA CCGCTGGTATTGGC TGTGTGTGAGGTTTT GTTTTGTTTTGTTTT GTTTTGTTTTGTTTT GTTTTGTTTTGTTTT GTAAGAAATAAATGC ACAGACGCTTGCAA AGCTCCGGGCTCCC CTGAAGCTGCGGAA GCCCCAGATGGGA GCAGGCGGGGAGAA AAGTTGGGGAACAG GCGAGGGCAAGGG GGCAAAGCCGAAGG AGGTTGCAGCGCTG GCCTGGTCCCTGCC CAGGCATCTA (SEQ ID NO: 6) |
| HOXA5 _TSS_0 00 | 308 | 15 | 25 | 24 | aggaagag agTTTAG AGGGGT TTTTTGT TTTTTTT (SEQ ID NO: 7) | cagtaatac gactcacta tagggaga aggctAA CCCCAA ATCTAC CCCTAA ATAC (SEQ ID NO: 8) | TCCAGAGGGGTTTTT TGCTTCCTCCCCCTT CCAACGTCTAAACTG TCCCAGAGAACGCC CATTTCCCCCACTAT TTGTGAGCGCAGGG TGCTCGCAAAGAAG AGGAGGAAGGAGGA AGGCAGGGGAGGG AGAACGGCAAGGAG AGCTCCGCAGGGCT GGGAGAAATGAGAC CAAGAGAGACTGGG AGAGGGCGGCAGAG AAGAGAGGGGGGAC CGAGAGCCGCGTCC CCGCGGTCGCGTGG ATTTAGAAAAGGCT GGCTTTACCATGACT TATGTGCAGCTTGC GCATCCAGGGGTAG ATCTGGGGTT (SEQ ID NO: 9) |
| PRDM8 _TSS_0 01 | 492 | 11 | 25 | 25 | aggaagag agTTTAG TAAAGA GTTAAA | cagtaatac gactcacta tagggaga aggctCT | CCCAGCAAAGAGTT AAAGGGAGGGGACG TGGGCTGTCACGCG TCATTGGGCAGATTA |

FIG. 19 (cont'd)

| | | | | | | GGGAGGGG (SEQ ID NO: 10) | AACAATAAACAACCCCTCAAAAA (SEQ ID NO: 11) | TGTGCAGCAAACAAAAAGTGTGTGTCTGCGTGCCAGTCAGTCACTGCATCGGGTCCATCTGTACAACTCTCTCCGTTTCTCCGTCTCTCTCCCTCCCTCCCTCCCTCCACCCCCCCAATCTTTTCTCCCCATCTCTCCATCTCTCTCTTATCTCTTCAGGAAGAGCCTAAAAGGCGGCAACACCAACACCTCTTGACATGGAAATACACTGATACAATAGGCAAAGGAAACACTCGATTGCATCTTCCCGGTTCCAGGTGGCCTTATTTGGGAGATTCTATACTGACCTTATTCCTGGTAAGTCTATTTGCATTGATGTGGGAGGGGGATGGGAGGAAGACAGTTTGGTGGAAAGAGTAGAACATTTTGTCTTCCGTCTCCTTATTATCCAGAAGAGAGAAAAATAATTCTTGAGGGGCTGTCTACTGCCAG (SEQ ID NO: 12) |
| PRDM8_US_000 | 484 | 28 | 25 | 26 | | aggaagagagTTTTGGGGTATATTTTAGGGTAGG (SEQ ID NO: 13) | cagtaatacgactcactatagggagaaggctCCTAATCATTTTTACCCCATACAAAA (SEQ ID NO: 14) | CTCTGGGGTATATTCCAGGGCAGGCGGATAAGAACCTGGGCCTAGAGCGGGGCACGGAGCTGTGAAACGTTGCGTGGCAAGGCGACCGCACGCGGGCGGGCGCTCCTAGGCTCTTGCCCAGCGGTTATTGTGATGGGCTTGAGGCTCGTGGCGCCTGGCGCTGCGACTCCGACCGCTATTAGCGCGGCGTAGTGAGGACCTTTTGCCGTATTGTTAGGTAGAACTGCATTTTAATGACTGTGTCCCTGCTGTTGCCCGAAGTGACGGG |

FIG. 19 (cont'd)

| | | | | | | | GCGACCTCCCGGCACAATGAAATGCTTGTGTGAAAGAGATTTTTAAAAGGAAGAGAGAAATTGGGGAATAAAACGCTGAATTGAAGGAAATTGAAAAGAGGAGAATAGGATTCCGTTGAAAAGGAGATAAGAGGTTATGGGGTTTTTAAAATGTATTTTAATTTGAAATGAAAAAATCAGGATGTCTACCTTGTATGGGGTAAAAATGACCAGG (SEQ ID NO: 15) |
|---|---|---|---|---|---|---|---|
| PTCH1_US_000 | 408 | 15 | 25 | 25 | aggaagagagGTAATGAGGTAAATTGGGGGTAGTT (SEQ ID NO: 16) | cagtaatacgactcactatagggagaaggctTTCAATAACAAAACCTCTTCCACTC (SEQ ID NO: 17) | GCAATGAGGCAAATTGGGGGCAGCCTCAGCCCTGACCACCCAAGTCGAGCAGGCTTTTACACTGGCTCCTCTTCCCTTTCTTAAAACGTTACAGAAACAAGGCCAATTAGATCCTCAAAGTAATTCATCTCTAAGTATGAAAAAGCAGACCACAGGGGAAGCGGCGGGTGGGGGGTGGGGAGATTAAGATAGCGCTCGTTAGAGCCGAGGCTCCGGAGTGCGTCCTGGAACCCACGGGTAGAATTTACAGGCCGGGACCATTGTCTGAGATGCTGAAAAGTTAACCCATCAAACAGCGGGCGAGGGGGCTCAGGGCACTGAAAGCTCCGGGGATCAATGTTCAAAACGTTTAGGAATTAAGTCAAACTAAGGGATATGGGCCTGAGTGGAAGAGGCTTTGCCACTGAA (SEQ ID NO: 18) |
| PTCH1_DS_000 | 407 | 12 | 25 | 25 | aggaagagagGAGATGTTTTTTGGAGTT | cagtaatacgactcactatagggagaaggctAA | GAGATGCCCTTTGGAGTTGGCTCAGGTTAGGGCAAGGAGGCCAGAGCCTCATGCCC |

FIG. 19 (cont'd)

| | | | | | | | | |
|---|---|---|---|---|---|---|---|---|
| | | | | | GGTTTAG (SEQ ID NO: 19) | TTTCTATTCCCATTAATCCCAAA (SEQ ID NO: 20) | TCACATTGACCCGTCATTGTATGCAGGTGGCCACCAGGAGACATGATCTTGGGCCACACGTTTCTCTTCCATACAGTGCAACTCTCAAAGAAGGATTCAACTGAGCCATCGGCCAGCGCACTCCGCAGCCGGAGGACAGAGTGCTGAGTCAGGGTGTGGGTGGAGGGGCAGGGCGCTCAGGACCGCCAGGTTCCCAGCGGGGTGAGCAGCTGTGAGGAGACTGAGCCCTGCAGCTGGAATGAGGAAGTGGGAGGAGCAGATGGCATCAGAGAGAGGACAGATTCGTTTTGAGCTGGTGGCATTTAAACGCTGGAGAAGGTGTCGACCTGGGATCAATGGGAATAGAAACC (SEQ ID NO: 21) |
| SALL4_001 | 471 | 39 | 29 | 21 | aggaagagagTAATGAGGGTTTATTTAAATGATTTTTGA (SEQ ID NO: 22) | cagtaatacgactcactatagggagaaggctAACACTAAACCCCCAAATCTC (SEQ ID NO: 23) | CAATGAGGGCTTATTTAAATGATCTCTGAGGTCTTGGACCCAGGCCAATCAGCTGTCAGGGCTCATGATAAATCGCAATGCATTATTGATAATAATAATTACTGGGACATGCGCGTTCCGGCCGAAGGGGGGTAAATTTCCCAACTCCAGGAATTTGTGGCGGAGAGGGCAAATAACTGCGGCTCTCCCGGCGCCCCGATGCTCGCACCATGTCGAGGCGCAAGCAGGCGAAACCCCAGCACATCAACTCGGAGGAGGACCAGGGCGAGCAGCAGCCGCAGCAGCAGACCCCGGAGTTTGCAGATGCGGCCCCAGCGGCGCCCGCGGCGGGGGAGCTGG |

FIG. 19 (cont'd)

| | | | | | | | | GTGAGTGGGGCTGG GGCGCCCGCCCGG GGAGGGGAGCTTCC CGGACGTACGCGGG ATCCTCGAGGGCGC AGGCTTCGGGGAGC GGGCGGCGTCCAGC GCAAATTCAGGAGC CGAGATTTGGGGGC TCAGTGCC (SEQ ID NO: 24) |
|---|---|---|---|---|---|---|---|---|
| MAPK DMRS | | | | | | | | |
| STMN1_000 | 460 | 11 | 25 | 25 | aggaagag agGGAG TTGGTT GTGATT ATGGAG TTA (SEQ ID NO: 25) | cagtaatac gactcacta tagggaga aggctAA AACAAC ACCCTA CCCTCT AAAAC (SEQ ID NO: 26) | GGAGCTGGCTGTGA CTATGGAGCCACAC AACGAAGTGGAGAT AGGGCAGTCATCCA GCTTATTTGATCTGT GTAGACAGCTAAAG GAGAGCACTTCAGG CTTCAAAGTCTAGAA GGAATGTCTACACT GATCAAACGGCGGG CCAGGCCGTTGTCA GATCTCCTCTCCTGC CAGAGAGCCCGGCA GCCTTTGTTCATTGT TGGGCTTGAGGCTG CAGGGTTTGTCTCC CACATGGCGCCTCC AAGTTCCACAGCTG CTTTCGAGGCCTGT CCTCGGCCAAAGGG TGTCGTGGGAGAGG TTTGCTTGTTGTCCC CGGTCTCTCTGTTCC CTTTGTCTCCTAATC CTCAAGCACTATGCT CTAACACTCCCTTCT CTATTCAAAACCTGT CTATGAGTCTGCTGT TTTACACATCGATCT CCCTCACTAGACCAT TAGGTCCTAGAGGG CAGGGTGCTGTCTT (SEQ ID NO: 27) |
| CACNAE1_000 | 301 | 13 | 25 | 25 | aggaagag agGTAGT ATTTGG TGGATG | cagtaatac gactcacta tagggaga aggctAC | GCAGCACCTGGTGG ATGGGAAGATTTAGA GAACCGTAGAAGCC GAGTGAGAAGGAG |

FIG. 19 (cont'd)

| | | | | | | GGAAGA TT (SEQ ID NO: 28) | TAAACT TCTCCC TCTCTC CTCTC (SEQ ID NO: 29) | GGCCCAGCTGGGAA ATCCGTAGACTGCC TAGAGGAATATTTGC AGCCGCAGCACACA ACACAATGAGATCTG TCCGCTTTGTGCAG CGCACCGGCAGGCG TGACTGCAGGGACC CGACCCTCCCCCG CCCGAAACCTCCAC CCTAGCTAGATACGT TCAACTCAGGCAAT GGATGGCCTGGGAT CACTCTGTGAGAGT GGAGCAGGGGAGC GGGATGCAGAGAGG AGAGAGGGAGAAGC CCAGC (SEQ ID NO: 30) |
| NFATC _001 | 499 | 21 | 25 | 28 | | aggaagag agTTTGT TGTTGG AAGTAA TGTGTTT A (SEQ ID NO: 31) | cagtaatac gactcacta tagggaga aggctAC TATTAC CATACA CAACTC ATCCCC TA (SEQ ID NO: 32) | CTTGCTGTTGGAAG CAATGTGCTTAGCA GGCCTGGGAAACGC TGCCTCACAGTGGC ACCGGGACGTGGTC AGGCCCGCGGCATG ACAGACAGCAACAG CTTCCCAGACGCCG TTCCCCAACAATCT GCCAGCGAGAAAGA TTTACAAAGGCAAAT AGGATGGCCTCGTC ACAGCGCAAACAAA CGGTATTTAATGTTC CATAAATAAGCACGC CAACGCCTTAATAAG GGTCCTTCGTCCAG CCCGGGGCCCAACC TGGGACATCGTTCC TCAGAGGTACTGGA ATATTCCCCCTGGTC CGACGCACACATCA TTTTAAAGCATCCTT TTTGAATTCTGTTTT CAAGGAATTAAAAAA TATCCAAGTTGTTCA TGGCTAGCTGAGAT CTTCCTTTGAAAAAC ACGACACAGAACTG AAATATTCCAATCTG CCAGGTAACTCCAC |

FIG. 19 (cont'd)

| | | | | | | | | | CCTCCACGGAAACA CCTCTAGAACGTCA GGGGATGAGCTGTG CATGGTAATAGC (SEQ ID NO: 33) |

FIG. 20

| Primer Name | Sequence |
|---|---|
| CXCL4 Fwd | 5' GCGCTGAAGCTGAAGAAGAT 3' (SEQ ID NO: 34) |
| CXCL4 Rvs | 5' TTCAGCGTGGCTATCAGTTG 3' (SEQ ID NO: 35) |
| CXCL7/PPBP Fwd | 5' GCGAAAGGCAAAGAGGAAAGTC 3' (SEQ ID NO: 36) |
| CXCL7/PPBP Rvs | 5' CCTTTCCCGATCACTTCCAAAC 3' (SEQ ID NO: 37) |
| ITGb3 Fwd | 5' GCAGGCATTGTCCAGCCTAA 3' (SEQ ID NO: 38) |
| ITGb3 Rvs | 5' AGTCATCAGCCCCAAAGAGG 3' (SEQ ID NO: 39) |
| RPL19 Fwd | 5' TGGCAAGAAGAAGGTCTGGT 3' (SEQ ID NO: 40) |
| RPL19 Rvs | 5' AAGGTGTTTTTCCGGCATC 3' (SEQ ID NO: 41) |

BIOMARKERS FOR PREDICTING RESPONSIVENESS TO DECITABINE THERAPY

FIELD OF INVENTION

Provided herein is technology relating to predicting a subject's resistance or responsiveness to a decitabine based therapy and particularly, but not exclusively, to methods, compositions, and related uses for predicting a subject's resistance or responsiveness to a decitabine based therapy wherein the subject is diagnosed with chronic myelomonocytic leukemia.

BACKGROUND

Chronic myelomonocytic leukemia (CMML) is a type of leukemia, which are cancers of the blood-forming cells of the bone marrow. In adults, blood cells are formed in the bone marrow, by a process that is known as hematopoiesis. In CMML, there are increased numbers of monocytes and immature blood cells (blasts) in the peripheral blood and bone marrow, as well as abnormal looking cells (dysplasia) in at least one type of blood cell (see, e.g., Foucar K (2009) *Am. J. Clin. Pathol.* 132 (2): 281-9). CMML shows characteristics of a myelodysplastic syndrome (MDS); a disorder that produces abnormal looking blood cells, and a myeloproliferative disorder (MPD); a disorder characterised by the overproduction of blood cells. For this reason CMML was reclassified as a MDS/MPN overlap disorder in 2002 (see, e.g., Vardiman J W, et al., (2002) *Blood* 100 (7): 2292-302).

CMML and MDS are notoriously hard to treat. Given that MDS and MDS/MPN are epigenetically abnormal, it is not surprising that epigenetic-modifying drugs have been successful as therapeutics to treat these disorders, especially since these diseases are resistant to conventional chemotherapies. In particular, the nucleoside analogs azacytidine (AZA) and Decitabine (DAC) are commonly used to treat MDS and CMML (see, e.g., Kantarjian, H., et al., Cancer. 2006; 106(8):1794-1803; Silverman, L. R., et al., *J Clin Oncol.* 2002; 20(10):2429-2440). Despite their utility, only a subset of MDS and CMML patients respond to DAC or AZA. Indeed, only approximately 50% of patients treated with DMT is show a hematological improvement or better, which is required for a survival benefit (see, e.g., Griffiths, E. A., and Gore, S. D. *Semin Hematol.* 2008; 45(1):23-30). Furthermore, as many as six months of treatment may be required for the therapeutic benefit of DMTis to become apparent, thus forcing half of the patients to undergo long treatments before they can be deemed resistant to this therapy. Currently, there are very few means of predicting response vs. resistance for these drugs.

As such, improved methods are needed for predicting a subject's resistance or responsiveness to a decitabine based therapy wherein the subject is diagnosed with chronic myelomonocytic leukemia.

SUMMARY

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (see, e.g., Laird (2010) Nat Rev Genet 11: 191-203).

Analysis of CpG islands has yielded important findings when applied to animal models and human cell lines. For example, Zhang and colleagues found that amplicons from different parts of the same CpG island may have different levels of methylation (see, Zhang et al. (2009) PLoS Genet 5: e1000438). Further, methylation levels were distributed bi-modally between highly methylated and unmethylated sequences, further supporting the binary switch-like pattern of DNA methyltransferase activity (see, Zhang et al. (2009) PLoS Genet 5: e1000438). Analysis of murine tissues in vivo and cell lines in vitro demonstrated that only about 0.3% of high CpG density promoters (HCP, defined as having >7% CpG sequence within a 300 base pair region) were methylated, whereas areas of low CpG density (LCP, defined as having <5% CpG sequence within a 300 base pair region) tended to be frequently methylated in a dynamic tissue-specific pattern (see, e.g., Meissner et al. (2008) Nature 454: 766-70). HCPs include promoters for ubiquitous housekeeping genes and highly regulated developmental genes.

Myelodysplastic syndromes and chronic myelomonocytic leukemia (CMML) are characterized by mutations in epigenetic modifiers and aberrant DNA methylation. DNA methyltransferase inhibitors (DMTis) are used to treat these disorders, but response is highly variable with few means to predict which patients will benefit.

To develop a molecular means of predicting response at diagnosis, experiments conducted during the course of developing embodiments for the present invention examined baseline differences in mutations, DNA methylation, and gene expression in 40 CMML patients responsive and resistant to Decitabine (DAC). It was found that while somatic mutations did not differentiate responders and non-responders, 188 differentially methylated regions (DMRs) at baseline between responders and non-responders using next-generation sequencing were identified (see, FIGS. 4D and 10B). These DMRs were primarily localized to non-promoter regions and overlapped with distal regulatory enhancers. Using the methylation profiles, an epigenetic classifier was developed that accurately predicted DAC response at the time of diagnosis. Transcriptional analysis revealed that gene expression differences also exist at diagnosis between responders and non-responders. Genes up-regulated in responders were enriched in the cell cycle genes, potentially contributing to effective DAC incorporation. Two chemokines overexpressed in non-responders—CXCL4 and CXCL7—were able to block the effect of DAC on normal $CD34^+$ and primary CMML cells in vitro, suggesting their up-regulation contributes to primary DAC resistance.

Accordingly, provided herein is technology relating to predicting a subject's resistance or responsiveness to a decitabine-based therapy and particularly, but not exclusively, to methods, compositions, and related uses for predicting a subject's resistance or responsiveness to a decitabine based therapy wherein the subject is diagnosed with chronic myelomonocytic leukemia. Indeed, provided herein is technology for biomarkers directed toward predicting a subject's (e.g., a subject diagnosed with CMML) responsiveness to a decitabine therapy. Markers were identified in a case-control study by comparing the methylation state of DNA markers from subjects diagnosed with CMML that demonstrated or did not demonstrate a favorable response to decitabine therapy (see, Examples 1-8).

In some embodiments, the technology is related to assessing the presence of and methylation state of one or more of the markers identified herein in a biological sample. These markers comprise one or more differentially methylated regions (DMR) as discussed herein (e.g., one or more of DMR Nos. 1-167) (e.g., one or more of DMR Nos. 168-188), e.g., as provided in FIG. 4D and FIG. 10B, respectively.

The technology provides reagents for detecting a DMR, e.g., in some embodiments are provided a set of oligonucleotides related to one or more DMR (e.g., DMR 1-167 as provided in FIG. 4D, e.g., DMR 168-188 in FIG. 10B). In some embodiments are provided an oligonucleotide comprising a sequence complementary to a chromosomal region having a base in a DMR, e.g., an oligonucleotide sensitive to methylation state of a DMR.

The technology provides various panels of markers, e.g., in some embodiments the marker comprises a chromosomal region within one or more DMR, e.g., DMR 1-167 as provided in FIG. 4D, e.g., DMR 168-188 in FIG. 10B. In addition, embodiments provide a method of analyzing a DMR from FIGS. 4D and 10B that is DMR Nos. 1-188.

Kit embodiments are provided, e.g., a kit comprising a bisulfite reagent; and a control nucleic acid comprising a sequence from a DMR selected from a group consisting of DMR 1-167 (from FIG. 4D) and/or a DMR selected from a group consisting of DMR 168-188 (from FIG. 10B) and having a methylation state associated with a subject who is not responsive to decitabine therapy. In some embodiments, kits comprise a bisulfite reagent and an oligonucleotide as described herein. In some embodiments, kits comprise a bisulfite reagent; and a control nucleic acid comprising a sequence from a DMR selected from a group consisting of DMR 1-167 (from FIG. 4D) and/or DMR 168-188 (from FIG. 10B) and having a methylation state associated with a subject who is responsive to decitabine therapy. Some kit embodiments comprise a sample collector for obtaining a sample from a subject (e.g., a bone marrow sample); reagents for isolating a nucleic acid from the sample; a bisulfite reagent; and an oligonucleotide as described herein.

The technology is related to embodiments of compositions (e.g., reaction mixtures). In some embodiments are provided a composition comprising a nucleic acid comprising a DMR and a bisulfite reagent. Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for a subject's responsiveness to decitabine therapy in a sample obtained from a subject, e.g., a method comprising determining a methylation state of a marker in the sample comprising a base in a DMR that is one or more of DMR 1-167 (from FIG. 4D) and/or one or more of DMR 168-188 (from FIG. 10B); comparing the methylation state of the marker from the subject sample to a methylation state of the marker from a normal control sample from a subject who is not responsive to decitabine therapy; and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMR with a bisulfite reagent to produce a bisulfite-reacted nucleic acid; sequencing the bisulfite-reacted nucleic acid to provide a nucleotide sequence of the bisulfite-reacted nucleic acid; comparing the nucleotide sequence of the bisulfite-reacted nucleic acid with a nucleotide sequence of a nucleic acid comprising the DMR from a subject who is not responsive to decitabine therapy to identify differences in the two sequences; and predicting the subject as likely being responsive to decitabine therapy when a difference is present.

Systems for screening for a subject's (e.g., a subject diagnosed with CMML) responsiveness to decitabine therapy in a sample obtained from a subject are provided by the technology. Exemplary embodiments of systems include, e.g., a system for screening for such a responsiveness in a sample obtained from a subject, the system comprising an analysis component configured to determine the methylation state of a sample, a software component configured to compare the methylation state of the sample with a control sample or a reference sample methylation state recorded in a database, and an alert component configured to alert a user of a decitabine responsiveness-associated methylation state. An alert is determined in some embodiments by a software component that receives the results from multiple assays (e.g., determining the methylation states of multiple markers, e.g., DMR, e.g., as provided in FIG. 4D, e.g., as provided in FIG. 10B) and calculating a value or result to report based on the multiple results. Some embodiments provide a database of weighted parameters associated with each DMR provided herein for use in calculating a value or result and/or an alert to report to a user (e.g., such as a physician, nurse, clinician, etc.).

In some embodiments all results from multiple assays are reported and in some embodiments one or more results are used to provide a score, value, or result based on a composite of one or more results from multiple assays that is indicative of the subject's predicted responsiveness to decitabine therapy.

In some embodiments of systems, a sample comprises a nucleic acid comprising a DMR. In some embodiments the system further comprises a component for isolating a nucleic acid, a component for collecting a sample such as a component for collecting a bone marrow sample. In some embodiments, the system comprises nucleic acid sequences comprising a DMR. In some embodiments the database comprises nucleic acid sequences from subjects who are not responsive to decitabine therapy. Also provided are nucleic acids, e.g., a set of nucleic acids, each nucleic acid having a sequence comprising a DMR. In some embodiments the set of nucleic acids wherein each nucleic acid has a sequence from a subject who is responsive to decitabine therapy. Related system embodiments comprise a set of nucleic acids as described and a database of nucleic acid sequences associated with the set of nucleic acids. Some embodiments further comprise a bisulfite reagent. And, some embodiments further comprise a nucleic acid sequencer.

Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) Mol. Cell. Biol. 14: 7421-7427) and another example involves methylation-sensitive arbitrarily primed PCR (Gonzalgo et al. (1997) Cancer Res. 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR amplification (Singer-Sam et al. (1990) Nucl. Acids Res. 18: 687). In addition, other techniques have been reported that utilize bisulfite treatment of DNA as a starting point for methylation analysis. These include methylation-specific PCR (MSP) (Herman et al. (1992) Proc. Natl. Acad. Sci. USA 93: 9821-9826) and restriction enzyme digestion of PCR products amplified from bisulfite-converted DNA (Sadri and Hornsby (1996) Nucl. Acids Res. 24: 5058-5059; and Xiong and Laird (1997) Nucl. Acids Res. 25: 2532-2534). PCR techniques have been developed for detection of gene mutations (Kuppuswamy et al. (1991) Proc. Natl. Acad. Sci. USA 88: 1143-1147) and quantification of allelic-specific expression (Szabo and Mann (1995) Genes Dev. 9: 3097-3108; and Singer-Sam et al. (1992) PCR Methods Appl. 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361,720; and U.S. Pat. Appl. Pub. Nos. 2012/0122088 and 2012/0122106, incorporated herein by reference).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMR, e.g., DMR 1-167 as provided in FIG. 4D, e.g., DMR 168-188 in FIG. 10B); comparing methylation states (e.g., of one or more DMR, e.g., DMR 1-167 as provided in FIG. 4D, e.g., DMR 168-188 in FIG. 10B); generating standard curves; determining a Ct value; calculating a fraction, frequency, or percentage of methylation (e.g., of one or more DMR, e.g., DMR 1-167 as provided in FIG. 4D, e.g., DMR 168-188 in FIG. 10B); identifying a CpG island; determining a specificity and/or sensitivity of an assay or marker; calculating an ROC curve and an associated AUC; sequence analysis; all as described herein or is known in the art.

In some embodiments, a microprocessor or computer uses methylation state data in an algorithm to predict a site of a cancer.

In some embodiments, a software or hardware component receives the results of multiple assays and determines a single value result to report to a user that indicates a cancer risk based on the results of the multiple assays (e.g., determining the methylation state of multiple DMR, e.g., as provided in FIG. 4D, e.g., as provided in FIG. 10B). Related embodiments calculate a risk factor based on a mathematical combination (e.g., a weighted combination, a linear combination) of the results from multiple assays, e.g., determining the methylation states of multiple markers (such as multiple DMR, e.g., as provided in FIG. 4D, e.g., as provided in FIG. 10B). In some embodiments, the methylation state of a DMR defines a dimension and may have values in a multidimensional space and the coordinate defined by the methylation states of multiple DMR is a result, e.g., to report to a user, e.g., related to a subject's predicted responsiveness to decitabine therapy.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

Accordingly, provided herein is technology related to a method of predicting a subject's (e.g., a subject diagnosed with CMML) responsiveness to a decitabine based therapy, the method comprising assaying a methylation state of a marker in a sample obtained from a subject; and predicting the subject to be responsive to a decitabine based therapy when the methylation state of the marker is different than a methylation state of the marker assayed in a subject that is not responsive to a decitabine based therapy, wherein the marker comprises a base in a differentially methylated region (DMR) selected from a group consisting of DMR 1-167 as provided in FIG. 4D and/or DMR 168-188 in FIG. 10B. Some embodiments provide methods comprising assaying a plurality of markers, e.g., comprising assaying 2 to 11 markers.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density region that is not a promoter. In some embodiments the marker is in a high CpG density promoter.

The technology is not limited by sample type. For example, in some embodiments the sample is a bone marrow sample (e.g., a bone marrow sample comprising bone marrow mononuclear cells), a tissue sample, a blood sample (e.g., plasma, serum, whole blood), an excretion sample, a urine sample, or a stool sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings. It is to be understood that the figures are not necessarily drawn to scale, nor are the objects in the figures necessarily drawn to scale in relationship to one another. The figures are depictions that are intended to bring clarity and understanding to various embodiments of apparatuses, systems, compositions, and methods disclosed herein. Wherever possible, the same reference numbers are used throughout the drawings to refer to the same or like parts. Moreover, it should be appreciated that the drawings are not intended to limit the scope of the present teachings in any way. In addition, some of the figures may be in grey-scale coloring.

FIG. 3: Distinct DNA methylation profiles are associated with recurrent somatic mutations in DNMT3A, TET2, ASXL1, and SRSF2. Volcano plots illustrating the methylation differences between DNMT3A- mutant (A), TET2- mutant (B), ASXL1-mutant (C) or SRSF2-mutant (D) vs. wild-type patients (top panels). Pie charts illustrating the relative proportion of CpG tiles and DMRs annotated to RefSeq promoter, exon, intron and intergenic regions (bottom panels).

FIG. 4A-B: Baseline DNA methylation differences distinguish Decitabine (DAC) responders and non-responders at the time of diagnosis. A. Volcano plot illustrating methylation differences between DAC-sensitive and DAC-resistant patients. Mean methylation difference between the two groups is represented on the x-axis and statistical significance ($-\log 10(\text{p value})$) is on the y-axis. 167 Differentially Methylated Regions (DMRs) with FDR<0.1 and absolute methylation difference ≥25% are indicated by red dots. B. Hiearchical clustering of the patients using the 167 DMRs illustrates the power of these genomic regions in segreggating the patients into non-responders (blue) and responders (red).

FIG. 4C: Complete list of differentially methylated regions (DMRs) between responders and non-responders including chromosome, DMR start, DMR end, Gene Access ID, and Gene Symbol.

FIG. 4D: Complete list of differentially methylated regions (DMR Nos. 1-167) between responders and non-responders including chromosome, DMR start, DMR end, Gene Access ID, and Gene Symbol.

FIG. 7A: Complete list of differentially methylated regions (DMRs) enriched in MAP kinase-pathway.

FIG. 7B: Complete list of differentially methylated regions enriched in MAP kinase-pathway.

FIG. 8A-D: Methylation profiles can be harnessed to classify patients according to Decitabine (DAC) response at diagnosis. A. Heatmap of 21 CpG tiles selected as the SVM classifier predictors. DAC-sensitive patients are indicated by the dark red bar, while the non-responders are labeled by the dark blue bar B. Correspondence analysis (COA) using only the 21 CpG tiles included in the classifier can segreggate the majority of CMML cohort according to response to DAC (responders are represented in dark red and non-responders in dark blue). C. Prediction performance of the SVM classifier trained on 20 randomly selected samples and applied to the remaining 19 samples in the FISM cohort. D. Summary of the prediction performance on the independent validation cohort (GFM) in three scenarios using increasing number of shared features out of the 21 features pre-selected using the FISM cohort.

FIG. 10A: List of CpG regions used in the classifier to predict Decitabine response.

FIG. 10B: List of CpG regions used in the classifier to predict Decitabine response including DMR Nos. 168-188.

FIG. 11A-B: Epigenetic classifier accurately predicts patient response to Decitabine. A. Predictions of the 21-feature SVM classifier on two randomly selected training sets of the FISM cohort, which were trained by the corresponding exclusive testing sets. B. Validations of the SVM classifier on the independent GFM cohort using 6, 14, and 16 out of the 21 features selected from FISM cohort (left, middle, and right panels, respectively).

FIG. 18: Complete list of genes with at least a two-fold change in expression level between Decitabine (DAC) responders and non-responders identified by RNA-seq after applying the cutoff of p value <0.05. Negative log 2 fold-change (-log 2FC) values indicate overexpression in non-responders while positive values indicate overexpression in responders.

FIG. 19: Primers and amplicon sequences for the EpiTYPER MassARRAY validation of ERRBS and the MAPK signaling pathway.

FIG. 20: Primers used in the qRT-PCR validation of the RNA-seq results.

DETAILED DESCRIPTION

Figure 1A:
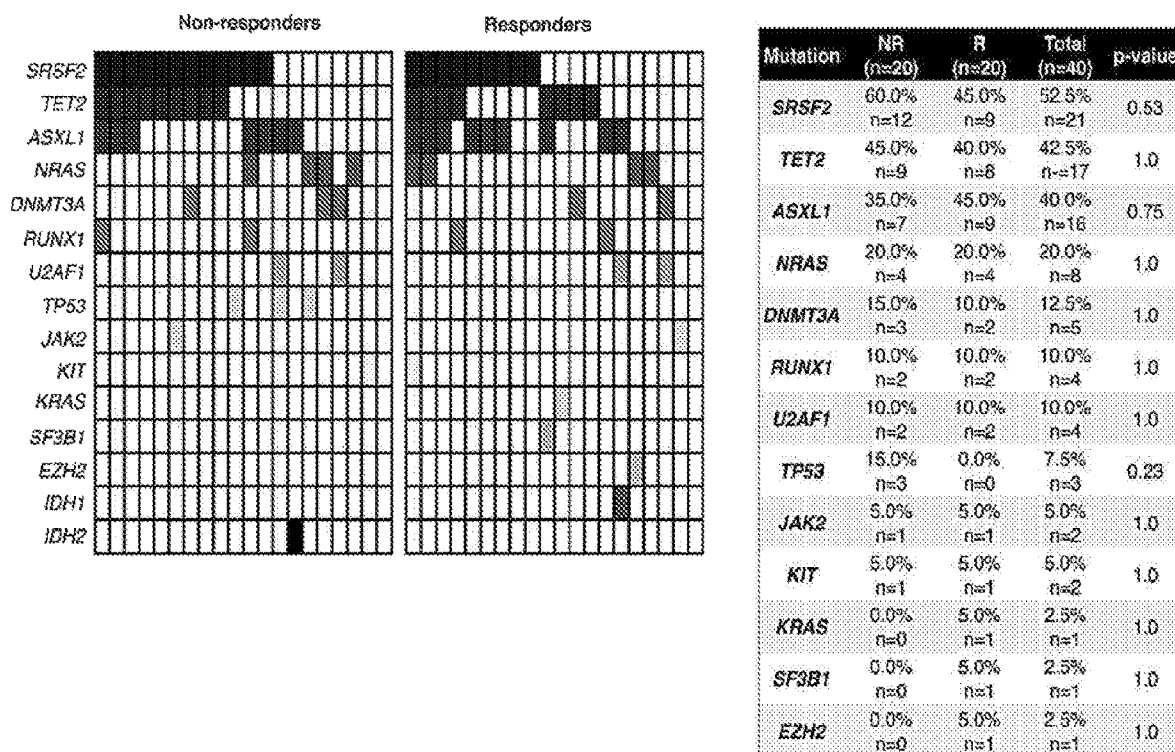
FIG. 1: Somatic mutations in CMML do not correlate with Decitabine response or specific epigenetic clusters. Mutational status of a panel of 15 genes frequently mutated in CMML according to (A) therapeutic response to DAC (left and right panels) or (B) DNA methylation hierarchical clustering.

Provided herein is technology relating to predicting a subject's resistance or responsiveness to a decitabine based therapy and particularly, but not exclusively, to methods, compositions, and related uses for predicting a subject's resistance or responsiveness to a decitabine based therapy wherein the subject is diagnosed with chronic myelomonocytic leukemia.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a subregion of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and polyadenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Amplification of nucleic acids generally refers to the production of multiple copies of a polynucleotide, or a portion of the polynucleotide, typically starting from a small amount of the polynucleotide (e.g., a single polynucleotide molecule, 10 to 100 copies of a polynucleotide molecule, which may or may not be exactly the same), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), Hot-start PCR (see, e.g., U.S. Pat. Nos. 5,773,258 and 5,338,671; each herein incorporated by reference in their entireties), intersequence-specfic PCR, inverse PCR (see, e.g., Triglia, et al et al. (1988) Nucleic Acids Res., 16:8186; herein incorporated by reference in its entirety), ligation-mediated PCR (see, e.g., Guilfoyle, R. et al et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of KB. Mullis U.S. Pat. Nos. 4,683,195, 4,683, 202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons."

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-beta replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics 4:560). Finally, thermostable template-dependant DNA polymerases (e.g., Taq and Pfu DNA polymerases), by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, Hologic, Inc.) and are described, e.g., in U.S. Pat. Nos. 5,846,717, 5,985, 557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124, 246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110, 677, 5,914,230, 5,882,867, and 5,792,614, herein incorporated by reference in their entireties); ligase chain reaction (e.g., Barnay Proc. Natl. Acad. Sci USA 88, 189-93 (1991)); and sandwich hybridization methods (e.g., U.S. Pat. No. 5,288,609, herein incorporated by reference in its entirety).

The term "amplifiable nucleic acid" refers to a nucleic acid that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) *Cell* 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) *J. Mol. Biol.* 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) *Proc. Natl. Acad. Sci. USA* 97: 5237-5242; Salmon and Kaye (1970) *Biochim. Biophys. Acta.* 204: 340-351; Grafstrom (1985) *Nucleic Acids Res.*

13: 2827-2842; Nyce (1986) *Nucleic Acids Res.* 14: 4353-4367; Woodcock (1987) *Biochem. Biophys. Res. Commun.* 145: 888-894).

As used herein, a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such a change in the nucleic acid molecule's nucleotide sequence can result in a nucleic acid molecule in which each methylated nucleotide is modified to a different nucleotide. Such a change in the nucleic acid nucleotide sequence can result in a nucleic acid molecule in which each unmethylated nucleotide is modified to a different nucleotide. Such a change in the nucleic acid nucleotide sequence can result in a nucleic acid molecule in which each of a selected nucleotide which is unmethylated (e.g., each unmethylated cytosine) is modified to a different nucleotide. Use of such a reagent to change the nucleic acid nucleotide sequence can result in a nucleic acid molecule in which each nucleotide that is a methylated nucleotide (e.g., each methylated cytosine) is modified to a different nucleotide. As used herein, use of a reagent that modifies a selected nucleotide refers to a reagent that modifies one nucleotide of the four typically occurring nucleotides in a nucleic acid molecule (C, G, T, and A for DNA and C, G, U, and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

As used herein, the term "bisulfite reagent" refers to a reagent comprising in some embodiments bisulfite, disulfite, hydrogen sulfite, or combinations thereof to distinguish between methylated and unmethylated cytidines, e.g., in CpG dinucleotide sequences.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) *Cancer Research* 57: 594-599.

The term "MethyLight™" refers to the art-recognized fluorescence-based real-time PCR technique described by Eads et al. (1999) *Cancer Res.* 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) *Nucleic Acids Res.* 25: 2529-2531.

The term "MSP" (Methylation-specific PCR) refers to the art-recognized methylation assay described by Herman et al. (1996) *Proc. Natl. Acad. Sci. USA* 93: 9821-9826, and by U.S. Pat. No. 5,786,146.

The term "COBRA" (Combined Bisulfite Restriction Analysis) refers to the art-recognized methylation assay described by Xiong & Laird (1997) *Nucleic Acids Res.* 25: 2532-2534.

The term "MCA" (Methylated CpG Island Amplification) refers to the methylation assay described by Toyota et al. (1999) *Cancer Res.* 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The terms "methylation-specific restriction enzyme" or "methylation-sensitive restriction enzyme" refers to an enzyme that selectively digests a nucleic acid dependent on the methylation state of its recognition site. In the case of a restriction enzyme that specifically cuts if the recognition site is not methylated or is hemimethylated, the cut will not take place or will take place with a significantly reduced efficiency if the recognition site is methylated. In the case of a restriction enzyme that specifically cuts if the recognition site is methylated, the cut will not take place or will take place with a significantly reduced efficiency if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker refers to the percentage of samples (e.g., samples from a subject diagnosed with MDS or CMML) that report a DNA methylation value above a threshold value that distinguishes between responsiveness or non-responsiveness to decitabine therapy. In some embodiments, a positive is defined as a confirmed responsiveness for a subject that reports a DNA methylation value above a threshold value (e.g., the range associated with responsiveness to decitabine therapy), and a false negative is defined as a confirmed non-responsiveness for a subject that reports a DNA methylation value below the threshold value (e.g., the range associated with non-responsiveness to decitabine therapy). The value of sensitivity, therefore, reflects the probability that a DNA methylation measurement for a given marker obtained from a subject diagnosed with MDS or CMML will be in the range of responsiveness-associated measurements. As defined here, the clinical relevance of the calculated sensitivity value represents an estimation of the probability that a given marker would successfully predict a subject's (e.g., a subject diagnosed with MDS or CMML) responsiveness or non-responsiveness to decitabine therapy.

As used herein, the "specificity" of a given marker refers to the percentage of samples (e.g., samples from a subject diagnosed with MDS or CMML) that report a DNA methylation value below a threshold value that distinguishes between responsiveness and non-responsiveness to decitabine therapy. In some embodiments, a negative is defined as a confirmed non-responsive sample that reports a DNA methylation value below the threshold value (e.g., the range associated with non-responsiveness to decitabine therapy) and a false positive is defined as a histology-confirmed non-responsive sample that reports a DNA methylation value above the threshold value (e.g., the range associated with responsiveness to decitabine therapy). The value of specificity, therefore, reflects the probability that a DNA methylation measurement for a given marker obtained from a sample known to be non-responsive to decitabine therapy will be in the range of non-responsive associated measurements. As defined here, the clinical relevance of the calculated specificity value represents an estimation of the probability that a given marker would predict the absence of a clinical condition when applied to a subject (e.g., a subject diagnosed with MDS or CMML).

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) *Signal Detection Theory and ROC Analysis*, Academic Press, New York).

The term "marker", as used herein, refers to a substance (e.g., a nucleic acid or a region of a nucleic acid) that is able to predict a subject's (e.g., a subject diagnosed with MDS or CMML) responsiveness or non-responsiveness to decitabine therapy, e.g., based its methylation state.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, a "remote sample" as used in some contexts relates to a sample indirectly collected from a site that is not the cell, tissue, or organ source of the sample.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Embodiments of the Technology

Chronic myelomonocytic leukemia (CMML) is a myelodysplastic syndrome/myeloproliferative neoplasm (MDS/MPN) overlap syndrome (see, e.g., Nimer, S. D. Blood. 2008; 111(10):4841-4851) that was historically classified within MDS (see, e.g., Ma, X., et al., Cancer. 2007; 109(8): 1536-1542) until 2001 (see, e.g., WHO, I. 2008. World Health Organization classification of tumors of haematopoietic and lymphoid tissues Lyon: International Agency for Cancer (IARC). 439 pp.). CMML shares many characteristics with MDS, including dysplasia in one or more myeloid cell lineages and increased risk of transformation to acute myeloid leukemia (AML). However, a distinguishing feature of CMML is the presence of persistent peripheral monocytosis ($>1\times10^9$/L). CMML can be subdivided into two subtypes on the basis of blast count: CMML-1 with <10% bone marrow blasts, and CMML-2, which has between 10-19% blasts.

Substantial epigenetic abnormalities have been described in MDS and MDS/MPN. Mutations in epigenetic modifying enzymes are highly prevalent in these disorders, including those responsible for DNA methylation and demethylation—DNA methyltransferase 3A (DNMT3A) (see, e.g., Walter, M. J., et al., Leukemia. 2011; 25(7):1153-1158) and ten eleven translocation 2 (TET2) (see, e.g., Tefferi, A., et al., Leukemia. 2009; 23(7):1343-1345; Abdel-Wahab, O., et al., Blood. 2009; 114(1):144-147), respectively—as well as those involved in histone modifying complexes—additional sex combs-like 1 (ASXL1) (see, e.g., Gelsi-Boyer, V., et al., Br J Haematol. 2009; 145(6):788-800) and enhancer of zestes 2 (EZH2) (see, e.g., Khan, S. N., et al., Leukemia. 2013; 27(6):1301-1309; Ernst, T., et al., Nat Genet. 2010; 42(8):722-726; Makishima, H., et al., Leukemia. 2010; 24(10):1799-1804; Nikoloski, G., et al., Nat Genet. 2010; 42(8):665-667). Although the precise mechanisms through which these mutations drive the aberrant epigenetic changes observed in MDS are still not completely understood, it has been shown that MDS and MDS/MPN are characterized by DNA hypermethylation that increases with disease severity (see, e.g., FIGueroa, M. E., et al., Blood. 2009; 114(16): 3448-3458; Jiang, Y., et al., Blood. 2009; 113(6):1315-1325).

MDS and MDS/MPN are resistant to conventional chemotherapies, however; epigenetic-modifying drugs can be used successfully as therapeutics to treat these disorders. In particular, the nucleoside analogs azacytidine (AZA) and Decitabine (DAC) are commonly used to treat MDS and CMML (see, e.g., Kantarjian, H., et al., Cancer. 2006; 106(8):1794-1803; Silverman, L. R., et al., J Clin Oncol. 2002; 20(10):2429-2440). Both AZA and DAC are DNA methyltransferase inhibitors (DMTis), and while their precise mechanism of action in treating MDS and MDS/MPN remains a point of controversy, they are incorporated into DNA during S phase where they covalently trap DNA methyltransferases and target them for proteasome degradation (see, e.g., Ghoshal, K., et al., Mol Cell Biol. 2005; 25(11):4727-4741; Patel, K., et al., Nucleic Acids Res. 2010; 38(13):4313-4324). DMTis can also cause DNA damage (see, e.g., Palii, S. S., et al., Mol Cell Biol. 2008; 28(2): 752-771), and because AZA is mostly incorporated into RNA, it may have additional effects on RNA processing and translation (see, e.g., Cihak, A., et al., Acta Biol Med Ger. 1974; 33(5-6):859-865). Despite their utility, only a subset of MDS and CMML patients respond to DAC or AZA. Only approximately 50% of patients treated with DMTis show a hematological improvement or better, which is required for a survival benefit (see, e.g., Griffiths, E. A., and Gore, S. D. Semin Hematol. 2008; 45(1):23-30). Furthermore, as many as six months of treatment may be required for the therapeutic benefit of DMTis to become apparent, thus forcing half of the patients to undergo long treatments before they can be deemed resistant to this therapy. Currently, there are very few means of predicting response vs. resistance, and even this is exclusive to AZA (see, e.g., Itzykson, R., et al., Blood. 2011; 117(2):403-411). Additionally, few alternative treatments exist for patients who fail to respond to DMTis. Therefore, it is critical that we better understand the molecular profiles associated with sensitivity and resistance to DMTis in order to improve risk-stratification strategies as well as shed light on mechanisms of resistance.

While it has been suggested that reversal of methylation and/or transcript re-expression of certain loci was associated with clinical response to DMTis (see, e.g., Gore, S. D., et al., Cancer Res. 2006; 66(12):6361-6369; Daskalakis, M., et al., Blood. 2002; 100(8):2957-2964; Kantarjian, H., et al., Blood. 2007; 109(1):52-57; Mund, C., et al., Cancer Res. 2005; 65(16):7086-7090; Blum, W., et al., J Clin Oncol. 2007; 25(25):3884-3891; Shen, L., et al., J Clin Oncol. 2010; 28(4):605-613; Folio, M. Y., et al., Proc Natl Acad Sci USA. 2009; 106(39):16811-16816), epigenetic studies to date have failed to identify any strong correlation between response to these agents and the presence of specific baseline DNA methylation profiles (see, e.g., Daskalakis, M., et al., Blood. 2002; 100(8):2957-2964; Blum, W., et al., J Clin Oncol. 2007; 25(25):3884-3891; Shen, L., et al., J Clin Oncol. 2010; 28(4):605-613; Issa, J. P., et al., Blood. 2004; 103(5):1635-1640; Fandy, T. E., et al., Blood. 2009; 114 (13):2764-2773).

In experiments conducted during the course of developing embodiments for the present invention, it was hypothesized that this lack of correlation was due to the promoter-centric nature of assays employed over the last decade and that methylation differences associated with potential for therapeutic response were likely present in these patients at diagnosis at promoter-distal and intergenic regulatory regions. Such experiments demonstrated the identification of DNA methylation and expression differences in diagnostic bone marrow specimens from a cohort of CMML patients treated with DAC. These differences, detected through the use of genome-wide next-generation sequencing assays, reveal underlying biological differences between these two groups of patients and point to a novel mechanism of resistance to DMTis.

Accordingly, provided herein is technology relating to predicting a subject's resistance or responsiveness to a DNA methyltransferase inhibitor (e.g., decitabine, azacitidine) based therapy and particularly, but not exclusively, to methods, compositions, and related uses for predicting a subject's resistance or responsiveness to a decitabine based therapy wherein the subject is diagnosed with chronic myelomonocytic leukemia. Indeed, provided herein is technology for biomarkers directed toward predicting a subject's (e.g., a subject diagnosed with CMML or myelodysplastic syndrome (MDS)) responsiveness to a DNA methyltransferase inhibitor (e.g., decitabine, azacitidine) therapy. Markers were identified in a case-control study by comparing the methylation state of DNA markers from subjects diagnosed with CMML that demonstrated or did not demonstrate a favorable response to decitabine therapy (see, Examples 1-8).

In some embodiments, the technology is related to assessing the presence of and methylation state of one or more of the markers identified herein in a biological sample. These markers comprise one or more differentially methylated regions (DMR) as discussed herein (e.g., one or more of DMR Nos. 1-167) (e.g., one or more of DMR Nos. 168-188), e.g., as provided in FIG. 4D and/or FIG. 10B.

In addition, embodiments provide a method of analyzing a DMR from FIG. 4D or FIG. 10B that is DMR Nos. 1-188. In some embodiments, the methods comprise determining the methylation state of two markers, e.g., a pair of markers provided in FIG. 4D and/or FIG. 10B.

Although the disclosure herein refers to certain illustrated embodiments, it is to be understood that these embodiments are presented by way of example and not by way of limitation.

In particular aspects, the present technology provides compositions and methods for identifying, determining, and/or classifying a subject's (e.g., a subject diagnosed with CMML) likelihood of favorably responding to a decitabine therapy. In related aspects, the technology provides compositions and methods for identifying, predicting, and/or detecting such a likelihood. The methods comprise determining the methylation status of at least one methylation marker in a biological sample isolated from a subject (e.g., a bone marrow sample), wherein a change in the methylation state of the marker is indicative of the presence, class, or site of a likely responsiveness to decitabine therapy. Particular embodiments relate to markers comprising a differentially methylated region (DMR, e.g., DMR 1-167, see FIG. 4D, e.g., DMR 168-188, see FIG. 10B) that are used for predicting a subject's (e.g., a subject diagnosed with CMML) responsiveness to decitabine therapy.

In addition to embodiments wherein the methylation analysis of at least one marker, a region of a marker, or a base of a marker comprising a DMR (e.g., DMR 1-167 from FIG. 4D) (e.g., DMR 168-188 from FIG. 10B) provided herein is analyzed, the technology also provides panels of markers comprising at least one marker, region of a marker, or base of a marker comprising a DMR with utility for the prediction of a subject's responsiveness to decitabine therapy.

Some embodiments of the technology are based upon the analysis of the CpG methylation status of at least one marker, region of a marker, or base of a marker comprising a DMR.

In some embodiments, the present technology provides for the use of the bisulfite technique in combination with one or more methylation assays to determine the methylation status of CpG dinucleotide sequences within at least one marker comprising a DMR (e.g., as provided in FIG. 4D (e.g., DMR 1-167)) (e.g., as provided in FIG. 10B (e.g., DMR 168-188)). Genomic CpG dinucleotides can be methylated or unmethylated (alternatively known as up- and down-methylated respectively). However the methods of the present invention are suitable for the analysis of biological samples of a heterogeneous nature, e.g., a low concentration of tumor cells, or biological materials therefrom, within a background of a remote sample (e.g., bone marrow, blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

According to the present technology, determination of the methylation status of CpG dinucleotide sequences in markers comprising a DMR has utility both in the diagnosis and characterization of a subject's (e.g., a subject diagnosed with CMML) responsiveness to a decitabine based therapy.

Combinations of Markers

In some embodiments, the technology relates to assessing the methylation state of combinations of markers comprising one or more DMRs from FIG. 4D and/or FIG. 10B.

In some embodiments, assessing the methylation state of more than one marker increases the specificity and/or sensitivity of a screen for predicting a subject's (e.g., a subject diagnosed with CMML) responsiveness to a decitabine based therapy.

Methods for Assaying Methylation State

The most frequently used method for analyzing a nucleic acid for the presence of 5-methylcytosine is based upon the bisulfite method described by Frommer, et al. for the detection of 5-methylcytosines in DNA (Frommer et al. (1992) *Proc. Natl. Acad. Sci USA* 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uricil is desulfonated under alkaline conditions to form uracil. Detection is possible because uracil forms base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98) or methylation-specific PCR (MSP) as is disclosed, e.g., in U.S. Pat. No. 5,786,146.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" *Nucleic Acids Res.* 24: 5064-6). It is thus possible to analyze individual cells for methylation status, illustrating the utility and sensitivity of the method. An overview of conventional methods for detecting 5-methylcytosine is provided by Rein, T., et al. (1998) *Nucleic Acids Res.* 26: 2255.

The bisulfite technique typically involves amplifying short, specific fragments of a known nucleic acid subsequent to a bisulfite treatment, then either assaying the product by sequencing (Olek & Walter (1997) *Nat. Genet.* 17: 275-6) or a primer extension reaction (Gonzalgo & Jones (1997) *Nucleic Acids Res.* 25: 2529-31; WO 95/00669; U.S. Pat. No. 6,251,594) to analyze individual cytosine positions. Some methods use enzymatic digestion (Xiong & Laird (1997) *Nucleic Acids Res.* 25: 2532-4). Detection by hybridization has also been described in the art (Olek et al., WO 99/28498). Additionally, use of the bisulfite technique for methylation detection with respect to individual genes has been described (Grigg & Clark (1994) *Bioessays* 16: 431-6; Zeschnigk et al. (1997) *Hum Mol Genet.* 6: 387-95; Feil et al. (1994) *Nucleic Acids Res.* 22: 695; Martin et al. (1995) *Gene* 157: 261-4; WO 9746705; WO 9515373).

Various methylation assay procedures are known in the art and can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) *Proc. Natl. Acad. Sci USA* 89: 1827-1831). Additionally, restriction enzyme digestion of PCR products amplified from bisulfite-converted DNA finds use in assessing methylation state, e.g., as described by Sadri & Hornsby (1997) *Nucl. Acids Res.* 24: 5058-5059 or as embodied in the method known as COBRA (Combined Bisulfite Restriction Analysis) (Xiong & Laird (1997) *Nucleic Acids Res.* 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide: control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "MethyLight" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, DMR, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, DMR, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

In some embodiments, Methylation-Sensitive High-Resolution Melting (or HRM) is utilized to gauge patterns in genomic DNA samples (see, e.g., U.S. Patent Application Publication No. 20090181391).

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can by used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, DMR, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" Nat Methods 7: 133-6; Meissner et al. (2005) "Reduced representation bisulfite sequencing for comparative high-resolution DNA methylation analysis" Nucleic Acids Res. 33: 5868-77.

In some embodiments, a quantitative allele-specific real-time target and signal amplification (QuARTS) assay is used to evaluate methylation state. Three reactions sequentially occur in each QuARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes cleavase to release the flap sequence by cutting between the detection probe and the flap sequence. The flap sequence is complementary to a nonhairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" Clin Chem 56: A199; U.S. patent application Ser. Nos. 12/946,737, 12/946,745, 12/946,752, and 61/548,639.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715, which is incorporated by reference in its entirety). It is preferred that the bisulfite treatment is conducted in the presence of denaturing solvents such as but not limited to n-alkylenglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). The bisulfite conversion is preferably carried out at a reaction temperature between 30° C. and 70° C., whereby the temperature is increased to over 85° C. for short times during the reaction (see: PCT/EP2004/011715, which is incorporated by reference in its entirety). The bisulfite treated DNA is preferably purified prior to the quantification. This may be conducted by any means known in the art, such as but not limited to ultrafiltration, e.g., by means of Microcon™ columns (manufactured by Millipore™. The purification is carried out according to a modified manufacturer's protocol (see, e.g., PCT/EP2004/011715, which is incorporated by reference in its entirety).

In some embodiments, fragments of the treated DNA are amplified using sets of primer oligonucleotides according to the present invention and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in 10 length.

In another embodiment of the method, the methylation status of CpG positions within or near a marker comprising a DMR (e.g., DMR 1-167 as provided in FIG. 4D) (e.g., DMR 168-188 as provided in FIG. 10B) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids"), incorporated herein by reference in its entirety.

Methods

In some embodiments the technology, methods are provided that comprise the following steps:

1) contacting a nucleic acid (e.g., genomic DNA, e.g., isolated from a body fluids such as a bone marrow sample) obtained from the subject with at least one reagent or series of reagents that distinguishes between methylated and non-methylated CpG dinucleotides within at least one marker comprising a DMR (e.g., DMR 1-167, e.g., as provided in FIG. 4D) (e.g., DMR 168-188, e.g., as provided in FIG. 10B) and
2) detecting the subject's likely responsiveness to a decitabine based therapy (e.g., afforded with a sensitivity of greater than or equal to 80% and a specificity of greater than or equal to 80%).

Genomic DNA may be isolated by any means, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types are contemplated. In some embodiments, the sample comprises bone marrow tissue. In some embodiments, the sample comprises cell lines, histological slides, biopsies, paraffin-embedded tissue, body fluids, stool, colonic effluent, urine, blood plasma, blood serum, whole blood, isolated blood cells, cells isolated from the blood, and combinations thereof.

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Appl. Ser. No. 61/485,386 or by a related method.

The genomic DNA sample is then treated with at least one reagent, or series of reagents, that distinguishes between methylated and non-methylated CpG dinucleotides within at least one marker comprising a DMR (e.g., DMR 1-167, e.g., as provided by FIG. 4D) (e.g., DMR 168-188, e.g., as provided by FIG. 10B).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfate (hydrogen sulfite, disulfite) followed by alkaline hydrolysis.

The treated nucleic acid is then analyzed to determine the methylation state of the target gene sequences (at least one gene, genomic sequence, or nucleotide from a marker comprising a DMR, e.g., at least one DMR chosen from DMR 1-167, e.g., as provided in FIG. 4D) (at least one gene, genomic sequence, or nucleotide from a marker comprising a DMR, e.g., at least one DMR chosen from DMR 168-188, e.g., as provided in FIG. 10B). The method of analysis may be selected from those known in the art, including those listed herein, e.g., QuARTS and MSP as described herein.

Aberrant methylation, more specifically hypermethylation of a marker comprising a DMR (e.g., DMR 1-167, e.g., as provided by FIG. 4D) (e.g., DMR 168-188, e.g., as provided by FIG. 10B) is associated with a subject's (e.g., a subject diagnosed with CMML) responsiveness to decitabine therapy).

The technology relates to the analysis of any sample associated with a subject diagnosed with CMML for whom decitabine therapy is being contemplated. For example, in some embodiments the sample comprises bone marrow tissue obtained from a patient. In some embodiments, the subject is human. Such samples can be obtained by any number of means known in the art, such as will be apparent to the skilled person.

In some embodiments, the technology relates to a method for treating a patient (e.g., a patient diagnosed with CMML), the method comprising determining the methylation state of one or more DMR as provided herein and administering a treatment to the patient based on the results of determining the methylation state. For example, if the methylation state indicates the patient would likely be responsive to a decitabine therapy, then a decitabine therapy is administered to the subject. In some embodiments, if the methylation state indicates the subject is likely to not be responsive to a decitabine therapy, then an alternate therapy not including decitabine is administered.

As noted, experiments conducted during the course of developing embodiments for the present invention identified differentially expressed genes between responders and non-responders to decitabine therapy. Genes up-regulated in responders were enriched in the cell cycle, potentially contributing to effective DAC incorporation. Two chemokines overexpressed in non-responders—CXCL4 and CXCL7— were able to block the effect of DAC on normal CD34' and primary CMML cells in vitro, suggesting their up-regulation contributes to primary DAC resistance. As such, in some embodiments wherein a methylation state indicates the patient is likely to not be responsive to a decitabine therapy, then either a CXCL4 and/or a CXCL7 inhibiting agent is applied to the subject prior to or concurrently with a decitabine therapy. Such embodiments are not limited to a particular type or kind of a CXCL4 and/or CXCL7 inhibiting agent.

The presently disclosed subject matter further provides in some embodiments a method for determining whether to initiate or continue prophylaxis or treatment of CMML in a subject. In some embodiments, the method comprises providing a series of biological samples (e.g., bone marrow samples) over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict the subject's responsiveness to a decitabine therapy, predict clinical outcome, determine whether to initiate or continue or change the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with a subject's responsiveness to decitabine therapy, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

In some embodiments, a statistical analysis associates an indicator with a predisposition to an adverse outcome (e.g., responsiveness or resistance to decitabine therapy). For example, in some embodiments, a methylation state different from that in a normal control sample obtained from a patient who is responsive to decitabine therapy indicates that a subject is more likely to be resistant or non-responsive to decitabine therapy, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a biomarker disclosed herein (e.g., a DMR) can be established, and the degree of change in the methylation state of the biomarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%.

In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors known to be resistant to decitabine therapy. In certain embodiments of the method, a subject is identified as likely being resistant or non-responsive to decitabine therapy upon identifying an aberrant methylation state of one or more DMR provided herein in a biological sample obtained from the subject.

The analysis of markers can be carried out separately or simultaneously with additional markers within one test sample. For example, several markers can be combined into one test for efficient processing of a multiple of samples and for potentially providing greater predictive accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the likely decitabine responsiveness status that includes, but is not limited to, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples.

As mentioned above, depending on the embodiment of the method of the present technology, detecting a change in methylation state of the one or more biomarkers can be a qualitative determination or it can be a quantitative determination. As such, the step of predicting a subject's responsiveness to decitabine therapy indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to such predictive methods, a preferred subject is a vertebrate subject. A preferred vertebrate is warm-blooded; a preferred warm-blooded vertebrate is a mammal. A preferred mammal is most preferably a human (e.g., a human diagnosed with CMML). As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like.

The presently-disclosed subject matter further includes a systems for predicting a subject's (e.g., a subject diagnosed with CMML) responsiveness to decitabine therapy. The system can be provided, for example, as a commercial kit that can be used to screen for such responsiveness in a subject from whom a biological sample (e.g., a bone marrow sample) has been collected. An exemplary system provided in accordance with the present technology includes assessing the methylation state of a DMR as provided in FIG. 4D and/or FIG. 10B.

EXAMPLES

Example 1—Somatic Mutations do not Correlate with Response to Decitabine in CMML Somatic mutations in epigenetic modifying enzymes and other genes are prevalent in MDS and CMML (see, e.g., Walter, M. J., et al., Leukemia. 2011; 25(7):1153-1158; Tefferi, A., Leukemia. 2009; 23(7):1343-1345; Abdel-Wahab, O., Blood. 2009; 114(1):144-147; Bejar, R., N Engl J Med. 2011; 364(26):2496-2506; Jankowska, A. M., Blood. 2011; 118(14):3932-3941; Kosmider, O., Haematologica. 2009; 94(12):1676-1681; Yoshida, K., Nature. 2011; 478 (7367):64-69; Patnaik, M. M., Am J Hematol. 2013; 88(3): 201-206). Recently, it has been reported that mutations in TET2 and DNMT3A are associated with response to DMTi therapy in MDS and related disorders (see, e.g., Bejar, et al., Blood 2014; 124(17):2705-2712; Traina, F., Leukemia. 2014; 28(1):78-87; Itzykson, R., Leukemia. 2011; 25(7): 1147-1152). Despite this, presence of these mutations did not translate to an improved overall survival in any of these studies, indicating that therapeutic response and survival benefit are likely influenced by multiple different factors. Moreover, these findings have not been recapitulated in CMML exclusively (see, e.g., Braun, T., Blood. 2011; 118 (14):3824-3831).

To determine whether particular genetic or epigenetic abnormalities are associated with DMTi sensitivity or resistance in this disease a cohort of primary CMML cases was studied. Bone marrow mononuclear cells (BM MNC) were collected at the time of diagnosis from 40 patients with de novo CMML. All patients included in this study were enrolled in a clinical trial of the Fondazione Italiana per le Sindromi Mielodisplastiche (FISM) and treated with DAC single agent as front-line therapy (20 mg/m$^2$/day×5 days) and response was evaluated after 6 cycles of treatment. Responsive patients (n=20) were defined as those who achieved either complete remission (CR), marrow complete remission (mCR), partial remission (PR) or hematological improvement (HI), as defined by the 2006 International Working Group (IWG) response criteria in myelodysplasia (see, e.g., Cheson, B. D., Blood. 2006; 108(2):419-425). Patients with either stable or progressive disease (SD and PD, respectively) were considered as having primary resistance to DAC (n=20). As shown in Table 1, there were no significant differences in terms of age, gender, bone marrow monocytosis, blast percentage, cytogenetics or presence of either splenomegaly or extramedullary lesions between responder and non-responder patients. Using MiSeq to sequence DNA isolated from the diagnostic BM MNC targeted re-sequencing of a panel of genes mutated at frequencies greater than 5% in CMML was performed: SRSF2, TET2, ASXL1, NRAS, DNMT3A, RUNX1, U2AF1, TP53, JAK2, KIT KRAS, SF3B1, EZH2, IDH1, and IDH2. Similar to previous reports, SRSF2, TET2, and ASXL1 were the most frequently mutated genes in this cohort of patients (see, e.g., Abdel-Wahab, O., et al., Blood. 2009; 114(1):144-147; Jankowska, A. M., Blood. 2011; 118(14):3932-3941; Yoshida, K., Nature. 2011; 478(7367): 64-69; Patnaik, M. M., et al., Am J Hematol. 2013; 88(3): 201-206; Itzykson, R., et al., J Clin Oncol. 2013; 31(19): 2428-2436; Patnaik, M. M., et al., Leukemia. 2013; 27(7): 1504-1510; Meggendorfer, M., Blood. 2012; 120(15):3080-3088; Kohlmann, A., J Clin Oncol. 2010; 28(24):3858-3865). However, no somatic mutation was significantly correlated with response to DAC (FIG. 1A).

TABLE 1

Clinical characteristics of the FISM CMML patient cohort treated with Decitabine.

| Clinical Characteristics | Responders | Non-responders | p-value |
|---|---|---|---|
| Total Patients | 20 | 20 | |
| CMML1 (%) | 15 (75%) | 10 (50%) | ns[A] |
| CMML2 (%) | 5 (25%) | 10 (50%) | |
| Male (%) | 14 (70%) | 14 (70%) | ns[A] |
| Female (%) | 6 (30%) | 6 (30%) | |
| Median Age (years) (range) | 73.5 (45-84) | 70.5 (41-82) | ns[B] |
| Median Survival (months) (range) | 26.5 (6-39) | 13.5 (2-25) | p = 0.0004[C] |
| Median hemoglobin (range) | 10 (7.2-14.9) | 9.7 (6.6-13.8) | ns[A] |
| Median marrow blasts (%) (range) | 5 (0-18) | 7 (0-19) | ns[D] |
| Median monocytes (%) (range) | 24 (2-67) | 22 (5-45) | ns[D] |
| Median WBC (%) (range) | 17.8 (3.7-75.2) | 18.9 (2.8-52.5) | ns[A] |
| Cytogenetics Normal | 14 | 14 | ns[A] |
| Abnormal | 6 | 6 | |
| Splenomegaly | 9 | 7 | ns[A] |
| Hepatomegaly | 8 | 5 | ns[A] |
| Lymphadenomegaly | 2 | 3 | ns[A] |

Figure 1B:
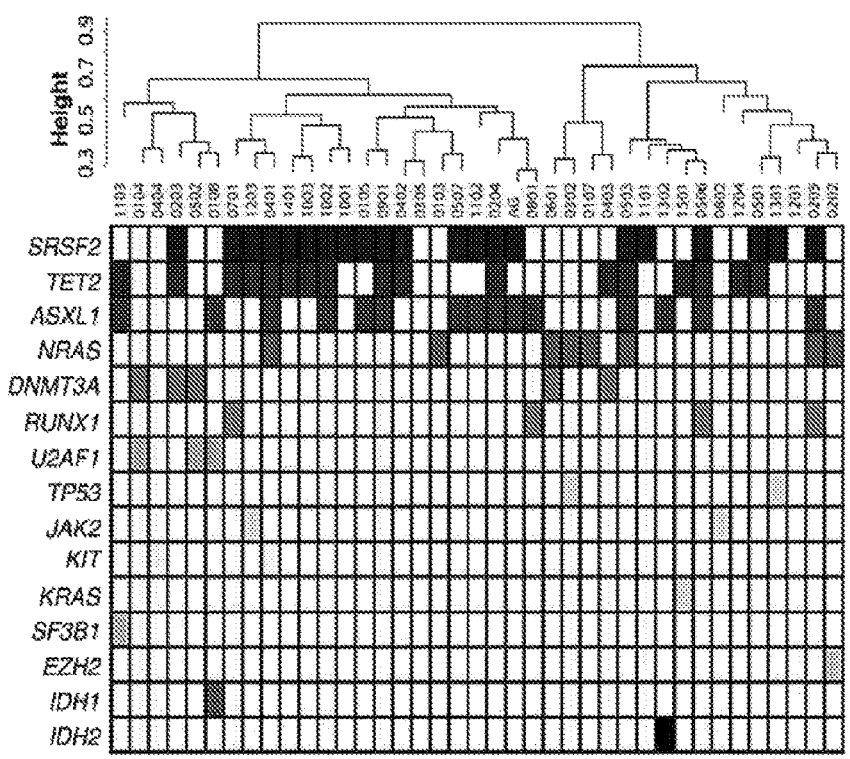
Figure 2:
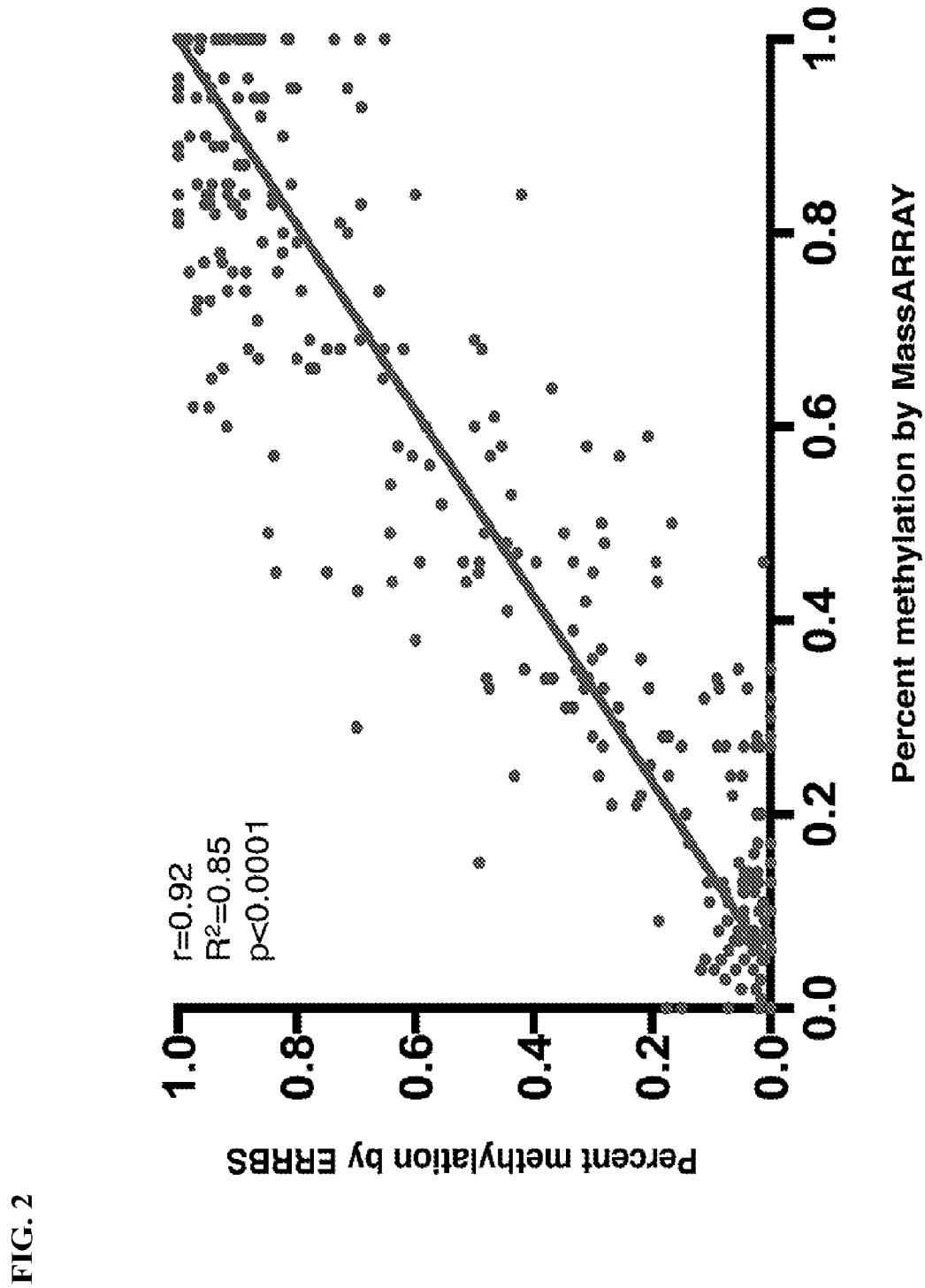
FIG. 2: Technical validation of ERRBS performance accuracy by MassARRAY EpiTYPER. DNA from 8 randomly-selected patients was used for an independent round of bisulfite treatment followed by site-specific PCR amplification and processed for MALDI-TOF analysis as previously described (see, e.g., Nimer, S. D. Blood. 2008; 111 (10):4841-4851). The primers and corresponding amplicon sequences are listed in Supplementary Table 6. Forty-seven CpG sites were covered by both MassARRAY and ERRBS, and the methylation status at most, but not all, CpGs was available in all 8 patient samples by both methods. This resulted in a total of 292 CpGs analyzed by both methods with $r=0.92$, $R^2=0.85$, $p<0.0001$.
Figures 5A, 5B, 5C:
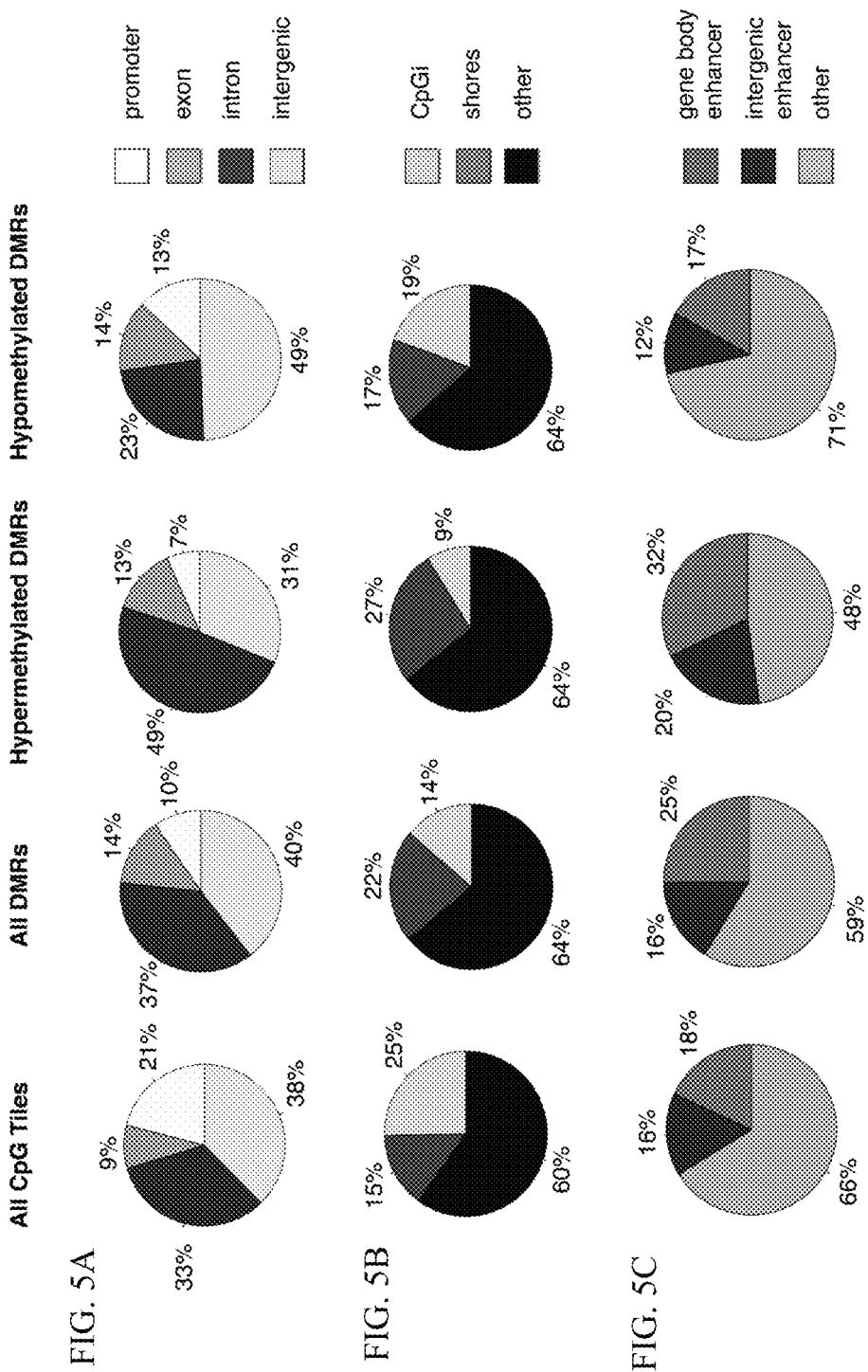
FIG. 5A-C: Differentially methylated regions are enriched at distal intergenic regions and enhancers. A. Pie charts illustrating the relative proportion of CpG tiles and DMRs annotated to RefSeq promoter, exon, intron and intergenic regions. B. Pie charts illustrating the relative proportion of CpG tiles and DMRs annotated to CpG islands, CpG shores and regions beyond CpG shores. C. Pie charts illustrating the relative proportion of CpG tiles and DMRs annotated to enhancers within gene bodies, enhancers within intergenic regions and non-enhancer regions.

[A]Fisher's exact test;
[B]t-test;
[C]log-rank test,
[D]Wilcoxon rank-sum test;
Abbreviations:
CMML: chronic myelomonocytic leukemia;
IPSS: International prognostic scoring system,
N/A: not available;
WBC: white blood cells It has been previously reported that distinct DNA methylation profiles in acute myeloid and lymphoid leukemias (AML and ALL) are strongly correlated with the presence of specific molecular and cytogenetic subtypes (see, e.g., FIGueroa, M. E., et al., Blood. 2009; 114(16):3448-3458; Akalin, A., et al., PLoS Genet. 2012; 8(6):e1002781; FIGueroa, M. E., et al., Cancer Cell. 2010; 18(6):553-567; FIGueroa, M. E., et al., J Clin Invest. 2013; 123(7):3099-3111; Bullinger, L., et al., Blood. 2010; 115(3):636-642). To determine if similarly distinct methylation patterns in CMML can be linked to the presence of specific somatic mutations, DNA methylation patterns in the same specimens were examined through enhanced reduced representation bisulfite sequencing (ERRBS) (see, e.g., Akalin, A., et al., PLoS Genet. 2012; 8(6):e1002781), a deep sequencing method that captures and accurately quantifies DNA methylation at approximately 3 million CpG sites. ERRBS data was available for 39 of the 40 patients; 19 non-responders and 20 responders. Percent methylation measured by ERRBS was highly concordant with a quantitative single locus DNA methylation validation assay using MassARRAY EpiTYPER (FIG. 2) (see, e.g., Ehrich, M., et al., Proc Natl Acad Sci U S A. 2005; 102(44):15785-15790). Unsupervised clustering analysis of the patients based on their DNA methylation patterns did not reveal a correlation between gene mutations and particular methylation clusters (FIG. 1B). In addition, there was no significant difference in the observed patient survival time between the two top-level methylation clusters (log-rank test, p value=0.33).

Next, supervised analyses were performed comparing wild-type versus mutant cases for TET2, ASXL1, DNMT3A and SRSF2 to identify differentially methylated regions (DMRs) associated with each of these mutations. As expected given its role in de novo DNA methylation, a predominantly hypomethylated profile associated with DNMT3A mutations was identified (Total DMRs: 243, hypomethylated DMRs [Hypo-DMRs]: 197 and hypermethylated DMRs [Hyper-DMRs]: 46) which was targeted mainly at intergenic and intronic regions (FIG. 3A). By contrast, TET2 loss-of-function mutations were associated with the presence of hypermethylation compared to TET wild-type cases (Total DMRs: 188, Hypo-DMRs: 48, Hyper-DMRs: 140) (FIG. 3B). Mutations in ASXL1, another epigenetic modifier, were associated with a specific signature consisting of equal proportions of hyper and hypomethylated DMRs (Total DMRs: 144, Hypo-DMRs: 82, Hyper-DMRs: 62). Both hyper- and hypo-DMRs in ASXL1 mutant CMML cases were strongly depleted from promoter regions (Hyper-DMRs 3% vs. Background 21%, p value=6.79×10-5; Hypo-DMRs 5% vs. Background 21%, p value=4.30×10-5), and significantly enriched at intergenic regions (Hyper-DMRs 47% vs. Background 38%, p value=0.1; Hypo-DMRs 54% vs. Background 38%, p value=2.84×10-3) (FIG. 3C). Notably, mutations in the splicing factor SRSF2 were linked to the strongest DNA methylation differences, with a total of 724 DMRs (Hypo-DMRs: 383, Hyper-DMRs: 341). In this case, hypermethylated DMRs were strongly enriched at promoter regions (Hyper-DMRs 31% vs. Background 21%, p value=1.44×10-5) and depleted from introns (Hyper-DMRs 19% vs. Background 33%, p value=1.50×10-8 (FIG. 3D). While SRSF2 itself does not have any direct epigenetic function, it is likely that mutations in this gene may lead to mis-splicing and consequent deregulation of other epigenetic modifier genes, resulting in this strong epigenetic signature. Additionally, the observed survival time was not significantly different between the patients with or without individual DNMT3A, TET2, ASXL1, and SRSF2 mutations (log-rank test, p value=0.61, 0.067, 0.93, 0.58, respectively).

Example 2—A Specific Epigenetic Profile Distinguishes DAC-Resistant CMML Patients at Diagnosis Previous efforts have failed to identify baseline epigenetic differences between DMTi-sensitive and -resistant patients (see, e.g., Figueroa, M. E., et al., Blood. 2009; 114(16): 3448-3458; Shen, L., et al., J Clin Oncol. 2010:28(4):605-613; Fandy, T. E., et al., Blood. 2009; 114(13):2764-2773). However, all of these studies were performed using platforms that examined DNA methylation within CpG islands and gene promoters. Recent and increasing evidence suggests that DNA methylation and other epigenetic modifications at enhancers and other distal regulatory regions play a key role in transcriptional regulation and that these regions are often located at a significant distance from the transcription start site of the target gene (see, e.g., Sanyal, A., et al., Nature. 2012; 489(7414):109-113). Therefore, it was hypothesized that key epigenetic differences may exist between DAC-sensitive and -resistant patients at diagnosis that are located distally from promoters, targeting enhancers and other distal regulatory regions.

For this purpose the Enhanced reduced Representation Bisulfite Sequencing (ERRBS) assay was used, a deep sequencing-based method that targets not only promoter regions, but also introns, exons and distal intergenic regions (see, e.g., Akalin, A., et al., PLoS Genet. 2012; 8(6): e1002781). Using the MethylSig package a direct comparison was performed between the diagnostic DNA methylation profiles of DAC-sensitive and DAC-resistant patients (see, e.g., Park, Y., et al., Bioinformatics. 2014). 167 differentially methylated regions (DMRs) were identified that displayed a methylation difference of ≥25% between responders and non-responders and were statistically significant at a False Discovery Rate (FDR)<0.1. Among these DMRs were regions displaying higher methylation in responders, as well as regions of lower methylation as compared to non-responders (see, FIG. 4A: FIG. 4C: FIG. 4D: Table 2). Hierarchical clustering of the cohort using these DMRs was sufficient to achieve a perfect segregation of DAC-sensitive and DAC-resistant patients (FIG. 4B). These findings indicate that numerous epigenetic differences exist at the time of diagnosis that correlate with a patient's likelihood to respond to DAC treatment.

Example 3—Response-Associated DMRs Localize Preferentially to Distal Regulatory Regions Next it was determined whether DMRs distributed evenly across the genome or whether they were enriched at specific genomic regions. For this both the genomic distribution of DMRs as well as their association with known regulatory regions were analyzed. Notably, analysis of the distribution of DMRs relative to coding regions revealed that DMRs were significantly depleted at promoter regions (DMRs 10% vs. Background 21%, binomial test p-value: $6.70 \times 10^{-5}$) with a concurrent enrichment at intronic regions. This distribution was not the same across hypermethylated and hypomethylated DMRs. While all DMRs were depleted at promoter regions, hypermethylated DMRs were significantly enriched at introns (Hyper DMRs 49% vs. Background 33%, binomial test p-value: $1.29 \times 10^{-3}$) while hypomethylated DMRs were enriched at intergenic regions (Hypo DMRs 49% vs. 38% background, binomial test p-value: 0.03) (FIG. 4A).

Next, the association of DMRs with regulatory regions was determined. For this purpose, relative enrichment at CpG island and enhancer regions were analyzed. Analysis of CpG islands and CpG shores demonstrated that DMRs were also significantly depleted at CpG islands (DMRs 14% vs. Background 25%, binomial test p-value: $2.8 \times 10^{4}$) with enrichment at CpG shores and other regions (DMRs 22% vs. Background 15%, binomial test p-value: 0.006; and 70% vs. 60%, binomial test p-value: $8.79 \times 10^{-3}$ respectively). This pattern was conserved across both hypermethylated and hypomethylated DMRs (FIG. 4B).

Recently, DNA methylation at enhancers was reported to strongly correlate with aberrant gene expression observed in cancer cells (see, e.g., Aran, D., et al., Genome Biol. 2013; 14(3):R21). It was hypothesized that differential DNA methylation at enhancers may be better correlated with differential response to DAC in CMML than promoter methylation. Enrichment analysis of all DMRs relative to intragenic and intergenic enhancers revealed that DMRs were enriched for intragenic enhancers (DMRs 25% vs. Background 18%, binomial test p-value: 0.01). When this analysis was stratified into hypermethylated and hypomethylated DMRs, it became apparent that hypermethylated DMRs showed the strongest enrichment for enhancer regions, and in particular, enhancers located within gene bodies (hyper DMRs 32% vs. background 18%, binomial test p-value: $8.14 \times 10^{-4}$). Conversely, hypomethylated DMRs were not significantly enriched in enhancer regions and were similarly distributed within gene body- and intergenic enhancers (FIG. 4C).

Figure 6A:
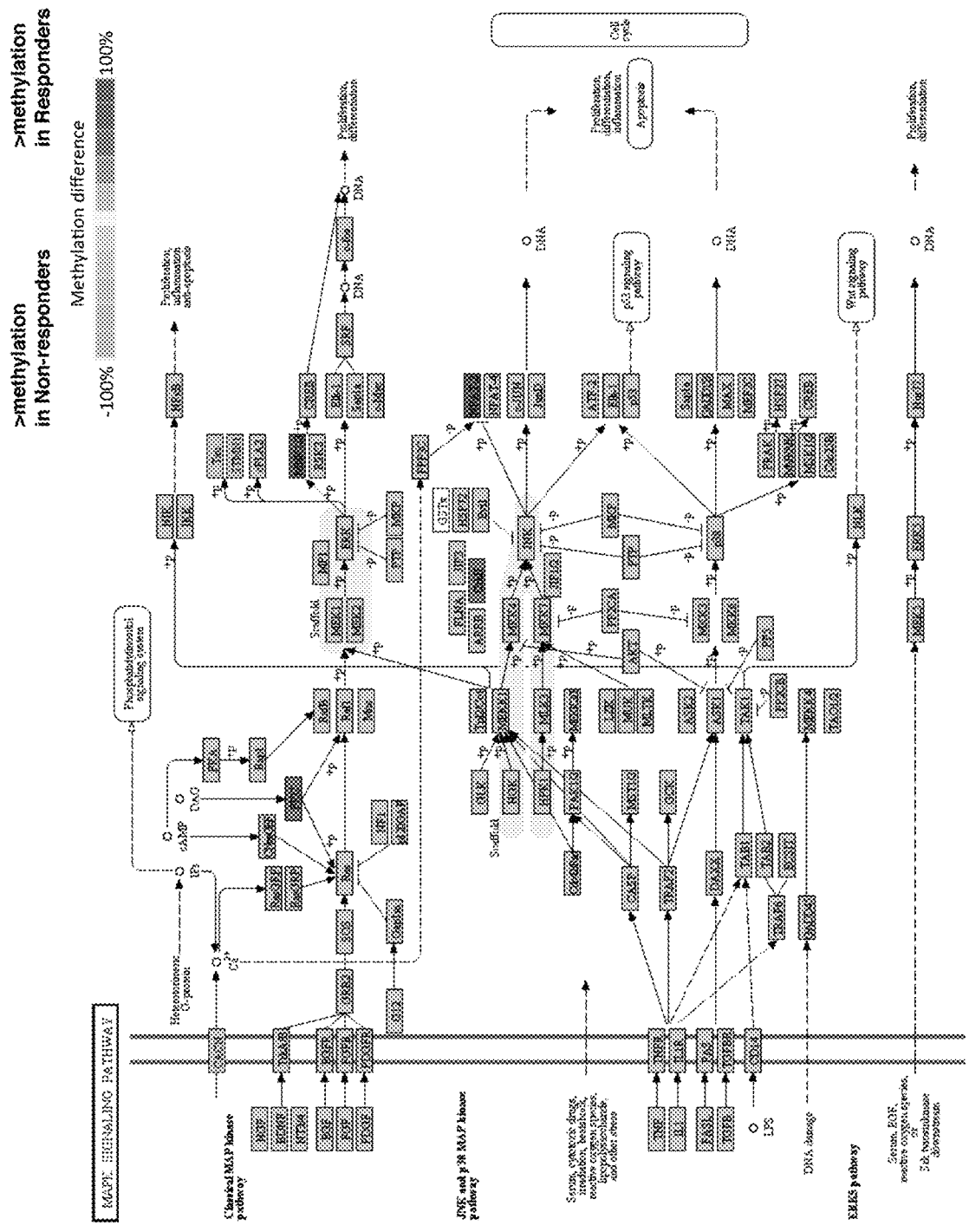
FIG. 6A-B: Pathway analysis for DMR-annoted genes. A. Kegg pathway analysis revealed the enrichment of DMR at genes involved in MAPK signaling. B. Heatmap of 3 MAPK-annotated DMRs in responders and non-responders as determined by MassARRAY EpiTYPER.
Figure 6B:
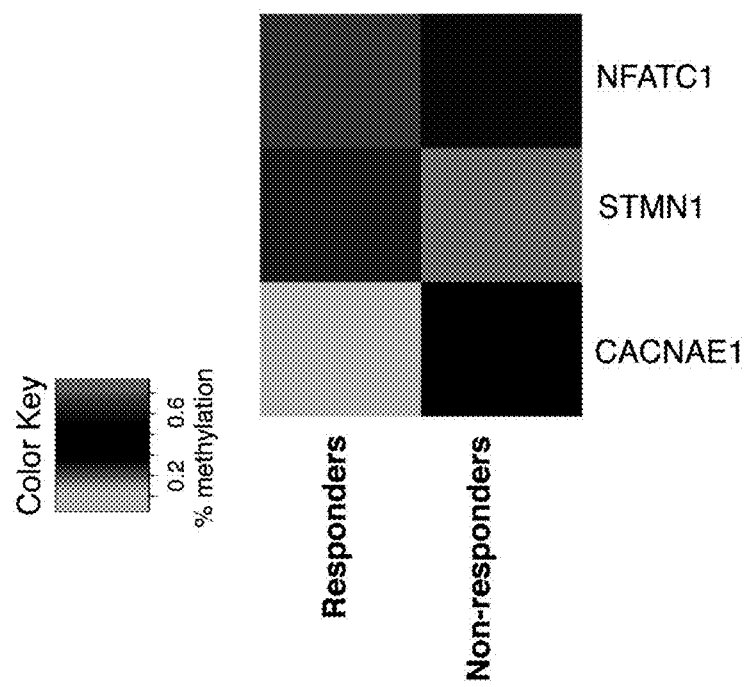

Finally, it was asked whether the DMRs associated with DAC response were specifically enriched within relevant biological pathways. The 167 DMRs were annotated to known genes and pathway enrichment analysis was performed against the KEGG pathway database. The MAP kinase signaling pathway, which plays a key role in cell cycle, apoptosis, cell proliferation and differentiation, was significantly enriched in DMR-associated genes (Hypergeometric test p-value: $7.68 \times 10^{-3}$, FDR: 0.084) (FIG. 6A). There were 7 DMRs that were annotated to MAPK pathway genes, including STMN1, CACNAE1, PRKCB, MAPT, NFATC1, CRKL, and MKNK2(FIG. 7A; FIG. 7B). Three of these DMRS—those annotated to STMN1, CACNAE1, and MAPT—were hypermethylated in DAC non-responders, while MKNK2-, NFATC1-, CRKL-, and PRKCB-associated DMRs were hypermethylated in DAC responders (summarized in FIG. 7A; FIG. 7B). To further validate epigenetic deregulation of the MAPK signaling pathway in these patients, MassARRAY EpiTYPER analysis of 3 of the affected MAPK genes in the pathway in a subset of samples was performed (FIG. 6B). This analysis confirmed the increased methylation in the STMN1 and CACNAE1 DMRs in non-responder patients, as well as validating the increased methylation of the NFATC1 DMR in responders.

Figure 8A:
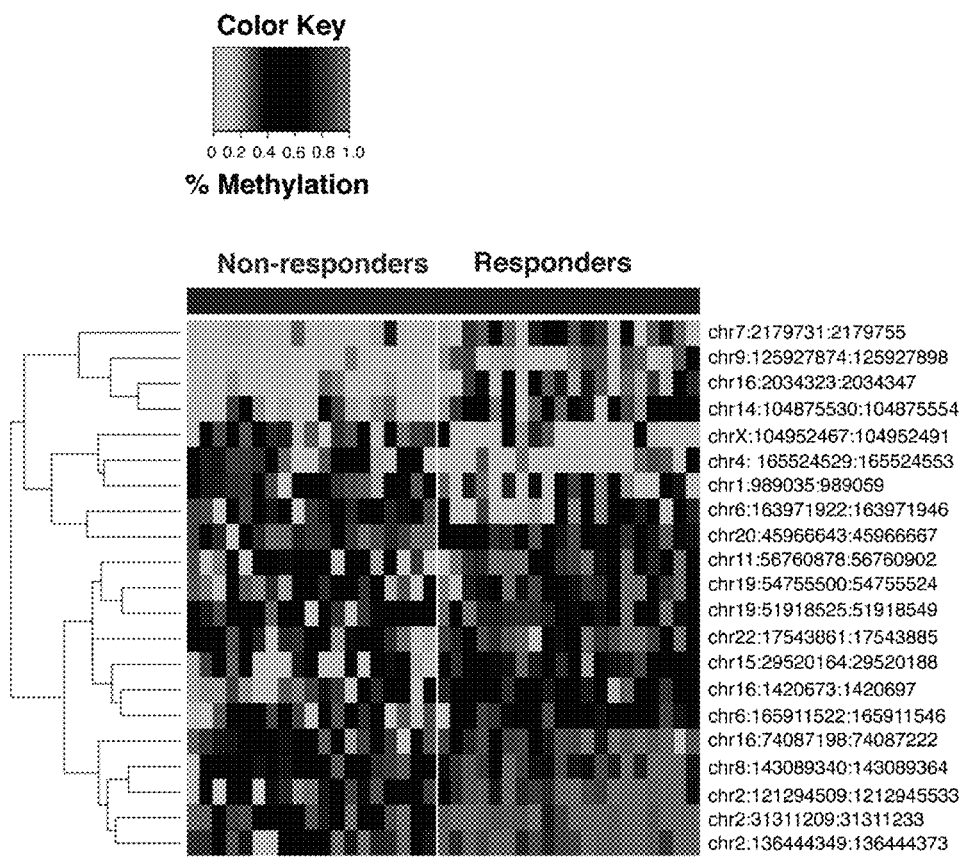
Figure 8B:
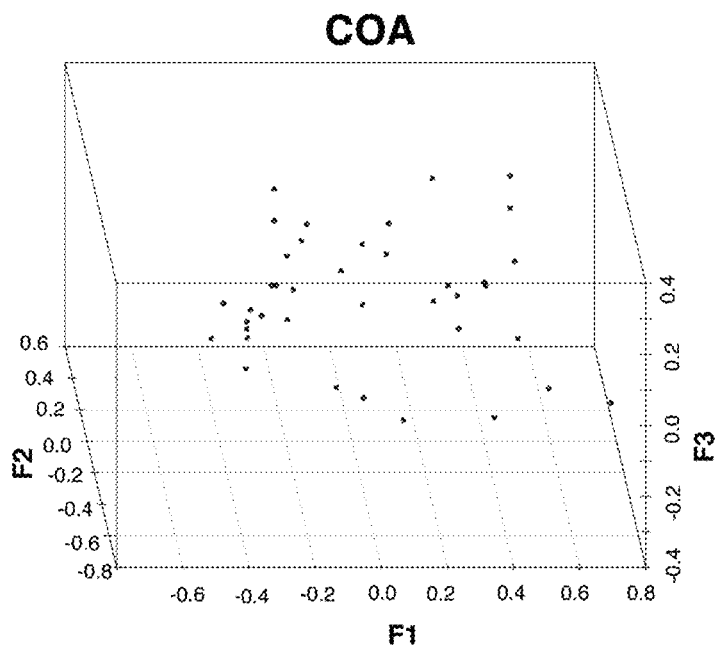
Figure 9A:
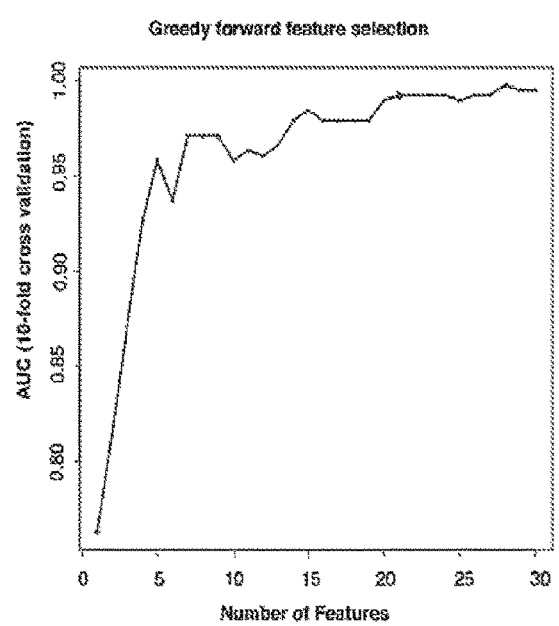
FIG. 9A-D: Methylation status at 21 genomic regions can be used to predict Decitabine (DAC) response at diagnosis. A. Forward feature selection identified 21 CpG regions with the highest performance in classifying the samples. B. Principle components analysis (PCA) using the 21 features C. Multi-dimensional scaling (MDS) analysis of patients using the 21 genomic features. Patients are labeled with their specific type of response; CR: complete response; HI: hematological improvement; mCR: marrow complete response; PD: progressive disease; PR: partial response; SD: stable disease. D. Receiver Operating Characteristic (ROC) after 10-fold cross-validation reflects the performance of the SVM classifier with the 21 selected predictors.
Figure 9B:
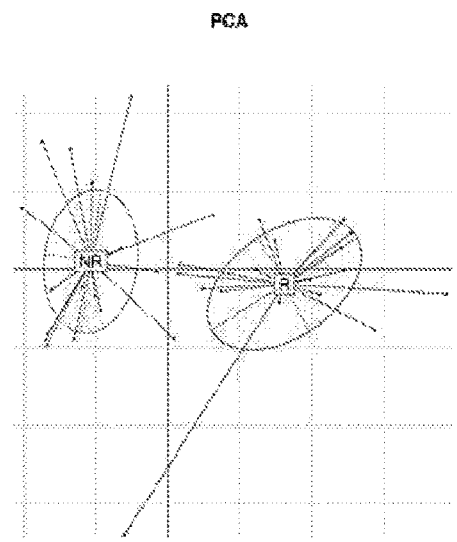
Figure 9C:
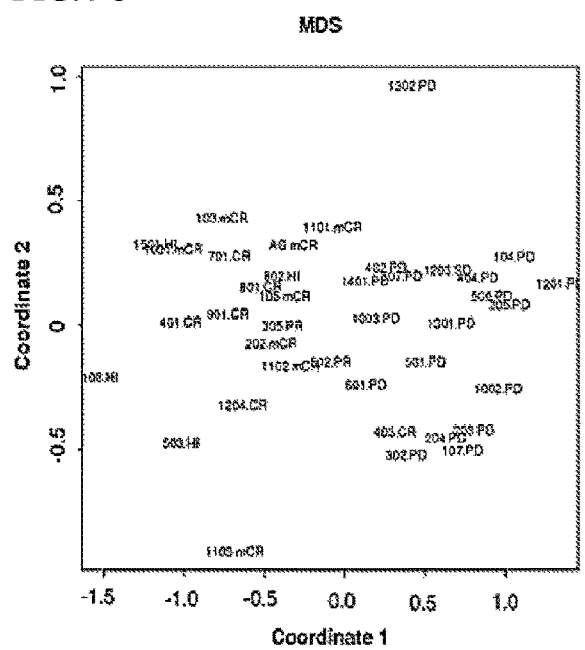
Figure 9D:
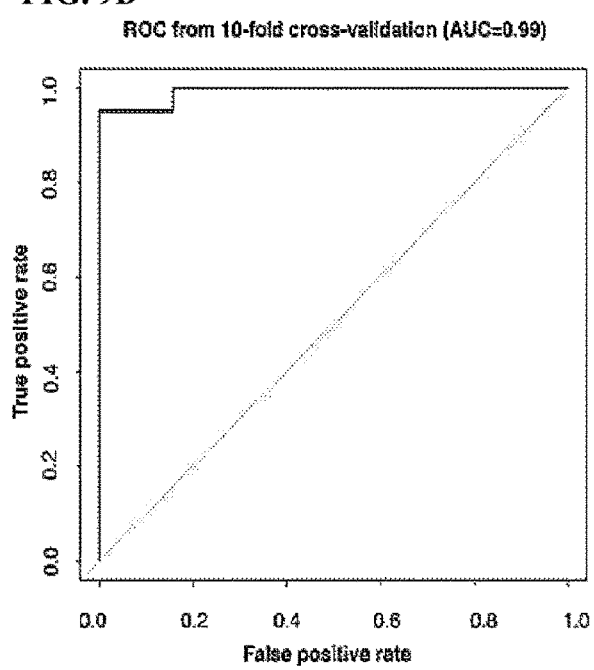

Example 4—DNA Methylaton Differences can be Harnessed for Therapeutic Response Prediction Given that the data identified for the first time the existence of baseline DNA methylation differences between DAC responders and non-responders prior to DAC treatment, it was hypothesized that these unique methylation profiles could be harnessed to predict at the time of diagnosis which patients would be sensitive and resistant to treatment. To test this, the percent cytosine methylation at each genomic location across patients was used as potential predictors, and applied a machine learning approach, support vector machine (SVM) (see, e.g., Cortes, C., and Vapnik, V. Machine Learning. 1995; 20(3):273-297), to build a classifier. By feature selection, twenty-one 25-bp tile regions were identified as the predictors with the highest predictability in the SVM classifier (FIG. 8A; FIG. 9A; FIG. 10A; FIG. 10B). Unsupervised analysis using only the methylation levels at the selected 21 features revealed that they were sufficient to almost separate the 39 samples by responses (FIG. 8B; FIG. 9B; FIG. 9C). Notably, there was no defined clustering of the patients according to their specific degree of response as shown by multi-dimensional scaling (MDS) analysis (FIG. 9C). Ten-fold cross-validation was used to evaluate the predictive performance of the classifier and the reported area under receiver operating characteristic curve (AUC) was 0.99, indicating a strong predictive accuracy for the classifier model (FIG. 9D). In order to assess the robustness of the SVM classifier built with the selected 21 predictors, three different random splits of the cohort into training and test sets were performed. The classifier was trained by each of the three sets of randomly selected samples and the responses for the remaining samples in the corresponding test sets predicted. The classifier was able to accurately predict response to DAC in 18/19 (accuracy=94.74%) (FIG. 8C), 13/14 (accuracy=92.86%) and 9/9 cases (accuracy=100%), respectively (FIG. 11A).

In order to independently validate the predictive accuracy of the SVM classifier, a second cohort of patients on which to test its performance was identified. Twenty-eight additional diagnostic CMML specimens from patients enrolled in a clinical trial from the Groupe Francophone des Myelodysplasies (GFM), all of whom had been treated with the same DAC regimen of 20 mg/m²/day×5 days were collected and subjected to ERRBS (Table 2, Table 3). Specimens in this cohort consisted of sorted monocytes from peripheral blood (PB) and the cohort included 12 responder and 16 non-responder patients. The SVM classifier was applied blindly to these samples, without any prior knowledge of the therapeutic response labels for the cohort. Due to the stochastic nature of ERRBS, the CpG coverage is never identical across all samples, thereby leading to missing values for some regions of interest. In effect, only 6 out of the 21 features were present in all 28 GFM cohort samples. Therefore, an SVM classifier was built on these six shared features by training it on the 39 samples of the FISM cohort and then applying the trained classifier on the GFM cohort. As shown in FIG. 8D and FIG. 11B, despite this limitation the 6-feature classifier was still capable of correctly predicting response for 20/28 patients in the GFM cohort (accuracy=71%). Next, in order to increase the number of features included while still retaining a large enough cohort in which to test the predictive accuracy, 14 out of the 21 features was used to predict response for 19 patients in the GFM cohort. Once again the model was trained with these 16 features using the FISM cohort consisting of the initial 39 patients and then blindly applied it to the 19 test samples from the GFM cohort. This modified classifier with 14 features was capable of accurately predicting therapeutic outcome for 15/19 patients, which represents an accuracy of 79% (FIG. 8D and FIG. 11B). Finally, the maximum number of the original 21 features that was shared by at least 15 GFM patients was identified, which was 16 features. The model was trained using these 16 shared features and then predicted response for the 15 patients in the GFM cohort, achieving an accuracy of 87%. (FIG. 8D and FIG. 11B). These findings demonstrate that the SVM classifier is general enough to be applied to and accurately predict therapeutic outcome of fully independent samples, which is a critical step in the development of a biomarker, Moreover, this robustness was maintained even across different cell types (BM MNC in the training set vs. PB monocytes in the validation set), further underscoring the power of the classifier to predict outcome in an independent cohort. These findings demonstrate that the epigenetic differences between responders and non-responders at diagnosis have the potential to be harnessed as classifiers to predict clinical response to DAC.

TABLE 2

Clinical characteristics of the GFM CMML cohort treated with Decitabine.

| Clinical Characteristics | Responders | Non-responders | p-value |
|---|---|---|---|
| Total Patients | 12 | 16 | |
| CMML1 (%) | 2 (17%) | 10 (62.5%) | p = 0.0235[A] |
| CMML2 (%) | 10 (83%) | 6 (37.5%) | |
| Male (%) | 9 (75%) | 13 (81%) | ns[A] |
| Female (%) | 3 (25%) | 3 (19%) | |
| Median Age (years) (range) | 72.5 (61-88) | 71 (55-85) | ns[B] |
| Median Survival (months) (range) | 39 (8-95) | 14.5 (5-67) | ns[C] |
| Median hemoglobin (range) | 9.1 (6.7-13.3) | 9.05 (8-12.2) | ns[A] |
| Median marrow blasts (%) (range) | 14 (3-20) | 9 (4-19) | ns[D] |
| Median monocytes (%) (range) | 23 (2-47) | 15.5 (3-34) | ns[D] |

TABLE 2-continued

Clinical characteristics of the GFM
CMML cohort treated with Decitabine.

| Clinical Characteristics | Responders | Non-responders | p-value |
|---|---|---|---|
| Median WBC (%) (range) | 18.9 (4.9-77.5) | 24.95 (4.1-81.7) | ns[A] |
| Cytogenetics Normal | 7 | 11 | ns[A] |
| Abnormal | 5 | 5 | |

[A]Fisher's exact test;
[B]t-test;
[C]log-rank test,
[D]Wilcoxon rank-sum test;
Abbreviations:
CMML: chronic myelomonocytic leukemia;
WBC: white blood cells

TABLE 3

Somatic mutations in GFM CMML cohort

| Gene | Responder n (%) | Non-responder n (%) | p-value[A] |
|---|---|---|---|
| SRSF2* | 7/8 (87.5) | 3/9 (30) | p = 0.05 |
| ASXL1 | 7/12 (58.3) | 7/16 (43.7) | p = 0.70 |
| TET2 | 10/12 (83.3) | 6/16 (37.5) | p = 0.02 |
| RAS | 6/12 (50) | 3/16 (18.8) | n = 0.40 |
| U2AF1 | 1/12 (8.3) | 1/16 (6.25) | n = 1.0 |
| JAK2 | 0/12 (0) | 0/16 (0) | n = 1.0 |
| SF3B1 | 0/12 (0) | 1/16 (6.25) | n = 1.0 |
| KIT | 0/12 (0) | 1/16 (6.25) | n = 1.0 |
| RUNX1 | 2/12 (16.7) | 5/16 (31.3) | n = 0.66 |

Figure 12A:
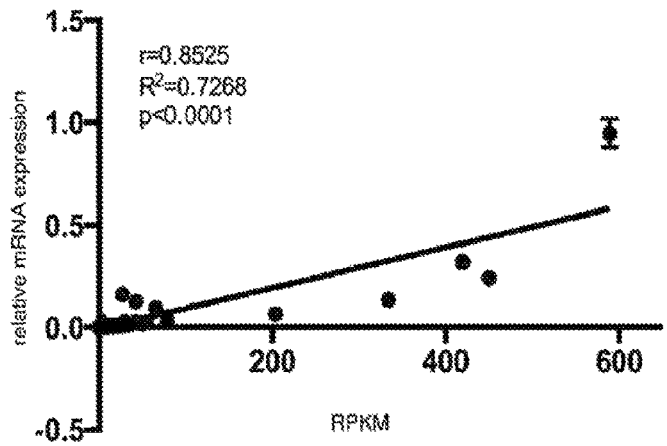
FIG. 12A-C: CXCL4 and 7 are overexpressed in patients resistant to Decitabine (DAC). A. RNA-seq validation by qRT-PCR. Quantitative reverse transcription PCR (qRT-PCR) was used to technically validate the RNA-seq analysis on 13 out of 14 patients and indicates strong correlation between the RNA-seq results (reads per kilobase per million mapped reads, RPKM) and qRT-PCR analysis (relative mRNA to RPL19) for CXCL4, CXCL7, and ITGβ3. B-C. CXCL4 (B) and CXCL7 (C) are expressed in multiple cell types in the hematopoietic system. Expression data from Hemaexplorer (see, e.g., Bagger, F. O., et al., Blood. 2012; 119(26):6394-6395; Bagger, F. O., et al., Nucleic Acids Res. 2013; 41(Database issue):D1034-1039) in the normal human hematopoetic system indicate that expression of CXCL4 and CXCL7 is not limited to megakaryocytes. Early HPC_BM; early hematopoietic progenitor cell, bone marrow; HSC_BM, hematopoetic stem cell, bone marrow; CMP, committed myeloid progenitor; GMP, granulocyte-macrophage progenitor; MEP, megakaryocyte ethryroid progenitor; PM_BM, promyeloblast, bone marrow; MY_BM; myelocyte, bone marrow.
Figure 13A:
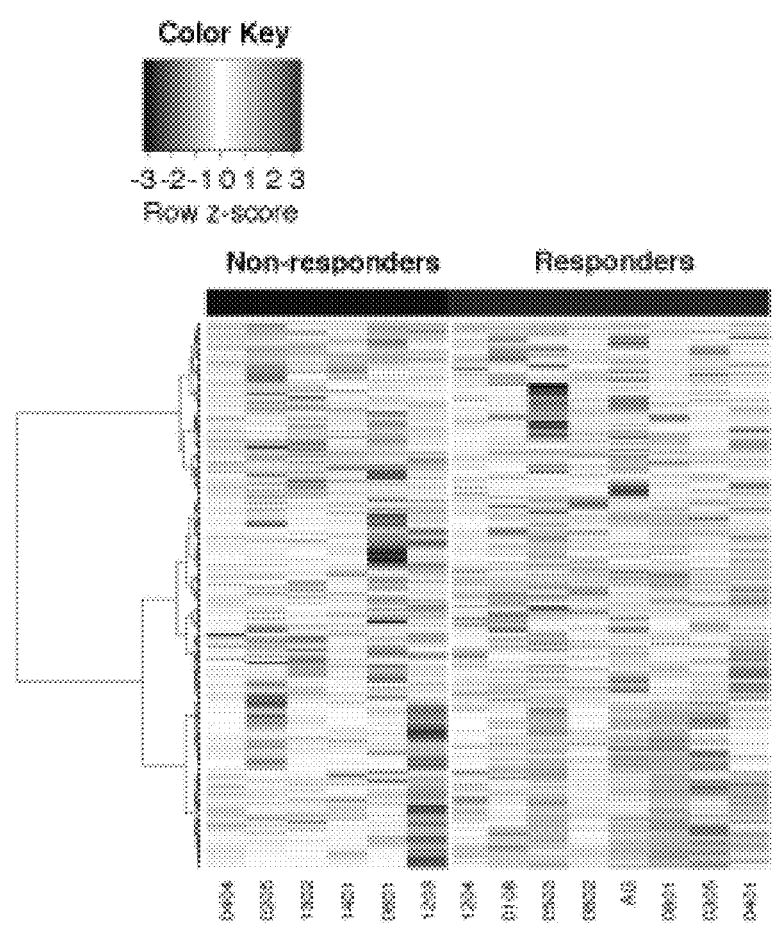
FIG. 13A-C: A specific transcriptional program is associated with response to DAC. A. Heat map illustrating gene expression differences between DAC-sensitive (indicated by dark red bar at the top) and DAC-resistant patients (indicated by the dark blue bar at the top). B. Enrichment plots for Gene Set Enrichment Analysis (GSEA) using the expression difference-ranked gene list showing enrichment for cell cycle-related gene sets. C. Box plots showing gene expression differences for CXCL4, CXCL7, and ITGβ3 (dark red box plots, responders; dark blue box plots, non-responders).

*SRSF2 mutational status was not available for all patients; the percentage was calculated based on the number of patients for whom mutational status was known.
[A]Fisher's exact test Example 5—Decitabine Sensitivity can be Linked to a Specific Transcriptional Program at Diagnosis While it has been previously shown that reduced expression of uridine-cytidine kinase, an enzyme involved in nucleoside metabolism, is associated with response to azacytidine in MDS (see, e.g., Valencia, A., et al., Leukemia. 2014; 28(3):621-628), it was not found that differential expression of this or other DMTi metabolizing enzymes is associated with response to DAC in CMML. Therefore, whether there are other transcriptional differences between DAC responders and non-responders that may be indicative of response and provide insight on functional pathways that contribute to DAC resistance was determined. RNA-seq was performed on 14 patients (8 responders and 6 non-responders) in the cohort of CMML patients for whom high-quality RNA was available. Prior to performing differential analysis the ability of the RNA-seq approach was validated to accurately detect quantitative variability by performing qRT-PCR on 13 of the 14 patient RNAs, and determining the degree of agreement between the two methods ($r=-0.85$, $R^2$ value: $0.73x$, p value $<0.0001$) (FIG. 12A). As shown in FIG. 13A, a direct comparison of the two groups of patients identified 601 genes with an absolute log 2 (fold change)>1 and p value <0.05. Notably, this gene signature consisted of a majority of genes overexpressed in DAC-sensitive patients (405 upregulated genes), with only a small proportion of genes were downregulated in these patients (Table 3).

Figure 13B:
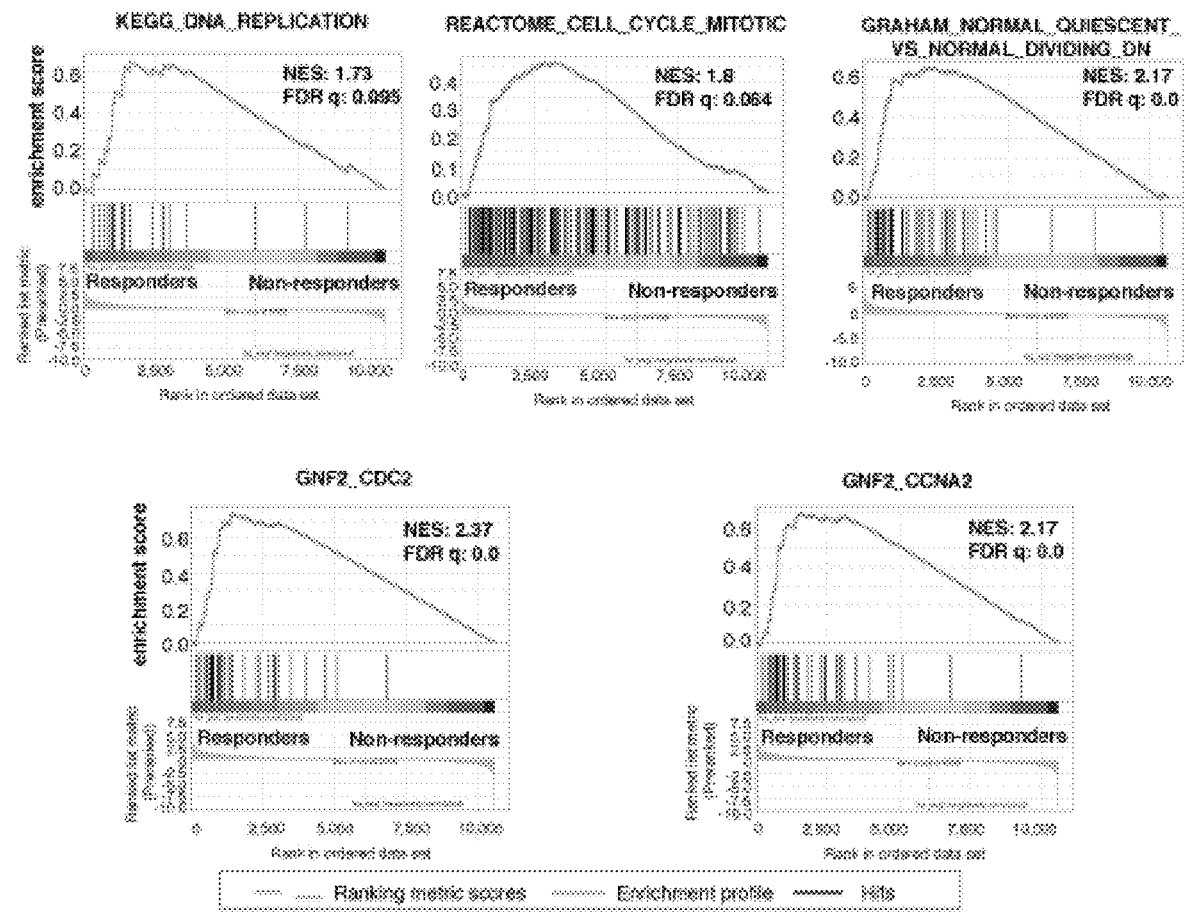

In order to identify biological differences that might explain the difference in therapeutic response to DAC between these patients, a Gene Set Enrichment Analysis (GSEA) (see, e.g., Subramanian, A., et al., Proc Natl Acad Sci USA. 2005; 102(43):15545-15550) was performed. Gene sets enriched in DAC-sensitive patients at an FDR<0.1 were involved in proliferation, cell cycle and DNA replication (FIG. 13B). Likewise, genes reported as being downregulated in quiescent versus dividing $CD34^+$ cells (see, e.g., Graham, S. M., et al., Stem Cells. 2007; 25(12):3111-3120) were found to be upregulated in DAC responders. This enrichment of gene sets involved in cell cycle and DNA replication in DAC-sensitive patients is consistent with the requisite of DAC incorporation into the DNA during S phase.

Example 6—Primary Resistance to Decitabine is Associated with Overexpression of ITGβ3 and the Chemokines CXCL4 and CXCL7

Figure 12B:
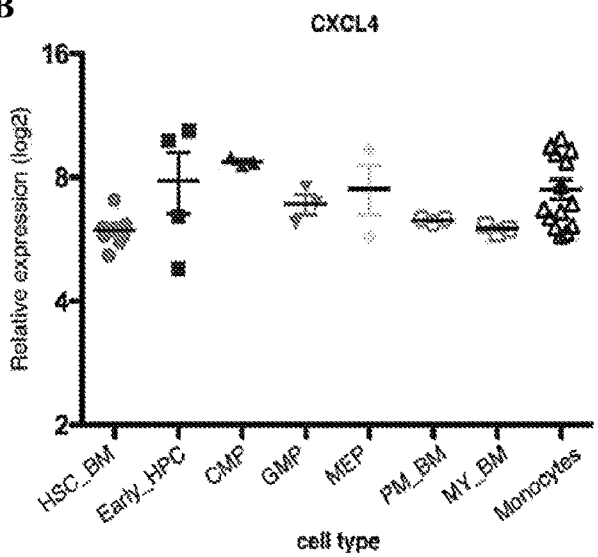
Figure 12C:
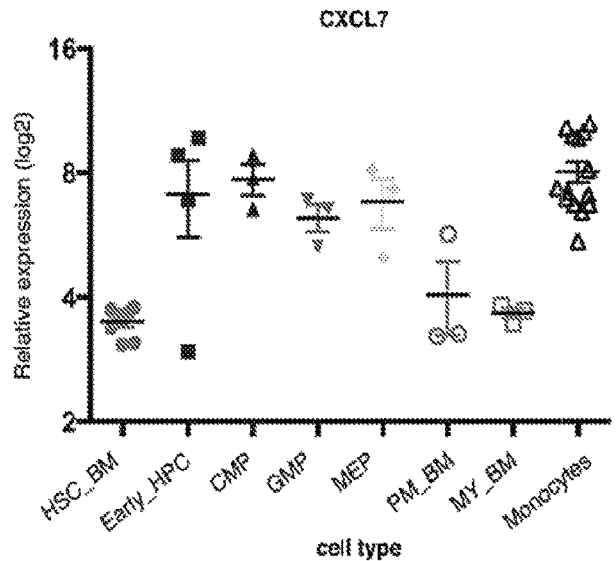
Figure 13C:
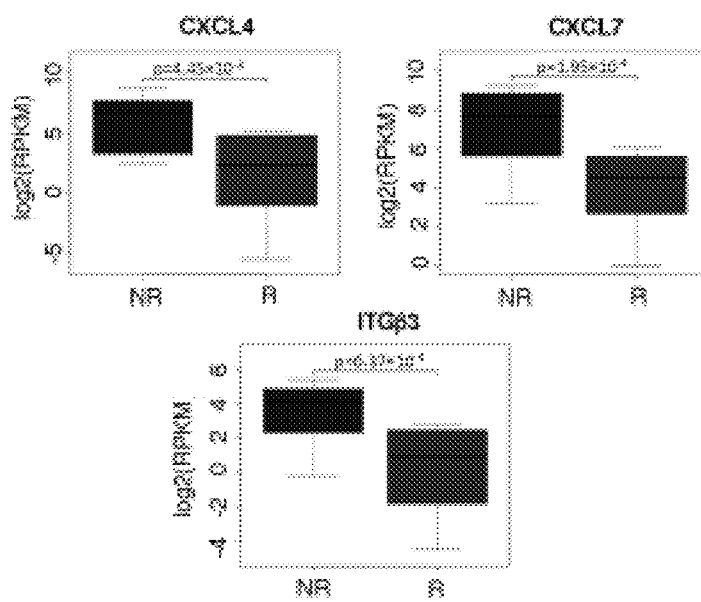
Figure 14A:
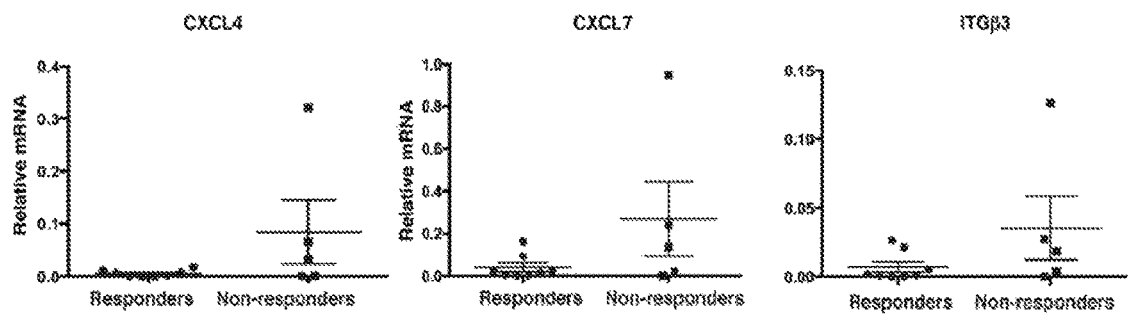
FIG. 14A-D: CXCL4 and CXCL7 are up-regulated in the bone marrow of non-responders. A. qRT-PCR showing validation of overexpression of CXCL4, CXCL7 and ITGβ3 in non-responders. B. Pearson correlation analysis of expression levels of CXCL7 and CXCL4 by RNA-seq (left panel) and qRT-PCR (right panel). C-D. Representative immunohistochemistry (IHC) images for CXCL4 (C) and CXCL7 (D) in diagnostic bone marrow biopsies in a DAC responder (top panels) and non-responder patients (bottom panels).
Figure 14B:
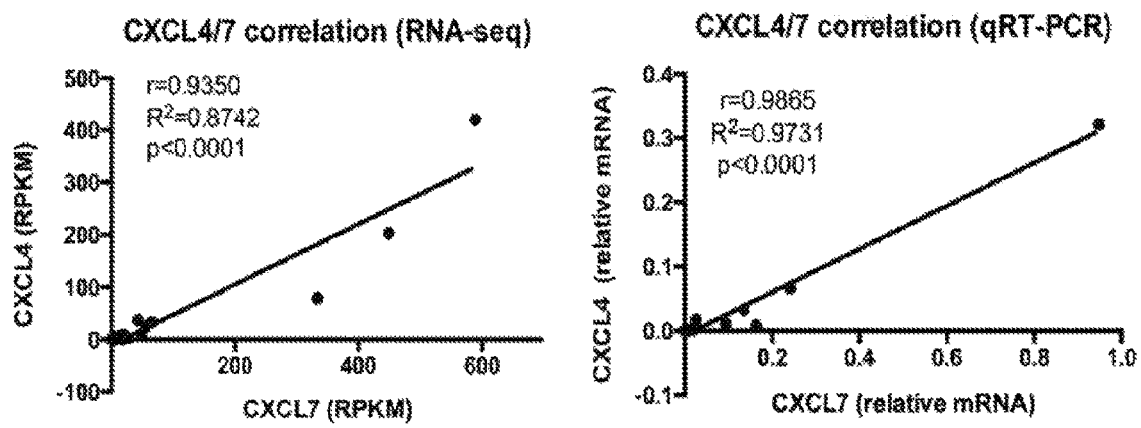
Figures 14C, 14D:
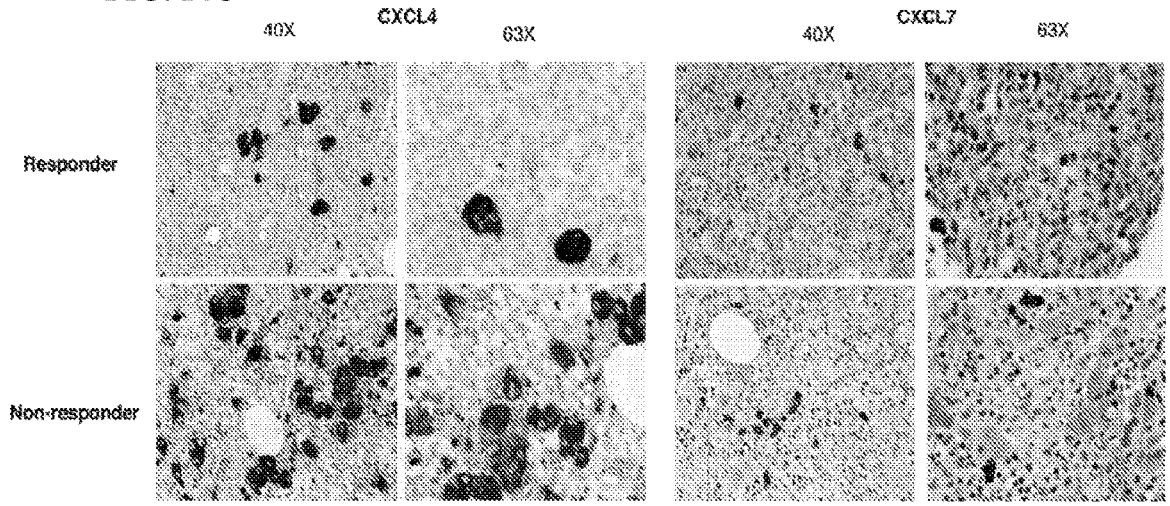

As mentioned before, only a small fraction of genes were found to have at least a two-fold overexpression in DAC-resistant patients. Among these, three genes that have previously been implicated in chemoresistance and leukemogenesis were overexpressed in non-responders: CXCL4 (also known as PF4), CXCL7 (also known as PPBP), and integrin beta 3 (ITGβ3) (FIG. 13C). Thus, it was hypothesized that overexpression of these genes might be a potential mechanism through which CMML acquires resistance to DAC. First, as shown in FIG. 14A, the overexpression of these genes in DAC-resistant patients by qRT-PCR was validated. Notably, there was a statistically significant linear correlation between the levels of CXCL4 and CXCL7 expression by both RNA-seq ($r=0.9350$, $R^2=0.87$, $p<0.0001$) and qRT-PCR ($r=0.9865$, $R^2=0.9731$, $p<0.0001$), suggesting these factors may act in concert in the bone marrow microenvironment (FIG. 14B). While both chemokines were originally thought to be produced exclusively by megakaryocytes, there is evidence that monocytes (see, e.g., Schaffner, A., et al., J Leukoc Biol. 2005; 78(1):202-209; Pillai, M. M., et al., Blood. 2006; 107(9):3520-3526) and other cells within the bone marrow also produce CXCL4 and CXCL7 (see, e.g., Bagger, F. O., et al., Nucleic Acids Res. 2013; 41(Database issue):D1034-1039; Bagger, F. O., et al., Blood. 2012; 119(26):6394-6395) (FIG. 12B; FIG. 12C). To further confirm the overexpression of these chemokines in non-responder patients as well as to determine the cellular source and localization of the proteins in the bone marrow, immunohistochemistry (IHC) was performed on a subset of paraffin-embedded bone marrow biopsies taken at diagnosis from responders and non-responders. As shown in FIG. 14C and FIG. 14D, CXCL4 is primarily localized to megakaryocytes, while CXCL7 staining is stronger in a mononuclear cell population compatible with a monocytic origin. Importantly, there is increased CXCL4 and CXCL7 staining in non-responder patient bone marrow as compared with that of responder bone marrow, confirming the presence of CXCL4 and CXCL7 proteins in the bone marrow microenvironment that, like the mRNA levels, are increased in DAC-resistant patients.

Figure 15:
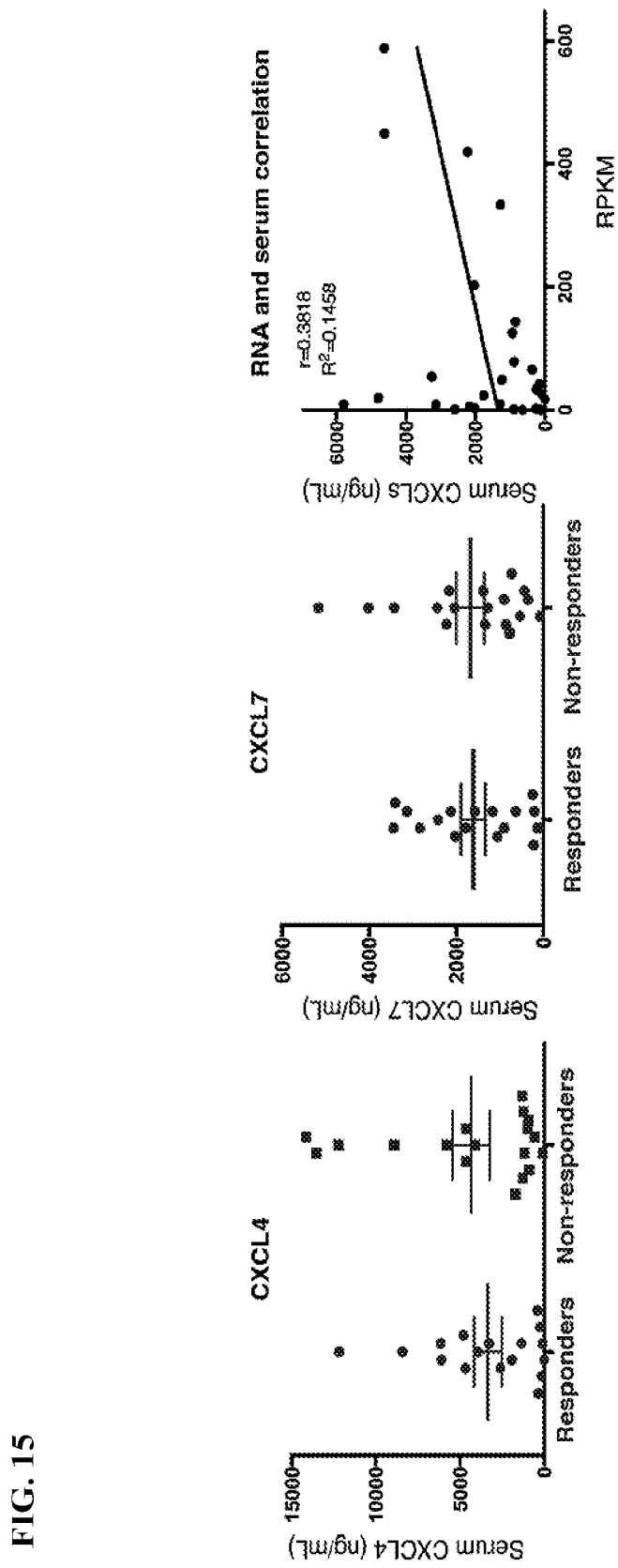
FIG. 15: Serum levels of CXCL4 and CXCL7 are not different in Decitabine responders and non-responders. Left and middle panels: Enzyme-linked immunosorbent assays (ELISAs) for CXCL4 and CXCL7. Right panel: Correlation between levels CXCL4/7 mRNA by RNA-seq (RPKM) and serum levels by ELISA (ng/mL protein).

Previous studies have implicated serum levels of these two chemokines as potential prognostic markers in MDS (see, e.g., Aivado, M., et al., Proc Natl Acad Sci USA. 2007; 104(4):1307-1312; Chen, C., et al., Leukemia. 2010; 24(11): 1875-1884). To determine if serum levels of CXCL4 and CXCL7 could serve as potential biomarkers for DAC response the serum concentrations of these chemokines by ELISAs in 35/40 CMML patients was first determined (FIG. 15). There was no significant difference in serum CXCL4 and CXCL7 levels between responders and non-responders.

In addition, no significant correlation between bone marrow mRNA levels and serum protein levels for these two chemokines was found indicating that serum levels of these chemokines are not reflective of mRNA expression in the bone marrow, mirroring previous observations documented for other chemokines in the bone marrow and serum of AML patients (see, e.g., Reikvam, H., et al., Toxins (Basel). 2013:5(2):336-362; Kittang, A. O., et al., Curr Top Microbiol Immunol. 2010:341(149-172.

Figure 16A:
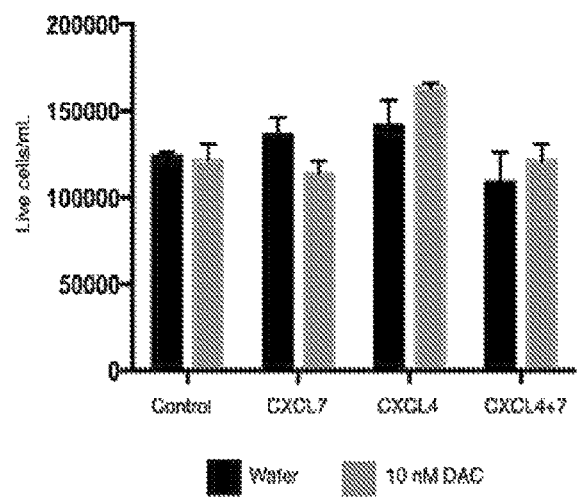
FIG. 16A-C: Low-dose Decitabine (DAC) does not impact CD34$^+$ cell proliferation, viability, and apoptosis. A-B. Low-doses of DAC do not affect cell proliferation, viability, or apoptosis with or without CXCL4 and 7. CD34$^+$ cells were treated with one dose of CXCL4, CXCL7, or both (50 ng/mL each) or vehicle (PBS/0.1% BSA) and daily doses of 10 nM DAC for 3 days. After 3 days, live cell number (A) and viability (B) were assessed by trypan blue exclusion, and apoptosis (C) was analyzed by Annexin V and propodium iodide staining. The results shown are from one representative experiment out of two independent experiments.
Figure 16B:
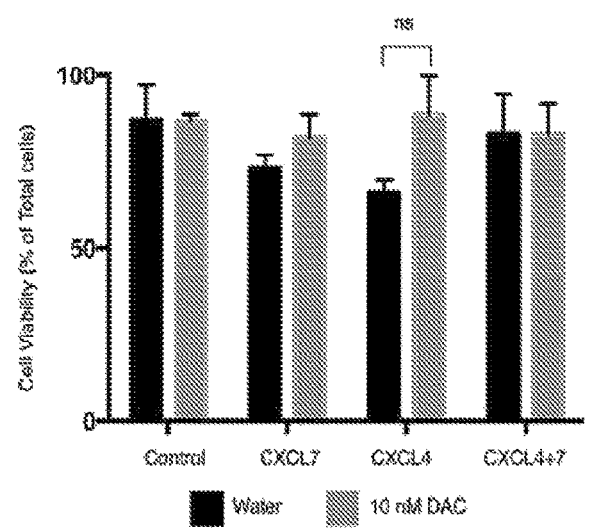
Figure 16C:
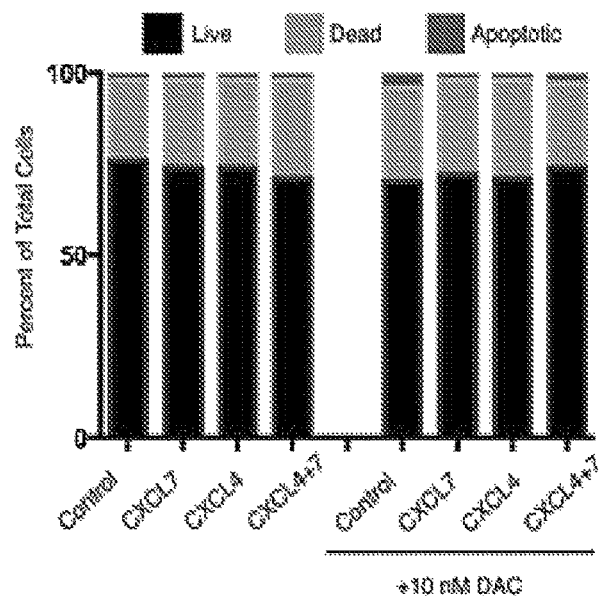
Figure 17A:
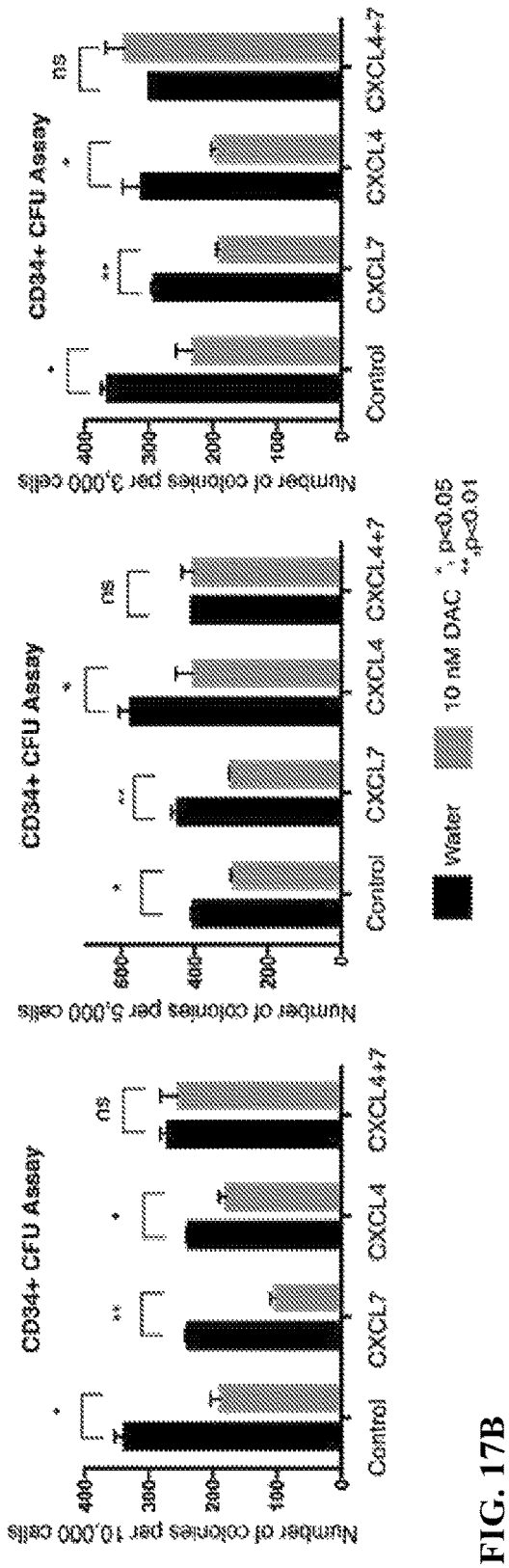
FIG. 17A-B: CXCL4 and 7 promote resistance to Decitabine (DAC) in CD34$^+$ and primary CMML specimens. A. Colony formation is inhibited by DAC but restored with the combination of CXCL4 and CXCL7. CD34$^+$ cells were treated with one dose of CXCL4, CXCL7, or both (50 ng/mL each) or vehicle (PBS/0.1% BSA) and daily doses of 10 nM DAC for 3 days. After 3 days of in vitro treatment with DAC, the cells were plated in methylcellulose and incubated for 12-15 days before colonies were counted. Data represent mean+standard deviation (SD). Treatment with 10 nM DAC significantly decreased colony formation (by unpaired t-test; p<0.05) but failed to do so in the presence of CXCL7 and CXCL4 together. Shown in the three panels are the results of three independent experiments. B. CXCL4 and CXCL7 abrogate the effect of DAC on the viability of primary CMML MNC. CMML MNC were treated in vitro for 72 h with 10 nM DAC alone or in the presence of 50 ng/mL of CXCL4, CXCL7, or both. Data represent mean+ standard deviation (SD). Treatment with DAC alone significantly reduced the viability of these cells (by unpaired t-test), but this effect was lost when CXCL4 or CXCL7 were added to the culture.

Example 7—CXCL4 and CXCL7 Abrogate the Effect of Decitabine on Hematopoietic Cells It has been previously reported that both CXCL4 and CXCL7 can reduce the chemosensitivity of bone marrow cells to 5-fluorouracil in vitro (see, e.g., Han, Z. C., et al., Blood. 1997; 89(7):2328-2335), and CXCL4 has been implicated in cell cycle arrest (see, e.g., Gupta, S. K., and Singh, J. P. J Cell Biol. 1994; 127(4):1121-1127) and quiescence (see, e.g., Dudek, A. Z., et al., Blood. 2003; 101 (12):4687-4694; Bruns, et al., Nat. Med. 2014), which might be a mechanism through which it acts to prevent sufficient incorporation of DAC into cells of non-responders. Therefore, it was hypothesized that overabundance of CXCL4 and CXCL7 in the bone marrow microenvironment may act to overcome the effects of DAC. To test this, primary human $CD34^+$ cells were cultured for 3 days in vitro with CXCL4 (50 ng/mL), CXCL7 (50 ng/mL) or a combination of both chemokines in either the presence or absence of low-dose DAC (10 nM) and then plated them in methylcellulose to test their clonogenic potential. The chemokines and low-dose DAC did not affect cell proliferation during the in vitro liquid culture period (FIG. 16A). Moreover, as previously reported, low-dose DAC did not reduce cell viability or induce apoptosis after 3 days in culture (FIG. 16B; FIG. 16C) (see, e.g., Tsai, H. C., et al., Cancer Cell. 2012; 21(3):430-446). However, 3 days of 10 nM DAC significantly reduced colony formation (FIG. 17A). Addition of either CXCL4 or CXCL7 alone did not have a significant impact on DAC-induced colony inhibition. However, concomitant treatment of $CD34^+$ cells with CXCL4 and CXCL7 completely abolished the suppressive effect of DAC on colony formation.

Figure 17B:
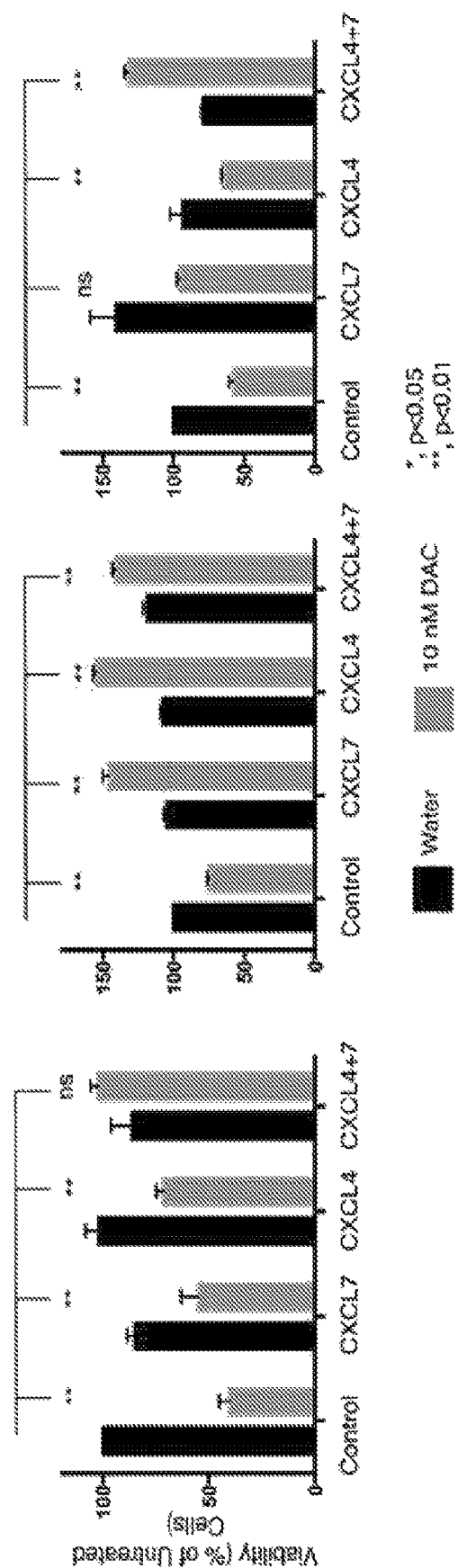

Finally, the ability of CXCL4 and CXCL7 to induce resistance in primary CMML cells was tested. BM MNC from diagnostic specimens collected from 3 patients known to be sensitive to DAC were placed in liquid culture and treated for 72 h with 10 nM DAC in the presence or absence of 50 ng/mL of CXCL4, CXCL7 or a combination of both. Viability was assessed after 72 hours. Unlike normal CD34' cells, which do not show diminished viability with 10 nM DAC (FIG. 12B), treatment of primary CMML cells with low-dose DAC did lead to a significant decrease in viability in all three patients. However, concomitant treatment of CMML cells with CXCL4, CXCL7 or their combination abrogated the effect of DAC on all three patients who were otherwise DAC-sensitive (FIG. 17B). In combination, these data support the hypothesis that the presence of excess CXCL4 and CXCL7 in the marrow microenvironment contributes to inducing DAC resistance in CMML cells.

Example 8—Materials and Methods for Examples 1-7

Sample Collection and Processing:
FISM Cohort:
Bone marrow specimens were collected before treatment from 40 patients with CMML who gave their informed consent. Bone marrow mononuclear cells (BM MNC) were isolated through Ficoll density centrifugation and viably frozen in 10% DMSO+90% FBS. Patients with advanced CMML were enrolled in the non randomized NCT01251627 clinical trial from the Fondazione Italiana per le Sindromi Mielodisplastiche (FISM) and they all received DAC as a single agent 20 $mg/m^2$/day IV×5 days every 28 days for at least 6 cycles prior to being classified as responders or non-responders, with response defined as hematological improvement or better according to IWG 2006 criteria (see, e.g., Cheson, B. D., et al., Blood. 2006; 108(2):419-425). Table 1 summarizes the patients' characteristics. Genomic DNA and total RNA were isolated using the AllPrep DNA/ RNA kit from Qiagen (Valencia, Calif.) according to manufacturer's instructions.
GFM Cohort:
The patients were enrolled in the EudraCT #2008-000470-21 trial (#NCT01098084 at ClinicalTrials.gov) from the GFM and received DAC 20 $mg/m^2$/day IV×5 days every 28 days for at least 3 cycles. Blood samples were collected using EDTA—containing tubes, mononucleated cells were isolated on Ficoll-Hypaque, and monocytes were enriched using the AutoMacs system (Miltenyi Biotec) through negative selection with microbeads conjugated to antibodies targeting CD3, CD7, CD16, CD19, CD56, CD123, and glycophorin A, then further enriched by positive selection with microbeads conjugated to a monoclonal mouse anti-human CD14 antibody (Miltenyi Biotec). Genomic DNA was extracted from the monocytes using the Norgen Biotek kit (Thorold, Ontario, Canada) kit according to the manufacturer's instructions. The patients' characteristics are summarized in Table 2.
Mutational Sequencing:
Target capture: Capture of the target regions (exons plus splice junctions) were carried out using a custom design HaloPlex Target Enrichment kit (Agilent, Santa Clara, Calif.), according to the HaloPlex Target Enrichment System-Fast Protocol Version D.5. Sequencing: 500 ng of DNA (quantified using a Qubit Fluorometer, Invitrogen, Carlsbad, Calif.) from each sample were used in the capture reaction. Each sample had a unique index. Libraries were quantified by Qubit and pooled, and run in an Illumina HiSeq 2500 rapid run flow cell using the onboard cluster method, as paired-end sequencing (2×100 bp reads). Analysis: Sequencing results were demultiplexed and converted to FASTQ format using Illumina Bcl2FastQ software. The reads were adapter and quality trimmed with Trimmomatic (see, e.g., Bolger, A. M., Lohse, M., and Usadel, B. Bioinformatics. 2014) and then aligned to the human genome (UCSC build hg19) using the Burrows-Wheeler Aligner (BWA) (see, e.g., Li, H., and Durbin, R. Bioinformatics. 2009; 25(14):1754-1760). Further local indel realignment and base-quality score recalibration and were performed using the Genome Analysis Toolkit (GATK) (see, e.g., DePristo, M. A., et al., Nat Genet. 2011; 43(5):491-498). Single-nucleotide variation and indel calls were generated with GATK Haplotype-Caller. ANNOVAR (see, e.g., Wang, K., Li, M., and Hakonarson, H. Nucleic Acids Res. 2010; 38(16):e164) was used to annotate variants with functional consequence on genes as well as identifying presence in dbSNP 137, 1000 Genomes project, ESP6500 (National Heart, Lung, and Blood Institute (NHLBI) GO Exome Sequencing Project), and COSMIC 67.

Genome-Wide DNA Methylation by ERRBS:

25 ng of high-molecular weight genomic DNA were used to perform the ERRBS assay as previously described (see, e.g., Akalin, A., et al., PLoS Genet. 2012; 8(6):e1002781) and sequenced on a HiSeq2000 Illumina sequencer. Reads were aligned against a bisulfite-converted human genome (hg18) using Bowtie and Bismark (see, e.g., Krueger, F., and Andrews, S. R. Bioinformatics. 2011; 27(11):1571-1572). Downstream analysis was performed using R statistical software version 3.0.3 (see, e.g., Team, R. D. C. 2012. R: A language and environment for statistical computing. Vienna: R Foundation for Statistical Computing), Bioconductor 2.13 (see, e.g., Gentleman, R. C., et al., Genome Biol. 2004; 5(10):R80) and the MethylSig 0.1.3 (see, e.g., Park, Y., et al., Bioinformatics. 2014) package. Only genomic regions with coverage between 10× and 500× were used for the downstream analysis. Differentially methylated regions (DMR) were identified by first summarizing the methylation status of genomic regions into 25-bp tiles and then identifying regions with absolute methylation difference ≥25% and false discovery rate (FDR)<10%. DMRs were annotated to the RefSeq genes using the following criteria: (i) DMRs overlapping with a gene were annotated to that gene, (ii) intergenic DMRs were annotated to all neighboring genes within a 50-kb window, and (iii) if no gene was detected within a 50-kb window, then the DMR was annotated to the nearest TSS.

Methylation Classifier:

Support vector machine (SVM) (see, e.g., Cortes, C., and Vapnik, V. Machine Learning. 1995; 20(3):273-297) was applied and implemented by R package e1071 (see, e.g., e1071: Misc Functions of the Department of Statistics (e1071), TU Wien. http://, followed by, cran.r-project, followed by, .org/package=e1071, 2008) to classify the two groups of patients (responder and non-responder), in which the percentage methylation of 25 bp tiles were used as predictors. The probability mode and sigmoid kernel were used in the svm function, otherwise the default parameters were applied. Two-step feature selections for the SVM classifier were performed: (i) 25 bp tiles were pre-filtered by the nominal p-values <0.05 and absolute methylation >20% calculated by MethylSig package (50); (ii) greedy forward feature selection was applied on the remaining tiles. Briefly, the predictability of each of the filtered tiles in the SVM model were assessed and prioritized, and then sequentially evaluated the combinatorial predictability of tiles by adding one from the prioritized tiles into the classifier at a time. The set of tiles that can optimally predict patient response were selected as the final predictors of the SVM classifier. The predictability was assessed based on 10-fold cross-validation. Specifically, the 39 samples for which ERRBS libraries were available were randomly partitioned into 10 complementary subsets, training the SVM model on 9 out of the 10 subsets (called the training set), and predicting the classes (responder or non-responder) on the 1 left-out subset (called the validation set or testing set). To reduce variability, 10 rounds of cross-validation were performed using different partitions, and the validation results were summarized over the rounds. During each round of validation, the probability of each sample being predicted as responder was recorded and then the area under receiver operating characteristic (ROC) curve (AUC) across 10 rounds was calculated by R package ROCR (see, e.g., Sing, T., et al., Bioinformatics. 2005; 21(20):3940-3941), which was used as the assessment of the predictability. Complete code supplied at FIG. 14.

EpiTYPER MassARRAY:

Validation of CpG methylation of select genomic regions was performed by MALDI-TOF using EpiTYPER MassARRAY (Sequenom, San Diego, Calif.) (see, e.g., Ehrich, M., et al., Proc Natl Acad Sci USA. 2005; 102(44):15785-15790) on bisulfite-converted genomic DNA from a subset of DAC responders and non-responders. The primers used to amplify these genomic regions and the resultant amplicon sequences are listed in FIG. 18. FIG. 19 provides the primers and amplicon sequences for the EpiTYPER MassARRAY validation of ERRBS and the MAPK signaling pathway.

RNA Sequencing:

RNA-seq was performed on RNA from 14 patient samples (8 responders, 6 non-responders) that had high quality RNA (RNA integrity number of >6 as determined by the Agilent 2100 Bioanalyzer). RNA-seq libraries were prepared using the Illumina TruSeq RNA Sample Prep Kit v2 as per manufacturer's instructions (San Diego, Calif.). A set of synthetic RNAs from the External RNA Control Consortium (ERCC) (see, e.g., Jiang, L., et al., Genome Res. 2011; 21(9):1543-1551) at known concentrations were mixed with each of the cDNA libraries. Four separate samples were multiplexed into each lane and sequenced on a HiSeq2000 sequencer. Quality of reads obtained was evaluated using FastQC (http://, followed by, www.bioinformatics, followed by, .babraham.ac.uk/, followed by, projects/fastqc/). The sequenced libraries were aligned to the human genome (hg18) or to the ERCC spike-in reference sequence using TopHat (v2.0.8) (see, e.g., Trapnell, C., et al., Nat Biotechnol. 2013; 31(1):46-53) with default parameters.

RNA-Seq Analysis:

HTSeq (0.5.4p5) (see, e.g., Anders, S., Pyl, P. T., and Huber, W. HTSeq – A Python framework to work with high-throughput sequencing data. bioRxiv. 2014) was used to generate the count matrix with the following parameters: 'htseq-count--mode=union--stranded=no' using two GTF annotation files respectively: 1) the hg18 RefSeq gene GTF file downloaded from the UCSC genome browser for endogenous gene assembly; 2) the ERCC spike-in transcript GTF file downloaded from the official website (http:, followed by, //ww, followed by, w.lifetechnologies., followed by, com/order/catalog, followed by, /product/4456740) for ERCC spike-in assembly. The counts of endogenous genes were normalized by ERCC spike-in library size, and the differential expression analysis was performed using edgeR (v3.4.2) (see, e.g., Robinson, M. D., et al., Bioinformatics. 2010; 26(1):139-140) GLM model. Genes with absolute log 2 (fold change)>1 and p value <0.05 were reported.

Quantitative Reverse Traneciptase PCR (qRT-PCR):

To validate the RNA-seq results, RNA from selected non-responder and responder patients was reverse-transcribed using the Verso cDNA synthesis kit (Thermo Scientific, Waltham, Mass.) as per the manufacturer's instructions with random hexamer primers. qPCR was performed on the resulting cDNA in triplicate using intron-spanning/-flanking primer sets with Fast SYBR Green Master Mix and the StepOne Plus PCR system (Applied Biosystems) as per the manufacturer's instructions. Primer sequences are listed FIG. 20.

Enzyme-Linked Immunoeorbent Assays (ELISAs):

ELISAs for CXCL4 and CXCL7/NAP-2 on serum from the CMML patients were performed using the corresponding ELISA kits (RAB0402 and RAB0135) from Sigma-Aldrich (St. Louis, Mo.) per the manufacturer's directions. For CXCL4, the serum was diluted 1:500 in the sample dilution buffer provided in the kit.

Immunohistochemistry (IHC):

For immunostaining, 3-μm-thick formalin-fixed, paraffin-embedded BM sections were deparaffinized in xylenes and hydrated in graded alcohols. Antigen retrieval was performed in ethylenediaminetetraacetic acid buffer (EDTA, 1 mM, pH 8.0) for two 15-minute cycles at max power in a microwave oven, and slides were then incubated with a CXCL4 antibody (Peptrotech #500-P05, 1:300) or with a CXCL7 antibody (Biorbyt orb 13423: 1:50). Immunostaining was performed with the BenchMark histostainer (Roche-Ventana Medical Systems, Tucson, Ariz.) using a peroxidase detection kit with 3,3-diaminobenzidine substrate according to standard procedures and then the sections were counterstained with hematoxylin.

Cell Culture and Colony Forming Assays:

CD34+ cells were isolated from cryopreserved BM MNC from femoral head specimens using the Miltenyi Biotec CD34 microbead isolation kit (San Diego, Calif.) per the manufacturer's instructions. For CMML cells, the cryopreserved BM MNC were rapidly thawed at 37° C. and treated with DNAse to prevent cell clumping. Cells were plated in pre-stimulation media (IMDM with 20% BIT (Stem Cell Technologies, Vancouver, BC, Canada), IL-6 (20 ng/mL), SCF (100 ng/ml), TPO (100 ng/mL), FLT3L (10 ng/mL); Peprotech, Rocky Hill, N.J.) and recovered overnight. The following day the CXCL4 (Peprotech; 50 ng/mL), CXCL7 (Peprotech; 50 ng/mL), a combination of both chemokines (50 ng/mL each), or vehicle (PBS/0.1% BSA) were added as well as freshly prepared 10 nM DAC (Sigma-Aldrich) or vehicle (water). The DAC was replenished daily for a total of 3 days. Live cell number and viability were determined by trypan blue exclusion. For colony assays, an equal number of live, treated CD34+ cells were plated in duplicate in H4435 Enriched Methocult (Stem Cell Technologies). Colonies were counted after 12 to 15 days.

Apoptosis Assays:

Apoptosis was assessed using the Tali Apoptosis Kit with Annexin V Alexa Fluor 288 and propidium iodide per the manufacturer's instructions and was measured on a Tali imaged-based cytometer (Life Technologies, Carlsbad, Calif.).

Accession Numbers:

FISM cohort ERRBS and RNA-seq data are available for download from the Gene Expression Omnibus (GEO) database under accession number GSE61163. GFM cohort ERRBS data are available from GEO under accession number GSE63787.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method for characterizing a biological sample comprising:
   a) extracting genomic DNA from a biological sample of a human individual having or suspected of having chronic myelomonocytic leukemia (CMML),
   b) treating the extracted genomic DNA with bisulfite,
   c) providing primers specific for AGRN, providing primers specific for the EHD3, providing primers specific for GLI2, providing primers specific for 1-Mar, providing primers specific for QKI, providing primers specific for PDE10A, providing primers specific for MAD1L1 providing primers specific for MIR4472-1, providing primers specific for LHX2, providing primers specific for RXRA, providing primers specific for APLNR, providing primers specific for PACS2, providing primers specific for KLF13, providing primers specific for CLCN7, providing primers specific for NTHL1, providing primers specific for CHST5, providing primers specific for STRN4, providing primers specific for NOSIP, providing primers specific for SULF2, providing primers specific for SLC25A1, providing primers specific for NRK,
   d) amplifying the bisulfite-treated genomic DNA with the primers specific for AGRN, primers specific for EHD3, primers specific for GLI2, primers specific for QKI, primers specific for PDE10A, primers specific for MAD1LI, primers specific for MIR4472-1, primers specific for LHX2, primers specific for RXRA, primers specific for APLNR, primers specific for PACS2, primers specific for KLF13, primers specific for CLCN7, primers specific for NTHL1, primers specific for CHST5, primers specific for STRN4, primers specific for NOSIP, primers specific for SULF2, primers specific for SLC25A1, and primers specific for NRK, and
   e) measuring the methylation level of the bisulfite-treated genomic DNA amplified with the primers specific for AGRN, primers specific for EHD3, primers specific for GLI2, primers specific for QKI, primers specific for PDE10A, primers specific for MAD1LI, primers specific for MIR4472-1, primers specific for LHX2, primers specific for RXRA, primers specific for APLNR, primers specific for PACS2, primers specific for KLF13, primers specific for CLCN7, primers specific for NTHL1, primers specific for CHSTS, primers specific for STRN4, primers specific for NOSIP, primers specific for SULF2, primers specific for SLC25A1, and primers specific for NRK in the genes selected from AGRN, EHD3, GLI2, QKI, PDE10A, MAD1LI, MIR4472-2, LHX2, RXRA, APLNR, PACS2, KLF13, CLCN7, NTHL1, CHST5, STRN4, NOSIP, SULF2, SLC25A1, and NRK by methylation-specific PCR, quantitative methylation-specific PCR, methylation sensitive DNA restriction enzyme analysis or bisulfite genomic sequencing PCR.

2. The method of claim 1, wherein the biological sample is from a human diagnosed with chronic myelomonocytic leukemia.

3. The method of claim 1, wherein biological sample is a bone marrow sample, a stool sample, a tissue sample, a colorectal cyst sample, a colorectal tumor sample, a blood sample, or a urine sample.

* * * * *

SEQUENCE LISTING

```
<160> NUMBER OF SEQ ID NOS: 41

<210> SEQ ID NO 1
<211> LENGTH: 35
<212> TYPE: DNA
<213> ORGANISM: Artificial sequence
<220> FEATURE:
<223> OTHER INFORMATION: synthetic

<400> SEQUENCE: 1
aggaagagag agaagggttt tagagagaag agtgg                              35

<210> SEQ ID NO 2
<211> LENGTH: 57
<212> TYPE: DNA
<213> ORGANISM: Artificial sequence
<220> FEATURE:
<223> OTHER INFORMATION: synthetic

<400> SEQUENCE: 2
cagtaatacg actcactata gggagaaggc tcaaaaataa aaacaccat ttattcc      57

<210> SEQ ID NO 3
<211> LENGTH: 399
<212> TYPE: DNA
<213> ORGANISM: Homo sapiens

<400> SEQUENCE: 3
agaagggccc cagagagaag agtggggacg caaaggaaag atgggcagga tgggatggac    60
agactgagat ggaaaggccg acagggctta gccgccaagc tcgaaggaag cgcgggaggc   120
cgggcgccgg gcgaggatgg gctgggcatg agctgcgggc cgcgggcagg gcgggacacc   180
```

```
aaggcgcggg cggtggtggc gggcaggggg ctccgcgcgg ggctgcgccg ctgtccgggg    240
taatttttca tctcggccgg ctaatctttg ttcccggcga agataatgaa tagccagtcg    300
ttatctgccc ggctcccgga ggctgcccga gaatggggtt gtacagggct gggaattgtt    360
tccaaagtgc cgcggaataa atggtgttcc ttatctctg                          399
```

<210> SEQ ID NO 4
<211> LENGTH: 37
<212> TYPE: DNA
<213> ORGANISM: Artificial sequence
<220> FEATURE:
<223> OTHER INFORMATION: synthetic

<400> SEQUENCE: 4

```
aggaagagag ttattggtta gagatgattt gatgatg                             37
```

<210> SEQ ID NO 5
<211> LENGTH: 56
<212> TYPE: DNA
<213> ORGANISM: Artificial sequence
<220> FEATURE:
<223> OTHER INFORMATION: synthetic

<400> SEQUENCE: 5

```
cagtaatacg actcactata gggagaaggc ttaaatacct aaacaaaaac caaacc        56
```

<210> SEQ ID NO 6
<211> LENGTH: 491
<212> TYPE: DNA
<213> ORGANISM: Homo sapiens

<400> SEQUENCE: 6

```
ccactggcca gagatgattt gatgatgccc ttcgggactt actggcgagg gacttaggca    60
gagacgccca gacacgaaac ggggctcggc ccagggctct ttcctcccca gcagccccgc   120
gtcccgaggt cggggagctc agagacacta gcacaggagc cccagacgca ttcagggcgc   180
accccagaac tccggagccg gtttgggcat ccttgtggag cgggactggg tgtgtgcagt   240
gcgccccgct ccaccgctgg tattggctgt gtgtgaggtt ttgttttgtt ttgttttgtt   300
ttgttttgtt ttgttttgtt ttgttttgta agaaataaat gcacagacgc ttgcaaagct   360
ccgggctccc ctgaagctgc ggaagccccc agatgggagc aggcggggag aaaagttggg   420
gaacaggcga gggcaagggg gcaaagccga aggaggttgc agcgctggcc tggtccctgc   480
ccaggcatct a                                                        491
```

<210> SEQ ID NO 7
<211> LENGTH: 35
<212> TYPE: DNA
<213> ORGANISM: Artificial sequence
<220> FEATURE:
<223> OTHER INFORMATION: synthetic

<400> SEQUENCE: 7

```
aggaagagag tttagagggg tttttttgttt ttttt                              35
```

<210> SEQ ID NO 8
<211> LENGTH: 55
<212> TYPE: DNA
<213> ORGANISM: Artificial sequence
<220> FEATURE:
<223> OTHER INFORMATION: synthetic

<400> SEQUENCE: 8

| cagtaatacg actcactata gggagaaggc taaccccaaa tctaccccta aatac | 55 |

<210> SEQ ID NO 9
<211> LENGTH: 309
<212> TYPE: DNA
<213> ORGANISM: Homo sapiens

<400> SEQUENCE: 9

| tccagagggg ttttttgctt cctcccccttt ccaacgtcta aactgtccca gagaacgccc | 60 |
| atttccccca ctatttgtga gcgcagggtg ctcgcaaaga agaggaggaa ggaggaaggc | 120 |
| aggggaggga gaacggcaag gagagctccg cagggctggg agaaatgaga ccaagagaga | 180 |
| ctggagagg gcgcagaga agagaggggg gaccgagagc cgcgtccccg cggtcgcgtg | 240 |
| gatttagaaa aaggctggct ttaccatgac ttatgtgcag cttgcgcatc caggggtaga | 300 |
| tctggggtt | 309 |

<210> SEQ ID NO 10
<211> LENGTH: 35
<212> TYPE: DNA
<213> ORGANISM: Artificial sequence
<220> FEATURE:
<223> OTHER INFORMATION: synthetic

<400> SEQUENCE: 10

| aggaagagag tttagtaaag agttaaaggg agggg | 35 |

<210> SEQ ID NO 11
<211> LENGTH: 56
<212> TYPE: DNA
<213> ORGANISM: Artificial sequence
<220> FEATURE:
<223> OTHER INFORMATION: synthetic

<400> SEQUENCE: 11

| cagtaatacg actcactata gggagaaggc tctaacaata aacaacccct caaaaa | 56 |

<210> SEQ ID NO 12
<211> LENGTH: 493
<212> TYPE: DNA
<213> ORGANISM: Homo sapiens

<400> SEQUENCE: 12

| cccagcaaag agttaaaggg aggggacgtg ggctgtcacg cgtcattggg cagattatgt | 60 |
| gcagcaaaca aaaagtgtgt gtctgcgtgc cagtcagtca ctgcatcggg tccatctgta | 120 |
| caactctctc cgtttctccg tctctctccc tccctccctc cctccacccc ccaatctttt | 180 |
| ttctccccat ctctccatct ctctcttatc tcttcaggaa gagcctaaaa ggcggcaaca | 240 |
| ccaacacctc ttgacatgga aatacactga tacaataggc aaaaggaaac actcgattgc | 300 |
| atcttcccgg ttccaggtgg ccttatttgg gagattctat actgacccta ttcctggtaa | 360 |
| gtctatttgc attgatgtgg gaggggggatg ggaggaagac agtttggtgg aaagagtaga | 420 |
| acattttgtc ttccgtctcc ttattatcca gaagagagag aaaaataatt cttgaggggc | 480 |
| tgtctactgc cag | 493 |

<210> SEQ ID NO 13
<211> LENGTH: 35
<212> TYPE: DNA
<213> ORGANISM: Artificial sequence

```
<220> FEATURE:
<223> OTHER INFORMATION: synthetic

<400> SEQUENCE: 13
aggaagagag ttttggggta tattttttagg gtagg                              35

<210> SEQ ID NO 14
<211> LENGTH: 57
<212> TYPE: DNA
<213> ORGANISM: Artificial sequence
<220> FEATURE:
<223> OTHER INFORMATION: synthetic

<400> SEQUENCE: 14
cagtaatacg actcactata gggagaaggc tcctaatcat ttttaccccca tacaaaa      57

<210> SEQ ID NO 15
<211> LENGTH: 485
<212> TYPE: DNA
<213> ORGANISM: Homo sapiens

<400> SEQUENCE: 15
ctctggggta tattcccagg gcaggcggat aagaacctgg gcctagagcg gggcacggag     60
ctgtgaaacg ttgcgtggca aggcgaccg cacgcgggcg ggcgctccta ggctcttgcc    120
cagcggttat tgtgatgggc ttgaggctcg tggcgcctgg cgctgcgact ccgaccgcta   180
ttagcgcggc gtagtgagga cctttttgcc gtattgttag gtagaactgc attttaatga   240
ctgtgtccct gctgttgccc gaagtgacgg ggcgacctcc cggcacaatg aaatgcttgt   300
gtgaaagaga ttttaaaag gaagagagaa attggggaat aaaacgctga attgaaggaa   360
attgaaaaga ggagaatagg attccgttga aaggagata agaggttatg ggttttttaa   420 aatgtattt aatttgaaat gaaaaaatca ggatgtctac cttgtatggg gtaaaaatga   480
ccagg                                                              485

<210> SEQ ID NO 16
<211> LENGTH: 35
<212> TYPE: DNA
<213> ORGANISM: Artificial sequence
<220> FEATURE:
<223> OTHER INFORMATION: synthetic

<400> SEQUENCE: 16
aggaagagag gtaatgaggt aaattgggg tagtt                               35

<210> SEQ ID NO 17
<211> LENGTH: 56
<212> TYPE: DNA
<213> ORGANISM: Artificial sequence
<220> FEATURE:
<223> OTHER INFORMATION: synthetic

<400> SEQUENCE: 17
cagtaatacg actcactata gggagaaggc tttcaataac aaaacctctt ccactc        56

<210> SEQ ID NO 18
<211> LENGTH: 409
<212> TYPE: DNA
<213> ORGANISM: Homo sapiens

<400> SEQUENCE: 18
gcaatgaggc aaattggggg cagcctcagc cctgaccacc caagtcgagc aggcttttac    60
```

```
actggctcct cttcccttc ttaaaacgtt acagaaacaa ggccaattag atcctcaaag      120
taattcatct ctaagtatga aaaaagcaga ccacagggga agcggcgggt gggggtggg      180 gagattaaga tagcgctcgt tagagccgag gctccggagt gcgtcctgga acccacgggt   240
agaatttaca ggccgggacc attgtctgag atgctgaaaa gttaacccat caaacagcgg   300
gcgagggggc tcagggcact gaaagctccg gggatcaatg ttcaaaacgt ttaggaatta   360
agtcaaacta agggatatgg gcctgagtgg aagaggcttt gccactgaa               409
```

```
<210> SEQ ID NO 19
<211> LENGTH: 35
<212> TYPE: DNA
<213> ORGANISM: Artificial sequence
<220> FEATURE:
<223> OTHER INFORMATION: synthetic

<400> SEQUENCE: 19
aggaagagag gagatgtttt ttggagttgg tttag                              35
```

```
<210> SEQ ID NO 20
<211> LENGTH: 56
<212> TYPE: DNA
<213> ORGANISM: Artificial sequence
<220> FEATURE:
<223> OTHER INFORMATION: synthetic

<400> SEQUENCE: 20
cagtaatacg actcactata gggagaaggc taatttctat tcccattaat cccaaa        56
```

```
<210> SEQ ID NO 21
<211> LENGTH: 408
<212> TYPE: DNA
<213> ORGANISM: Homo sapiens

<400> SEQUENCE: 21
gagatgccct ttggagttgg ctcaggttag ggcaaggagg ccagagcctc atgccctcac   60
attgacccgt cattgtatgc aggtggccac caggagacat gatcttgggc cacacgtttc   120
tcttccatac agtgcaactc tcaaagaagg attcaactga gccatcggcc agcgcactcc   180
cgcagccgga ggacagagtg ctgagtcagg gtgtgggtgg aggggcaggg cgctcaggac   240
cgccaggttc ccagcggggt gagcagctgt gaggagactg agccctgcag ctggaatgag   300
gaagtgggag gagcagatgg catcagagag aggacagatt tcgttttgag ctggtggcat   360
ttaaacgctg gagaaggtgt cgacctggga tcaatgggaa tagaaacc                408
```

```
<210> SEQ ID NO 22
<211> LENGTH: 39
<212> TYPE: DNA
<213> ORGANISM: Artificial sequence
<220> FEATURE:
<223> OTHER INFORMATION: synthetic

<400> SEQUENCE: 22
aggaagagag taatgagggt ttatttaaat gattttga                           39
```

```
<210> SEQ ID NO 23
<211> LENGTH: 52
<212> TYPE: DNA
<213> ORGANISM: Artificial sequence
<220> FEATURE:
<223> OTHER INFORMATION: synthetic

<400> SEQUENCE: 23
```

```
cagtaatacg actcactata gggagaaggc taacactaaa cccccaaatc tc          52
```

<210> SEQ ID NO 24
<211> LENGTH: 472
<212> TYPE: DNA
<213> ORGANISM: Homo sapiens

<400> SEQUENCE: 24

```
caatgagggc ttatttaaat gatctctgag gtcttggacc caggccaatc agctgtcagg   60
gctcatgata aatcgcaatg cattattgat aataataatt actgggacat gcgcgttccg  120
gccgaagggg ggtaaatttc ccaactccag gaatttgtgg cggagagggc aaataactgc  180
ggctctcccg gcgccccgat gctcgcacca tgtcgaggcg caagcaggcg aaaccccagc  240
acatcaactc ggaggaggac cagggcgagc agcagccgca gcagcagacc ccggagtttg  300
cagatgcggc cccagcggcg cccgcggcgg gggagctggg tgagtggggc tggggcgccc  360
gcccggggag gggagcttcc cggacgtacg cgggatcctc gagggcgcag gcttcgggga  420
gcgggcggcg tccagcgcaa attcaggagc cgagatttgg gggctcagtg cc          472
```

<210> SEQ ID NO 25
<211> LENGTH: 35
<212> TYPE: DNA
<213> ORGANISM: Artificial sequence
<220> FEATURE:
<223> OTHER INFORMATION: synthetic

<400> SEQUENCE: 25

```
aggaagagag ggagttggtt gtgattatgg agtta                              35
```

<210> SEQ ID NO 26
<211> LENGTH: 56
<212> TYPE: DNA
<213> ORGANISM: Artificial sequence
<220> FEATURE:
<223> OTHER INFORMATION: synthetic

<400> SEQUENCE: 26

```
cagtaatacg actcactata gggagaaggc taaaacaaca ccctacccctc taaaac       56
```

<210> SEQ ID NO 27
<211> LENGTH: 461
<212> TYPE: DNA
<213> ORGANISM: Homo sapiens

<400> SEQUENCE: 27

```
ggagctggct gtgactatgg agccacacaa cgaagtggag atagggcagt catccagctt   60
atttgatctg tgtagacagc taaaggagag cacttcaggc ttcaaagtct agaaggaatg  120
tctacactga tcaaacggcg ggccaggccg ttgtcagatc tcctctcctg ccagagagcc  180
cggcagcctt tgttcattgt tgggcttgag gctgcagggt ttgtctccca catgcgcct  240
ccaagttcca cagctgcttt cgaggcctgt cctcggccaa agggtgtcgt gggagaggtt  300
tgcttgttgt ccccggtctc tctgttccct ttgtctccta atcctcaagc actatgctct  360
aacactccct tctctattca aaacctgtct atgagtctgc tgttttacac atcgatctcc  420
ctcactagac cattaggtcc tagagggcag ggtgctgtct t                      461
```

<210> SEQ ID NO 28
<211> LENGTH: 35
<212> TYPE: DNA

```
<213> ORGANISM: Artificial sequence
<220> FEATURE:
<223> OTHER INFORMATION: synthetic

<400> SEQUENCE: 28
aggaagagag gtagtatttg gtggatggga agatt                              35

<210> SEQ ID NO 29
<211> LENGTH: 56
<212> TYPE: DNA
<213> ORGANISM: Artificial sequence
<220> FEATURE:
<223> OTHER INFORMATION: synthetic

<400> SEQUENCE: 29
cagtaatacg actcactata gggagaaggc tactaaactt ctccctctct cctctc       56

<210> SEQ ID NO 30
<211> LENGTH: 302
<212> TYPE: DNA
<213> ORGANISM: Homo sapiens

<400> SEQUENCE: 30
gcagcacctg gtggatggga agatttagag aaccgtagaa gccgagtgag aaaggagggc   60
ccagctggga aatccgtaga ctgcctagag gaatatttgc agccgcagca cacaacacaa  120
tgagatctgt ccgctttgtg cagcgcaccg gcaggcgtga ctgcagggac ccgacccctc  180
ccccgcccga aacctccacc ctagctagat acgttcaact caggcaatgg atggcctggg  240
atcactctgt gagagtggag caggggagcg ggatgcagag aggagagagg gagaagccca  300
gc                                                                 302

<210> SEQ ID NO 31
<211> LENGTH: 35
<212> TYPE: DNA
<213> ORGANISM: Artificial sequence
<220> FEATURE:
<223> OTHER INFORMATION: synthetic

<400> SEQUENCE: 31
aggaagagag tttgttgttg gaagtaatgt gttta                              35

<210> SEQ ID NO 32
<211> LENGTH: 59
<212> TYPE: DNA
<213> ORGANISM: Artificial sequence
<220> FEATURE:
<223> OTHER INFORMATION: synthetic

<400> SEQUENCE: 32
cagtaatacg actcactata gggagaaggc tactattacc atacacaact catcccta     59

<210> SEQ ID NO 33
<211> LENGTH: 500
<212> TYPE: DNA
<213> ORGANISM: Homo sapiens

<400> SEQUENCE: 33
cttgctgttg gaagcaatgt gcttagcagg cctgggaaac gctgcctcac agtggcaccg   60
ggacgtggtc aggcccgcgg catgacagac agcaacagct tcccagacgc cgttccccca  120
acaatctgcc agcgagaaag atttacaaag gcaatagga tggcctcgtc acagcgcaaa   180
caaacggtat ttaatgttcc ataaataagc acgccaacgc cttaataagg gtccttcgtc  240
```

```
cagcccgggg cccaacctgg gacatcgttc ctcagaggta ctggaatatt cccctggtc      300 cgacgcacac atcattttaa agcatccttt ttgaattctg ttttcaagga attaaaaaat    360
atccaagttg ttcatggcta gctgagatct tcctttgaaa aacacgacac agaactgaaa    420
tattccaatc tgccaggtaa ctccaccctc cacggaaaca cctctagaac gtcagggat     480 gagctgtgca tggtaatagc                                                500
```

```
<210> SEQ ID NO 34
<211> LENGTH: 20
<212> TYPE: DNA
<213> ORGANISM: Artificial sequence
<220> FEATURE:
<223> OTHER INFORMATION: synthetic

<400> SEQUENCE: 34
gcgctgaagc tgaagaagat                                                 20

<210> SEQ ID NO 35
<211> LENGTH: 20
<212> TYPE: DNA
<213> ORGANISM: Artificial sequence
<220> FEATURE:
<223> OTHER INFORMATION: synthetic

<400> SEQUENCE: 35
ttcagcgtgg ctatcagttg                                                 20

<210> SEQ ID NO 36
<211> LENGTH: 22
<212> TYPE: DNA
<213> ORGANISM: Artificial sequence
<220> FEATURE:
<223> OTHER INFORMATION: synthetic

<400> SEQUENCE: 36
gcgaaaggca aagaggaaag tc                                              22

<210> SEQ ID NO 37
<211> LENGTH: 22
<212> TYPE: DNA
<213> ORGANISM: Artificial sequence
<220> FEATURE:
<223> OTHER INFORMATION: synthetic

<400> SEQUENCE: 37
cctttcccga tcacttccaa ac                                              22

<210> SEQ ID NO 38
<211> LENGTH: 20
<212> TYPE: DNA
<213> ORGANISM: Artificial sequence
<220> FEATURE:
<223> OTHER INFORMATION: synthetic

<400> SEQUENCE: 38
gcaggcattg tccagcctaa                                                 20

<210> SEQ ID NO 39
<211> LENGTH: 20
<212> TYPE: DNA
<213> ORGANISM: Artificial sequence
<220> FEATURE:
<223> OTHER INFORMATION: synthetic
```

```
<400> SEQUENCE: 39
agtcatcagc cccaaagagg                                              20

<210> SEQ ID NO 40
<211> LENGTH: 20
<212> TYPE: DNA
<213> ORGANISM: Artificial sequence
<220> FEATURE:
<223> OTHER INFORMATION: synthetic

<400> SEQUENCE: 40
tggcaagaag aaggtctggt                                              20

<210> SEQ ID NO 41
<211> LENGTH: 19
<212> TYPE: DNA
<213> ORGANISM: Artificial sequence
<220> FEATURE:
<223> OTHER INFORMATION: synthetic

<400> SEQUENCE: 41
aaggtgtttt tccggcatc                                               19
```